United States Patent
Schulzchen et al.

(10) Patent No.: US 9,163,243 B2
(45) Date of Patent: Oct. 20, 2015

(54) NUCLEIC ACIDS SPECIFICALLY BINDING CGRP

(71) Applicant: NOXXON Pharma AG, Berlin (DE)

(72) Inventors: Simone Schulzchen, Berlin (DE); Werner Purschke, Berlin (DE); Florian Jarosch, Berlin (DE); Kai Hohlig, Berlin (DE); Christian Maasch, Berlin (DE); Sven Klussmann, Berlin (DE)

(73) Assignee: NOXXON Pharma AG, Berlin (DE)

( * ) Notice: Subject to any disclaimer, the term of this patent is extended or adjusted under 35 U.S.C. 154(b) by 0 days.

(21) Appl. No.: 14/371,210

(22) PCT Filed: Jan. 10, 2013

(86) PCT No.: PCT/EP2013/000055
§ 371 (c)(1),
(2) Date: Jul. 9, 2014

(87) PCT Pub. No.: WO2013/104539
PCT Pub. Date: Jul. 18, 2013

(65) Prior Publication Data
US 2015/0031755 A1 Jan. 29, 2015

(30) Foreign Application Priority Data
Jan. 10, 2012 (WO) .................. PCT/EP2012/000089

(51) Int. Cl.
| C07H 21/02 | (2006.01) |
| C07H 21/04 | (2006.01) |
| A61K 48/00 | (2006.01) |
| C12N 15/115 | (2010.01) |
| C12Q 1/68 | (2006.01) |

(52) U.S. Cl.
CPC ............ *C12N 15/115* (2013.01); *C12Q 1/6876* (2013.01); *C12N 2310/16* (2013.01); *C12N 2310/344* (2013.01); *C12N 2310/351* (2013.01); *C12N 2320/10* (2013.01); *C12N 2320/30* (2013.01)

(58) Field of Classification Search
CPC . C12N 15/115; C12N 2310/16; C12N 15/113
See application file for complete search history.

(56) References Cited

U.S. PATENT DOCUMENTS

| 5,582,981 A | 12/1996 | Toole et al. |
| 5,840,867 A | 11/1998 | Toole et al. |
| 6,207,816 B1 | 3/2001 | Gold et al. |
| 6,682,886 B1 | 1/2004 | Gold et al. |
| 2002/0164707 A1 | 11/2002 | Adamou et al. |
| 2006/0183700 A1 | 8/2006 | Vater et al. |
| 2013/0165501 A1 | 6/2013 | Purschke et al. |

OTHER PUBLICATIONS

Pohl et al., "Gene . . . directions," Eur J Pharm 429:39-48, 2001.
Eaton et al., "Post . . . aptamers," Bioorg Med Chem 5:1087-1096, 1997.
Trevino et al., "Evolution . . . heterodeneity," PNAS 108:13492-13497, 2011.
Juhl et al., "Effect . . . model," Eur J Pharm 567:117-124, 2007.
Denekas et al., "Inhibition . . . oligonucleotide," Br J Pharm 148:536-543, 2006.
Recober et al., "Calcitonin . . . biology," Curr Opn Neurol 22:241-246, 2009.
Vater et al., "Toward . . . prospects," Curr Opn Drug Disc Dev 6:253-261, 2003.
Bunka et al., "Development . . . therapeutics," Curr Opn Pharm 10:557-562, 2010.
Ulrich, "RNA . . . therapy," Handbook Exp Pharm 173:305-326, 2006.
Durham et al., "Inhibition . . . migraine," Headache 48:1269-1275, 2008.
Herbison et al., "Sexually . . . nucleus," Mol Brain Res 34:143-148, 1995.
Novialis et al., "Reduction . . . cDNA," Pancreas 17:182-186, 1998.
Rusconi et al., "RNA . . . IXa," Nature 419:90-94, 2002.
Brain et al., "CGRP . . . migraine," Trends Pharm Sci 23:51-53, 2002.
Famulok et al., "Aptamers . . . immunology," Curr Top Micro Imm 243:123-136, 1999.
Williams et al., "Bioactive . . . vasopressin," PNAS 94:11285-11290, 1997.
Edvinsson et al., "Characterisation . . . arteries," Eur J Pharm 415:39-44, 2001.
Vater et al., "Short . . . SELEX," NAR 31:e130-e131, 2003.
Kanwar et al., "Chimeric . . . delivery," Crit Rev Biochem Mol Biol 46:459-477, 2011.

*Primary Examiner* — Amy Bowman
(74) *Attorney, Agent, or Firm* — MDIP LLC

(57) ABSTRACT

The present invention is related to a nucleic acid molecule capable of binding to CGRP, wherein the nucleic acid molecule comprises a central stretch of nucleotides, wherein the central stretch of nucleotides comprises a nucleotide sequence of 5' HW$n_1 n_2$YGGA$n_3 A n_4$UM$n_5 n_6$Y$n_7 n_8 n_9 n_{10} n_{11}$K$n_{12}$R$n_{13}$AD$n_{14} n_{15}$AR$n_{16}$U$n_{17}$C$n_{18} n_{19}$U$n_{20} n_{21}$ 3' [SEQ ID NO: 99], wherein H, W, Y, G, A, U, M, B, K, R, D, C are ribonucleotides, and $n_1$ is R or dG, $n_2$ is U or dT, $n_3$ is K or dG, $n_4$ is C or dC, $n_5$ is M or dC, $n_6$ is B or dU, $n_7$ is N or dG, $n_8$ is Y or dT, $n_9$ is N or dC, $n_{10}$ is R or dG, $n_{11}$ is V or dA, $n_{12}$ is K or dT or dU, $n_{13}$ is G or dG, $n_{14}$ is A or dA, $n_{15}$ is U or dT, $n_{16}$ is R or dG, $n_{17}$ is Y or dC, $n_{18}$ is C or dC, $n_{19}$ is B or dC, $n_{20}$ is C or dC, $n_{21}$ is C or dC, and dG, dT, dC, dA and dU are 2'-deoxyribonucleotides.

24 Claims, 18 Drawing Sheets

| Name | SEQ ID NO. | nt. | Sequence: 5'-3' | Comp (APM) |
|---|---|---|---|---|
| 212-G1-001 | 001 | 48 | CGUG CUGUCGGAGACUACUCGUCGAGUAGAAAUAGGUCCCCUCC CACG | = |
| 226-F2-001 | 002 | 50 | CCGUG CUGUCGGAGACUACUCGUCGAGUAGAAAUAGGUCCCCUCC CACGG | + |
| 212-F1-001 | 003 | 48 | CGUG CUGUCGGAGACUACUCGUCGAGUAGAUAAGGUCCCCUCC CACG | = |
| 224-B2-001 | 004 | 50 | GCGUG CUGUCGGAGACUACGCGUUCGCGUAGAGAUAGGUCCCCUCC CACGC | = |
| 224-E1-001 | 005 | 48 | GCAG CUGUCGGAGACUACCCGUCGGGUGAGAAAUAGGUCCCCUCC CUGC | = |
| 226-A2-002 | 006 | 48 | CGUG AUAUCGGAGACUACUCGUGAGUAGAAAUAGGUCCCCUCC CACG | -- |
| 226-A3-001 | 007 | 50 | CCGUG CUGUCGGAGACUACUCAUCGAGUAGAAAUAGGUCCCCUCC CACGG | + |
| 226-G2-002 | 008 | 48 | CGUG CAGUCGGAGACUACUCAUCGAGUAGAAAUAGGUCCCCUUCC CACG | -- |
| 226-C2-002 | 009 | 48 | CGUG CUGUCGGAGACUACUCGUAGAGGAGAUAGGUCCCCUCC CACG | -- |
| 226-E1-002 | 010 | 48 | CGUG CUGUCGGAGACUACUCGUAGAGUAGAUAAGUCCCCUCC UACG | -- |
| 226-F1-001 | 011 | 50 | CCGUG CUGUCGGAGACUACUCGUAGAGUAGAUAUAGGUCCCCUCC CACGG | = |
| 226-C3-001 | 012 | 50 | CCGUG CUGUCGGAGACUACUCGUAGAGUAGAAAUAGGUCCCCUCC CACGG | + | nt.: number of nucleotides; ☐ any of G, C, U and A is a ribonucleotide;
nucleotides edged by ☐ represents a CGRP-binding motif;
Comp(APM): Molecules of the indicated sequence were tested as aptamers (D-nucleic acid) in pull-down competition binding assay vs. 212-G1-001 as reference;
+: better binding affinity than 212-G1-001; =: similar binding affinity as 212-G1-001; --: much weaker binding affinity than 212-G1-001

Fig. 1A

| Name | SEQ ID NO. | nt. | Sequence: 5'-3' | Comp (APM) |
|---|---|---|---|---|
| 231-A1-001 | 013 | 52 | GUCAUG CUGUCGGAGACUACUCAUCGAGUAGAAAUAGGUCCCCUCC CACGGC | + |
| 231-G2-001 | 014 | 52 | GCCAUG CUGUCGGAGACUACUCAUCGAGUAGAAAUAGAUCCCCUCC CAUGGC | -- |
| 231-C1-001 | 015 | 52 | GCCGUG CUGUCGGAGACUACUCAUCGAGUAGAAAUAGGUCCCCUCC CACGGC | + |
| 231-C2-001 | 016 | 52 | GCCGUG CUGUCGGAGACUACUCGUGAGUAGAAAUAGGUCCCCUCC CACGGC | + |
| 231-D1-001 | 017 | 52 | GCCGUG CUGUCGGAGACUACUCGUUGAGUAGAAAUAGGUCCCCGUCC CACGGC | -- |
| 231-F1-001 | 018 | 52 | GCCGUG CUGUCGGAGACUACUCGCCGAGUAGAAAUAGGUCCCCUCC CACGGC | + |
| 231-E1-001 | 019 | 52 | CCCGUG CUGUCGGAGACUACUCGUCGAGUAGAAAUAGGUCCCCUCC CACGGG | + |
| 231-B3-001 | 020 | 54 | CACCGUG CUGUCGGAGAUACUACUCGCCGAGUAGAAAUAGGUCCCCUCC CACGGUG | -- |
| 231-A2-001 | 021 | 54 | GGCCGUG CUGUCGGAGACUACUCGCCGAGUAGAAAUAGGUCCCCUCC CACGGCU | + |
| 231-E2-001 | 022 | 52 | CCCGUG CUGUCGGAGACUACUCGUAGGGUAGAAAUAGGUCCCCUCC CACGGG | + |
| 231-H2-001 | 023 | 52 | GCCGUG UUGUCGGAGACUACCCCAGGGUAGAAAUAGGUCCCCUCC CACGGC | -- | nt.: number of nucleotides;  any of G, C, U and A is a ribonucleotide;
nucleotides edged by ☐ represents a CGRP-binding motif;
Comp(APM): Molecules of the indicated sequence were tested as aptamers (D-nucleic acid) in pull-down competition binding assay vs. 212-G1-001 as reference;
+: better binding affinity than 212-G1-001; =: similar binding affinity as 212-G1-001; --: much weaker binding affinity than 212-G1-001

Fig. 1B

| Name | SEQ ID NO. | nt. | Sequence: 5'-3' | Comp (APM) |
|---|---|---|---|---|
| 226-F2-001 | 002 | 50 | CCGUG CUGUCGGAGACUACUCGUCGAGUAGAAAUAGGUCCCCCUCC CACGG | = |
| 226-F2-003 | 024 | 50 | GCGUG CUGUCGGAGACUACUCGUCGAGUAGAAAUAGGUCCCCCUCC CACGC | + |
| 226-F2-004 | 025 | 50 | GGGUG CUGUCGGAGACUACUCGUCGAGUAGAAAUAGGUCCCCCUCC CACCC | = |
| 226-F2-005 | 026 | 50 | GCCUG CUGUCGGAGACUACUCGUCGAGUAGAAAUAGGUCCCCCUCC CAGGC | = | nt.: number of nucleotides;   any of G, C, U and A is a ribonucleotide;
nucleotides edged by ☐ represents a CGRP-binding motif;
Comp(APM): Molecules of the indicated sequence were tested as aptamers (D-nucleic acid) in pull-down competition binding assay vs. th...
226-F2-001 as reference;
=: similar binding affinity as 226-F2-001; +: better inding affinity than 226-F2-001;

Fig. 2

Derivatives of 226-F2-001

| Name | SEQ ID NO. | Sequence: 5'-3' | x-fold improved binding affinity | Biacore (SPM) $K_D$ [nM] |
|---|---|---|---|---|
| 226-F2-001 | 002 | CCGUG\|CUGUCGGAGACUACUCGUCGAGUAGAAAUAGGUCCCCUCC\|CACGG | 1.0 | 2.6 |
| 226-F2-001-D03 | 027 | CCdGUG\|CUGUCGGAGACUACUCGUCGAGUAGAAAUAGGUCCCCUCC\|CACGG | 4.06 | 0.64 |
| 226-F2-001-D05 | 028 | CCGUdG\|CUGUCGGAGACUACUCGUCGAGUAGAAAUAGGUCCCCUCC\|CACGG | 3.25 | 0.80 |
| 226-F2-001-D08 | 029 | CCGUG\|CUdGUCGGAGACUACUCGUCGAGUAGAAAUAGGUCCCCUCC\|CACGG | 4.64 | 0.56 |
| 226-F2-001-D09 | 030 | CCGUG\|CUGdTCGGAGACUACUCGUCGAGUAGAAAUAGGUCCCCUCC\|CACGG | 3.38 | 0.77 |
| 226-F2-001-D14 | 031 | CCGUG\|CUGUCGGAGdCUACUCGUCGAGUAGAAAUAGGUCCCCUCC\|CACGG | 3.21 | 0.81 |
| 226-F2-001-D16 | 032 | CCGUG\|CUGUCGGAGADdCUACUCGUCGAGUAGAAAUAGGUCCCCUCC\|CACGG | 1.78 | 1.46 |
| 226-F2-001-D19 | 033 | CCGUG\|CUGUCGGAGACUAdCUCGUCGAGUAGAAAUAGGUCCCCUCC\|CACGG | 8.39 | 0.31 |
| 226-F2-001-D22 | 034 | CCGUG\|CUGUCGGAGACUACUCdGUCGAGUAGAAAUAGGUCCCCUCC\|CACGG | 2.11 | 1.60 |
| 226-F2-001-D23 | 035 | CCGUG\|CUGUCGGAGACUACUCGdTCGAGUAGAAAUAGGUCCCCUCC\|CACGG | 4.48 | 0.58 | nucleotides edged by ☐ represents a CGRP-binding motif; SPM: Spiegelmer any of G, C, U and A is a ribonucleotide; any of dG, dC, dT and dA is a 2'-desoxyribonucleotide;

x-fold improved binding affinity: Improved binding affinity of Spiegelmers relative to 226-F2-001, measured by surface plasmon resonance on Biacore using direct binding to covalently immobilized human L-CGRP.

Biacore(SPM): Dissociation constant $K_D$ of Spiegelmers (L-nucleic acid), molecules of the indicated sequence were tested as Spiegelmers (L-nucleic acid) measured as surface plasmon resonance on Biacore using direct binding to biotinylated L-CGRP

Fig. 3A

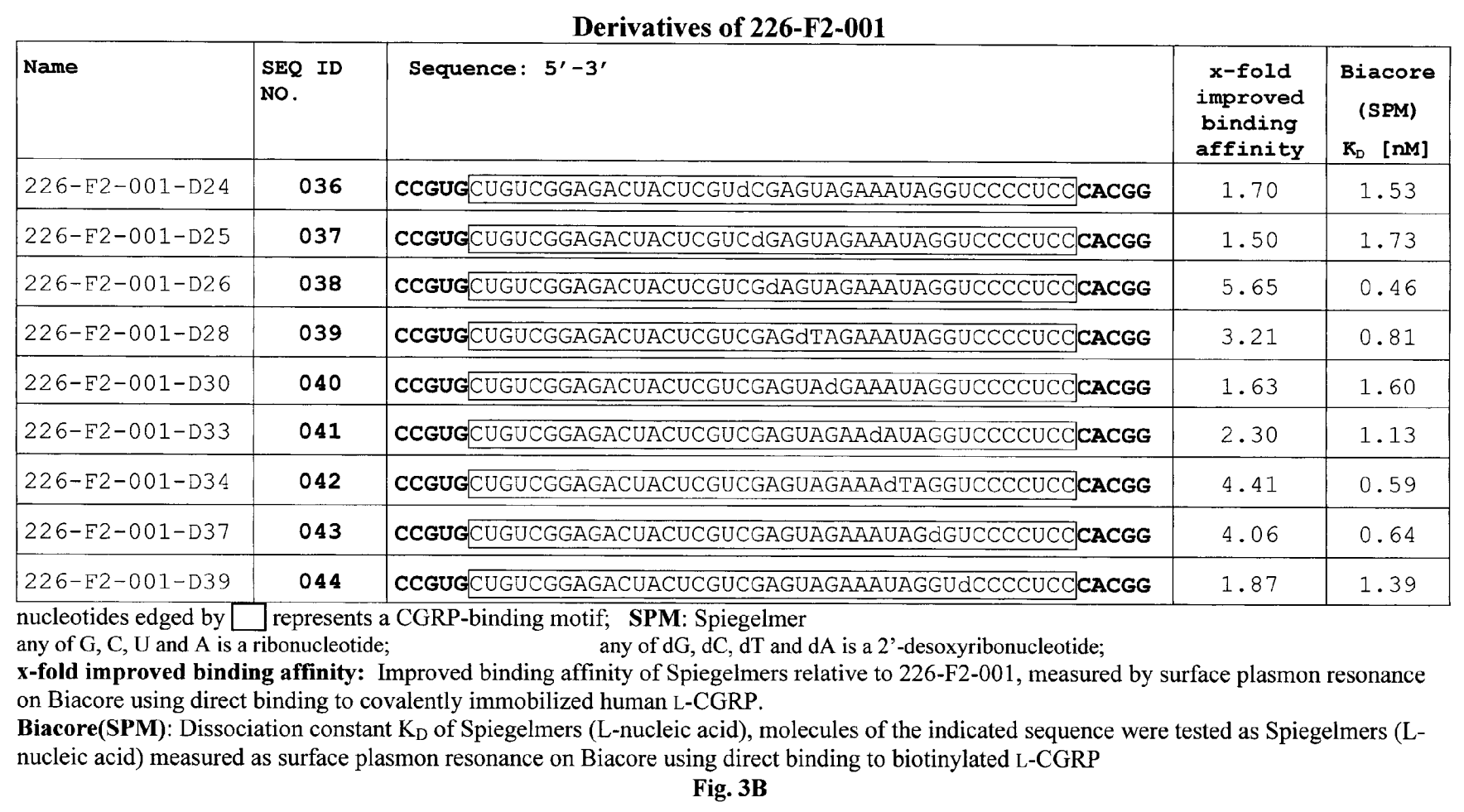

Derivatives of 226-F2-001

| Name | SEQ ID NO. | Sequence: 5'-3' | x-fold improved binding affinity | Biacore (SPM) K_D [nM] |

Derivatives of 226-F2-001

| Name | SEQ ID NO. | Sequence: 5'-3' | x-fold improved binding affinity | Biacore (SPM) $K_D$ [nM] |
|---|---|---|---|---|
| 226-F2-001-D41 | 045 | CCGUG CUGUCGGAGACUACUCGUCGAGUAGAAAUAGGUCCdCUCC CACGG | 5.2 | 0.50 |
| 226-F2-001-D42 | 046 | CCGUG CUGUCGGAGACUACUCGUCGAGUAGAAAUAGGUCCdCUCC CACGG | 5.00 | 0.52 |
| 226-F2-001-D44 | 047 | CCGUG CUGUCGGAGACUACUCGUCGAGUAGAAAUAGGUCCCCUdCC CACGG | 6.34 | 0.41 |
| 226-F2-001-D45 | 048 | CCGUG CUGUCGGAGACUACUCGUCGAGUAGAAAUAGGUCCCCUCdC CACGG | 5.00 | 0.52 |
| 226-F2-001-D46 | 049 | CCGUG CUGUCGGAGACUACUCGUCGAGUAGAAAUAGGUCCCCUCC dCACGG | 4.06 | 0.64 |
| 226-F2-001-D47 | 050 | CCGUG CUGUCGGAGACUACUCGUCGAGUAGAAAUAGGUCCCCUCC CdACGG | 3.77 | 0.69 |
| 226-F2-001-D48 | 051 | CCGUG CUGUCGGAGACUACUCGUCGAGUAGAAAUAGGUCCCCUCC CAdCGG | 4.64 | 0.56 |
| 226-F2-001-D49 | 052 | CCGUG CUGUCGGAGACUACUCGUCGAGUAGAAAUAGGUCCCCUCC CACdGG | 4.00 | 0.65 |
| 226-F2-001-D50 | 053 | CCGUG CUGUCGGAGACUACUCGUCGAGUAGAAAUAGGUCCCCUCC CACGdG | 3.17 | 0.82 |
| 226-F2-001-D41/D44 | 054 | CCGUG CUGUCGGAGACUACUCGUCGAGUAGAAAUAGGUCCdCUdCC CACGG | 13.00 | 0.20 | nucleotides edged by ☐ represents a CGRP-binding motif; SPM: Spiegelmer
any of G, C, U and A is a ribonucleotide; any of dG, dC, dT and dA is a 2'-desoxyribonucleotide;
x-fold improved binding affinity: Improved binding affinity of Spiegelmers relative to 226-F2-001, measured by surface plasmon resonance on Biacore using direct binding to covalently immobilized human L-CGRP.
Biacore(SPM): Dissociation constant $K_D$ of Spiegelmers (L-nucleic acid), molecules of the indicated sequence were tested as Spiegelmers (L-nucleic acid) measured as surface plasmon resonance on Biacore using direct binding to biotinylated L-CGRP

Fig. 3C

Derivatives of 226-F2-001

| Name | SEQ ID NO. | Sequence: 5'-3' | x-fold improved binding affinity | Biacore (SPM) K_D [nM] |
|---|---|---|---|---|
| 226-F2-001-D41-dU20 | 126 | CCGUG CUGUCGGAGACUACdUCGUCGAGUAGAAAUAGGUCCdCCUCC CACGG | 37.14 | 0.07 |
| 226-F2-001-D41-dU28 | 127 | CCGUG CUGUCGGAGACUACUCGUCGAGUAGAAAUAGGUCCdCCUCC CACGG | 12.38 | 0.21 |
| 226-F2-001-D41-dU20-28 | 128 | CCGUG CUGUCGGAGACUACdUCGUCGAGUAGAAAUAGGUCCdCCUCC CACGG | 4.19 | 0.62 |
| 226-F2-001-D41/D44-dU20 | 129 | CCGUG CUGUCGGAGACUACdUCGUCGAGUAGAAAUAGGUCCdCCUdCC CACGG | 6.34 | 0.41 |
| 226-F2-001-D41/D44-dU28 | 130 | CCGUG CUGUCGGAGACUACUCGUCGAGUAGAAAUAGGUCCdCCUdCC CACGG | 7.03 | 0.37 |
| 226-F2-001-D41/D44-dU20-28 | 131 | CCGUG CUGUCGGAGACUACdUCGUCGAGUAGAAAUAGGUCCdCCUdCC CACGG | 7.88 | 0.33 | nucleotides edged by ☐ represents a CGRP-binding motif, SPM: Spiegelmer
any of G, C, U and A is a ribonucleotide; any of dG, dC, dU and dA is a 2'-desoxyribonucleotide;
x-fold improved binding affinity: Improved binding affinity of Spiegelmers relative to 226-F2-001, measured by surface plasmon resonance on Biacore using direct binding to covalently immobilized human L-CGRP.
Biacore(SPM): Dissociation constant $K_D$ of Spiegelmers (L-nucleic acid), molecules of the indicated sequence were tested as Spiegelmers (L-nucleic acid) measured as surface plasmon resonance on Biacore using direct binding to biotinylated L-CGRP

Fig. 3D

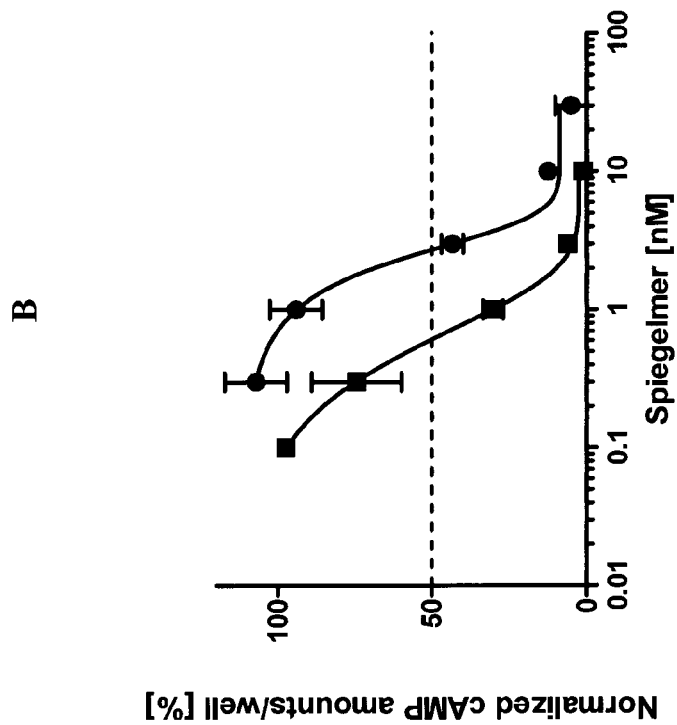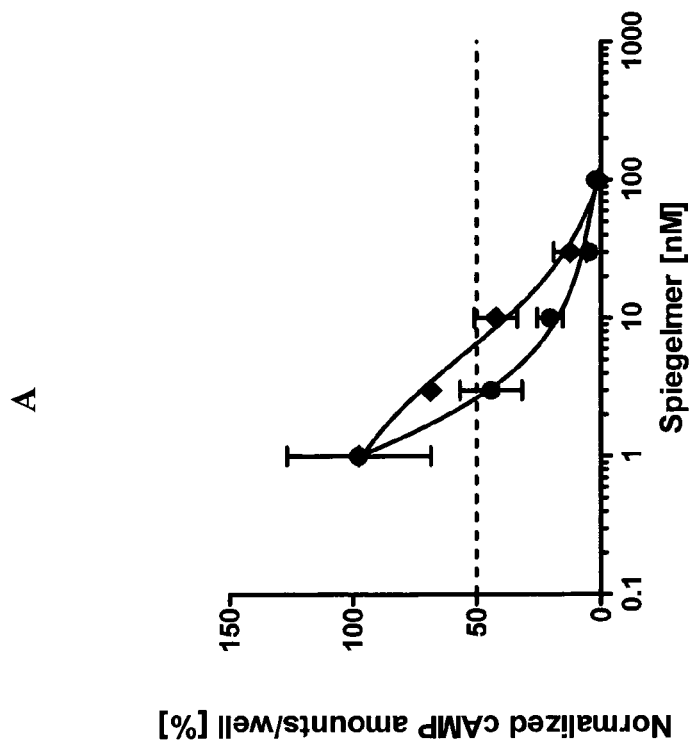
Fig. 7

A

| | | | | |
|---|---|---|---|---|
| Human alpha-CGRP: | | AC-DTATCV THRLAGLLSR SGGVVKNNFV PTNVGSKAF | [SEQ ID NO: 82] |
| Human beta-CGRP: | | AC-NTATCV THRLAGLLSR SGGMVKSNFV PTNVGSKAF | [SEQ ID NO: 83] |
| Human amylin: | | KC-NTATCA TQRLANFLVH SSNNFGAILS STNVGSNTY | [SEQ ID NO: 84] |
| Human calcitonin: | | -CGNLSTCM LGTYTQDFNK FHT-----FP QTAIGVGAP | [SEQ ID NO: 85] |
| Human adrenomedullin: | YRQSMNNFQGLRSFGC-RFGTCT | VQKLAHQIYQ FTDKDKDNVA PRSKISPQGY | [SEQ ID NO: 86] |
| Human intermedin: | TQAQLLRVGC-VLGTCQ | VQNLSHRLWQ LMGPAGRQDS APVDPSSPHSY | [SEQ ID NO: 87] |

B

Alpha-CGRP from

| | | |
|---|---|---|
| human: | ACDTATCV THRLAGLLSR SGGVVKNNFV PTNVGSKAF | [SEQ ID NO: 82] |
| macaca mulatta*: | ACDTATCV THRLAGLLSR SGGVVKNNFV PTNVGSKAF | [SEQ ID NO: 82] |
| rat: | SCNTATCV THRLAGLLSR SGGVVKDNFV PTNVGSEAF | [SEQ ID NO: 89] |
| mouse: | SCNTATCV THRLAGLLSR SGGVVKDNFV PTNVGSEAF | [SEQ ID NO: 89] |
| sus scorfa: | SCNTATCV THRLAGLLSR SGGMVKSNFV PTDVGSEAF | [SEQ ID NO: 91] |
| sheep: | SCNTATCV THRLAGLLSR SGGVVKSNFV PTNVGSQAF | [SEQ ID NO: 92] |
| dog: | SCNTATCV THRLAGLLSR SGGVVKNNFV PTNVGSEAF | [SEQ ID NO: 93] |

Fig. 8

| | | IC$_{50}$ (NOX-L41) | K$_D$ (226-F2-001-D41) |
|---|---|---|---|
| h-αCGRP | ACDTATCVTHRLAGLLSRSGGVVKNNFVPTNVGSKAF [SEQ ID NO: 82] | 0.39 nM | 0.55 nM |
| r-αCGRP | SCNTATCVTHRLAGLLSRSGGVVKDNFVPTNVGSEAF [SEQ ID NO: 89] | 3.6 nM | 0.57 nM |
| r-Amylin | KCNTATCATQRLANFLVRSSNNFGAILSPTNVGSNTY [SEQ ID NO: 94] | 283 nM | n.d. |
| h-Amylin | KCNTATCATQRLANFLVHSSNNFGAILSSTNVGSNTY [SEQ ID NO: 84] | >1000 nM | no binding |

Fig. 9

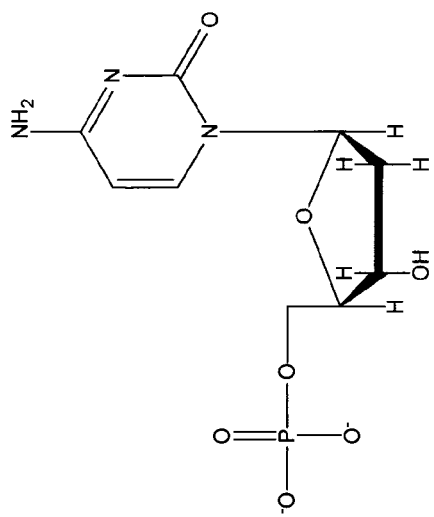
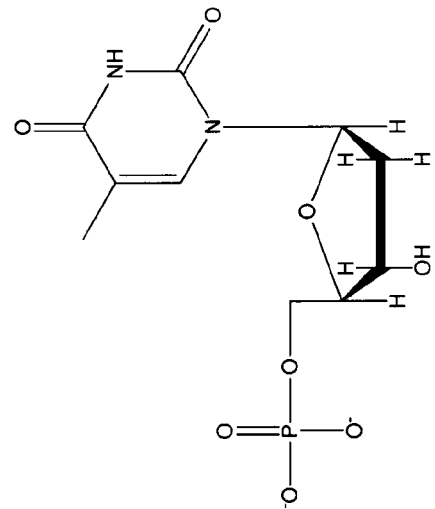
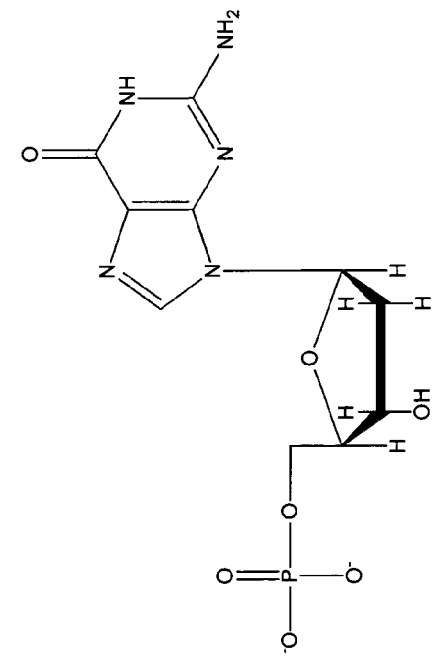
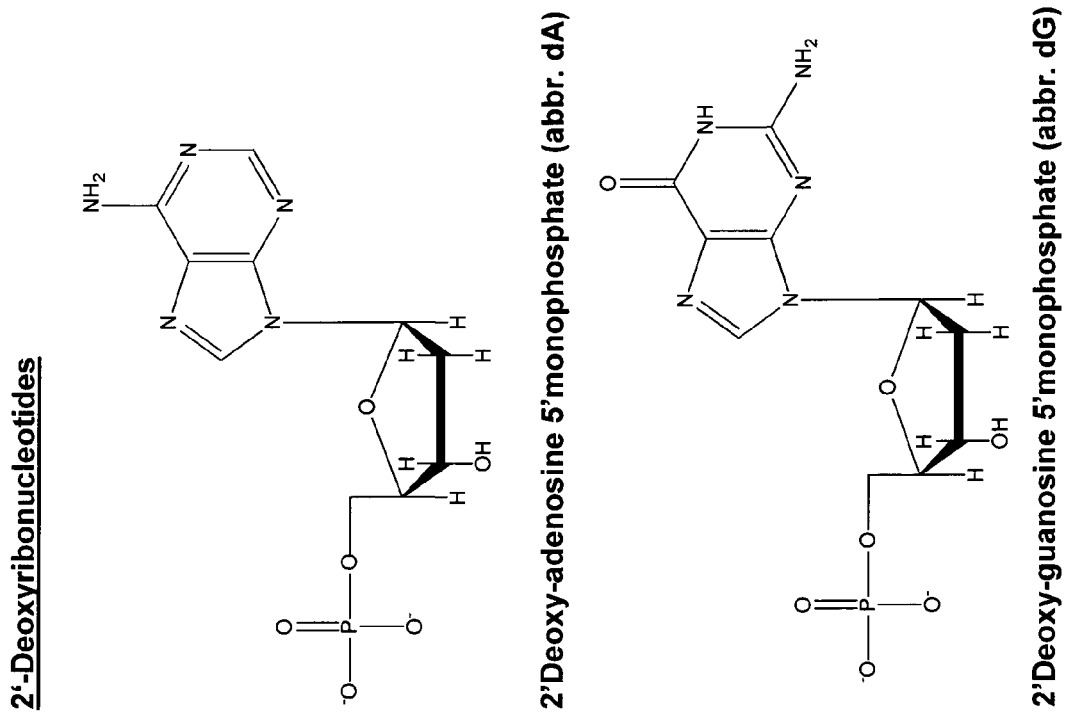
Fig. 11A

2'-Deoxyribonucleotides

2'Deoxy Uridine 5'monophosphate  (abbr. dU)

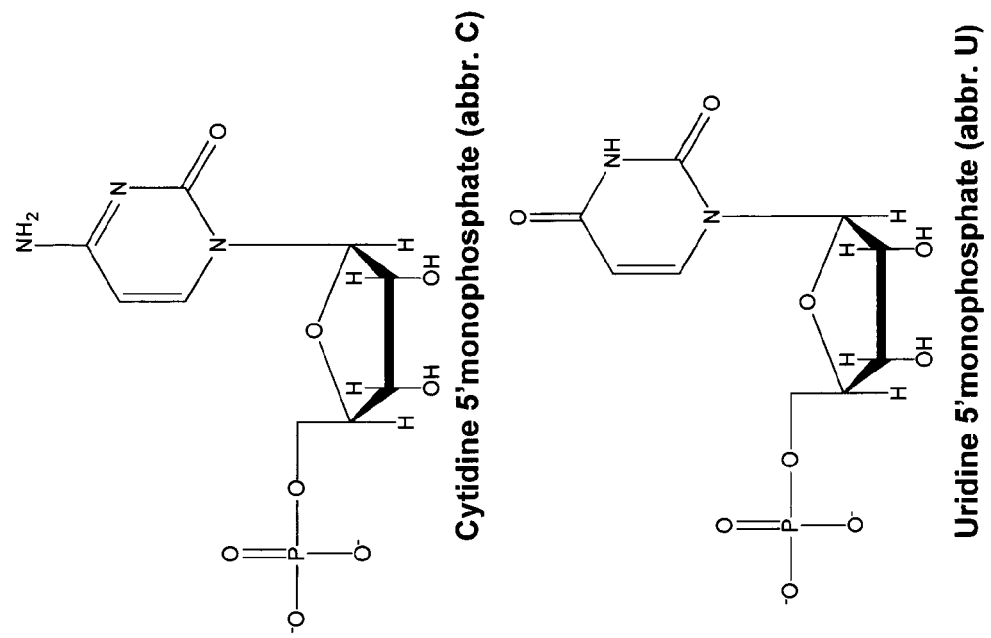
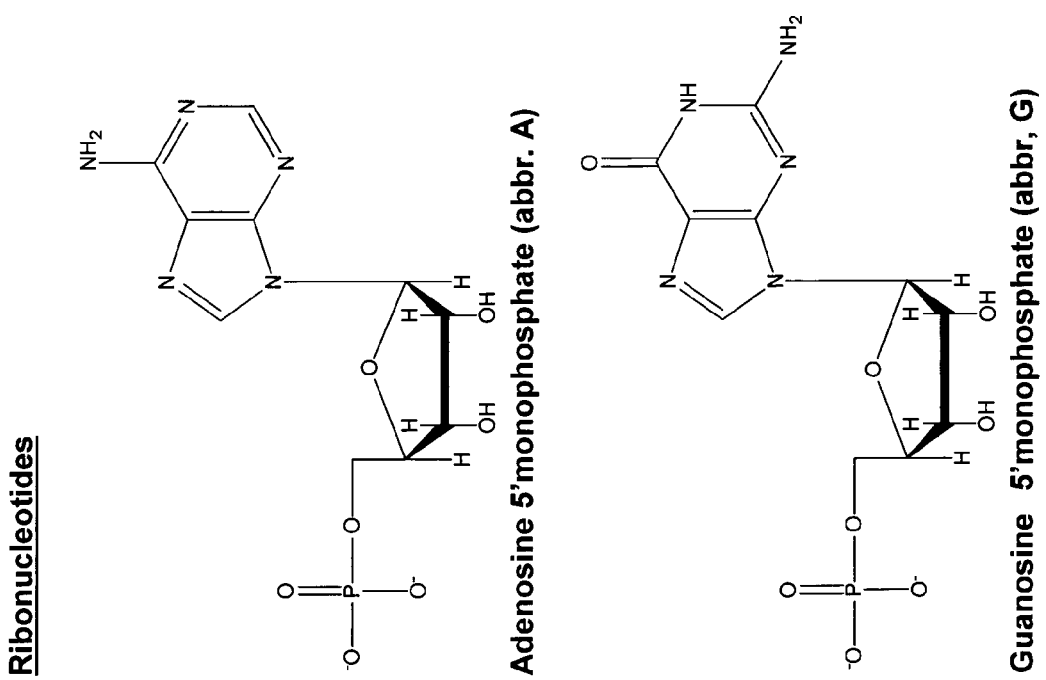
Fig. 12

NUCLEIC ACIDS SPECIFICALLY BINDING CGRP

The present invention is related to a nucleic acid molecule capable of a binding to calcitonin gene-related peptide (abbr. CGRP), the use thereof for the manufacture of a medicament, a diagnostic agent, and a detecting agent, respectively, a composition comprising said nucleic acid molecule, a complex comprising said nucleic acid molecule, a method for screening of an antagonist of an activity mediated by CGRP using said nucleic acid molecule, and a method for the detection of said nucleic acid molecule.

Alpha-CGRP is a 37-amino acid neuropeptide that is generated by alternative splicing of the calcitonin gene transcript (Amara, Jonas et al. 1982). CGRP is predominantly expressed in the peripheral and central nervous system (van Rossum, Hanisch et al. 1997). Although various functions have been described for CGRP, its best known actions in vivo are dural vasodilatation and transmission of nociception (Edvinsson and Ho 2010). The structure for human CGRP was determined in part by $^1$H-NMR. The peptide comprises a defined amino-terminal disulfide-bonded loop (residues 2-7) leading into a well-defined alpha-helix (residues 8 and 18). The C-terminal part of the peptide has no clearly defined structure (Breeze, Harvey et al. 1991).

Beta-CGRP is a peptide with high homology to alpha-CGRP (human alpha and beta CGRP only differ in 3 out of 37 amino acids, i.e. 95% identical amino acids) yet it is transcribed by a discrete gene. Both peptides are expressed in distinct anatomical locations but show similar biological actions (Edvinsson and Ho 2010). Other peptides showing sequence homology to human alpha-CGRP are human amylin (15, out of 37=41% identical amino acids to human alpha-CGRP), calcitonin (7, out of 37=19% identical), adrenomedullin (7, out of 37=19% identical), and intermedin (7, out of 37=19% identical) (see FIG. 8A).

The cellular receptor for CGRP is a heterodimer of the G-protein-coupled receptor calcitonin-like receptor (abr. CLR) and a small transmembrane protein called receptor activity-modifying protein 1 (abbr. RAMP1). Two other RAMPs, namely RAMP2 and RAMP3, have been cloned that may form heterodimers with CLR and determine selectivity to other members of the calcitonin family of peptides. For example, CLR and RAMP2 form a selective receptor for adrenomedullin (McLatchie, Fraser et al. 1998). Structural data confirmed that CLR and RAMP 1 together form a binding pocket for CGRP and that clinically effective CGRP receptor antagonists block this binding cleft (Raddant and Russo 2011). CGRP binding to its receptor results in increased intracellular cAMP levels.

Although various functions have been described for CGRP, its best known actions in vivo are dural vasodilatation and transmission of nociception (Edvinsson and Ho 2010). In fact, CGRP is widely used as a maker for nociceptive nerve fibres.

In Western countries approximately 10% of the adult population are affected by migraine with higher incidence in females. Migraine is a debilitating disease characterized by intensive recurring headaches associated with nausea or vomiting, or photophobia or phonophobia. In about 15% of patients headache is preceded by neurological symptoms, usually visual. This type of migraine is defined as migraine with aura (Goadsby 2003).

Current treatment options include standard analgesics (mainly nonsteroidal anti-inflammatory drugs (abbr. NSAIDs) such as acetylsalicylic acid, paracetamol, ibuprofen, and COX-2 inhibitors) and two classes of migraine-specific analgesics: vasoconstricting ergot alkaloid derivatives (e.g. dihydroergotamine) and triptans, 5-HT$_{1B/1D}$ receptor agonists (e.g. Sumatriptan). Although these drugs are highly efficient for many patients not all migraine patients can be adequately treated with currently available drugs, stressing the need for novel therapeutic options (Monteith and Goadsby 2011).

Several lines of evidence suggest a central role for CGRP in migraine pathology. Vasodilation of cerebral vessels is regarded as a crucial mechanism for the development of headache pain in migraine. CGRP is known as a potent vasodilator and it was shown that stimulation of the trigeminal ganglion results in release of CGRP from trigeminal nerve endings and subsequent vasodilatation that is mediated through CGRP receptors residing on vascular smooth muscle (Limmroth, Katsarava et al. 2001). Furthermore, plasma CGRP levels were elevated in patients during migraine attacks (Goadsby, Edvinsson et al. 1990; Gallai, Sarchielli et al. 1995; Juhasz, Zsombok et al. 2003), although other studies were unable to confirm this (Tvedskov, Lipka et al. 2005). In pediatric migraine an extracephalical source of CGRP has been suggested (Tfelt-Hansen and Ashina 2010). Remarkably, infusion of CGRP induces migraine-like headache in migraine patients but not in healthy individuals, suggesting an increased sensitivity to CGRP migraineurs (Lassen, Haderslev et al. 2002). Moreover, there is evidence that CGRP is involved in headaches different from migraine such as cluster headache, paroxysmal hemicrania, cervicogenic headache, and dialysis headache (Frese, Schilgen et al. 2005; Alessandri, Massanti et al. 2006; Tfelt-Hansen and Le 2009; Summ, Andreou et al. 2010). For example, plasma CGRP levels are elevated during cluster headache attacks that normalized after analgetic treatment (Goadsby and Edvinsson 1994; Tfelt-Hansen and Le 2009).

There is growing evidence that CGRP is involved in other mechanisms than vasodilatation that contribute to migraine pathophysiology. Neurogenic inflammation is a sterile type of inflammation that results from sensory nerve activation and is characterized by vasodilation, plasma protein extravasation, and release of proinflammatory mediators from resident mast cells. Perivascular release of CGRP from trigeminal nerve endings can trigger such inflammatory events by stimulating dura-resident mast cells and satellite glial cells (Ottosson and Edvinsson 1997; Raddant and Russo 2011). Furthermore, CGRP may directly impact on synaptic transmission of nociception resulting in increased sensitivity to sensory input as observed during migraine-associated photo- and phonophobia (Ho, Edvinsson et al. 2010).

The importance of CGRP in migraine is stressed by observations that administration of anti-migraine drugs such as dihydroergotamine or sumatriptan are able to reduce CGRP levels (Limmroth, Katsarava et al. 2001; Stepien, Jagustyn et al. 2003). The peptide fragment CGRP(8-37) antagonizes the function of CGRP by blocking its receptor. CGRP(8-37) was successfully used in a variety of migraine and pain models but its use is limited due to poor biostability. Several non-peptidic small-molecule CGRP receptor antagonists have been developed. Olcegepant (BIBN4096BS), an intravenously formulated CGRP receptor antagonist, was effective in treating acute attacks of migraine (Olesen, Diener et al. 2004). Despite these promising results its development was stopped probably due to the lack of oral availability. An orally available follow-on compound of Olcegepant, BI-44370 TA, recently showed dose-dependent efficacy in a phase II trial for acute migraine (Diener, Barbanti et al. 2011). Telcagepant (MK-0974) is an orally available CGRP receptor antagonist developed for the potential treatment of migraine. It showed efficacy in phase III clinical trials for acute migraine (Ho, Ferrari et al. 2008; Connor, Shapiro et al. 2009) but its development was recently discontinued presumably because of signs of liver toxicity from a prophylaxis clinical trial (Raddant and Russo 2011). BMS-927711 is currently developed for the potential oral capsule treatment of migraine in a phase II clinical trial. Anti-CGRP monoclonal antibodies effectively inhibited neurogenic vasodilatation (Tan, Brown et al. 1995; Zeller, Poulsen et al. 2008). Two monoclonal antibodies targeting CGRP are currently developed. Both antibodies are currently in phase I clinical trials for the potential treatment of migraine. However, because of their potential immunogenicity, these and other antibodies might not be a viable option for the long-term treatment of migraine.

Essentially, attempts for therapeutic intervention through lowering CGRP levels/activity have yielded a lot of results supporting the concept of CGRP antagonism as a potential treatment of migraine, but have not lead to compounds with enough potency or sufficient safety profile.

We have previously described Spiegelmers binding rat CGRP and, with lower affinity, human CGRP (Vater, Jarosch et al. 2003). In animal models, these Spiegelmers effectively inhibited CGRP-induced vasodilation (Edvinsson, Nilsson et al. 2007; Juhl, Edvinsson et al. 2007), prevented increases in meningeal artery blood flow after electrical stimulation (Denekas, Troltzsch et al. 2006) and abolished strain-related hypersensitivity to noxious heat (Mogil, Miermeister et al. 2005).

Amylin or Islet Amyloid Polypeptide (abbr. IAPP) is a 37-amino acid peptide hormone showing 41% identical amino acid residues to α-CGRP in human. Amylin is secreted along with insulin from the B-cells of Langerhans' islets. It contributes to controlling blood sugar levels by slowing down gastric emptying, inhibition of digestive secretion, and a resulting reduction in food intake. Besides, it causes a feeling of fullness and thirst, apparently through interaction with the central nervous system (Field, Chaudhri et al. 2010). In accordance therewith, injection of amylin results in reduced food intake in rats (Lutz, Del Prete et al. 1994; Morley, Flood et al. 1994). Due to this anorectic effect inhibition of amylin may lead to increased food intake and obesity (Lutz 2006). As a consequence cross-reactivity of CGRP-binding Spiegelmers to amylin is a major obstacle for the potential treatment of migraine.

The problem underlying the present invention is to provide a means which specifically binds to human CGRP, prefer human alpha-CGRP, without interacting with amylin, preferably human amylin and which antagonizes of an activity mediated by CGRP, prefer human alpha-CGRP, whereby the means is suitable for the prevention and/or treatment of diseases and conditions such as migraine, acute and chronic pain or tolerance to morphine-based analgesia.

These and other problems underlying the present invention are solved by the subject matter of the attached independent claims. Preferred embodiments may be taken from the dependent claims.

The problem underlying the present invention is solved in a first aspect, which is also the first embodiment of the first aspect, by a nucleic acid molecule capable of binding to CGRP, wherein the nucleic acid molecule comprises a central stretch of nucleotides, wherein the central stretch of nucleotides comprises a nucleotide sequence of

[SEQ ID NO: 99]
5' HWn$_1$n$_2$YGGAn$_3$AN$_4$UMn$_5$n$_6$Yn$_7$n$_8$n$_9$n$_{10}$n$_{11}$Kn$_{12}$Rn$_{13}$ADn$_{14}$n$_{15}$ARn$_{16}$Un$_{17}$Cn$_{18}$n$_{19}$Un$_{20}$n$_{21}$ 3', wherein H, W, Y, G, A, U, M, B, K, R, D, C are ribonucleotides, and n$_1$ is R or dG, n$_2$ is U or dT, n$_3$ is K or dG, n$_4$ is C or dC, n$_5$ is M or dC, n$_6$ is B or dU, n$_7$ is N or dG, n$_8$ is Y or dT, n$_9$ is N or dC, n$_{10}$ is R or dG, n$_{11}$ is V or dA, n$_{12}$ is K or dT or dU, n$_{13}$ is G or dG, n$_{14}$ is A or dA, n$_{15}$ is U or dT, n$_{16}$ is R or dG, n$_{17}$ is Y or dC, n$_{18}$ is C or dC, n$_{19}$ is B or dC, n$_{20}$ is C or dC, n$_{21}$ is C or dC, and dG, dT, dC, dA and dU are 2'-deoxyribonucleotides.

In a second embodiment of the first aspect which is also an embodiment of the first embodiment of the first aspect, the central stretch of nucleotides comprises a nucleotide sequence of

[SEQ ID NO: 100]
5' CUn$_1$n$_2$YGGAn$_3$AN$_4$UMn$_5$n$_6$Bn$_7$n$_8$n$_9$n$_{10}$n$_{11}$Kn$_{12}$An$_{13}$ADn$_{14}$n$_{15}$AGn$_{16}$Un$_{17}$Cn$_{18}$n$_{19}$Un$_{20}$n$_{21}$ 3' wherein C, U, Y, G, A, M, B, Y, H, K, D, R and V are ribonucleotides, and n$_1$ is G or dG, n$_2$ is U or dT, n$_3$ is G or dG, n$_4$ is C or dC, n$_5$ is M or dC, n$_6$ is B or dU, n$_7$ is D or dG, n$_8$ is Y or dT, n$_9$ is H or dC, n$_{10}$ is R or dG, n$_{11}$ is V or dA, n$_{12}$ is K or dT or dU, n$_{13}$ is G or dG, n$_{14}$ is A or dA, n$_{15}$ is U or dT, n$_{16}$ is G or dG, n$_{17}$ is Y or dC, n$_{18}$ is C or dC, n$_{19}$ is C or dC, n$_{20}$ is C or dC, n$_{21}$ is C or dC, and dG, dT, dC, dA and dU are 2'-deoxyribonucleotides.

In a third embodiment of the first aspect which is also an embodiment of the first and the second embodiment of the first aspect, the central stretch of nucleotides comprises a nucleotide sequence of

[SEQ ID NO: 101]
5' CUn$_1$n$_2$CGGAn$_3$An$_4$UAn$_5$n$_6$Cn$_7$n$_8$n$_9$n$_{10}$n$_{11}$Gn$_{12}$An$_{13}$AAn$_{14}$n$_{15}$AGn$_{16}$Un$_{17}$Cn$_{18}$n$_{19}$Un$_{20}$n$_{21}$ 3' wherein C, U, Y, G, A, H and R are ribonucleotides, and n$_1$ is G or dG, n$_2$ is U or dT, n$_3$ is G or dG, n$_4$ is C or dC, n$_5$ is C or dC, n$_6$ is U or dU, n$_7$ is R or dG, n$_8$ is Y or dT, n$_9$ is H or dC, n$_{10}$ is G or dG, n$_{11}$ is R or dA, n$_{12}$ is U or dT or dU, n$_{13}$ is G or dG, n$_{14}$ is A or dA, n$_{15}$ is U or dT, n$_{16}$ is G or dG, n$_{17}$ is C or dC, n$_{18}$ is C or dC, n$_{19}$ is C or dC, n$_{20}$ is C or dC, n$_{21}$ is C or dC, and dG, dT, dC, dA and dU are 2'-deoxyribonucleotides.

In a fourth embodiment of the first aspect which is also an embodiment of the first, second and third embodiment of the first aspect, the central stretch of nucleotides comprises a nucleotide sequence of

[SEQ ID NO: 102]
5' CUn$_1$n$_2$CGGAn$_3$An$_4$UAn$_5$n$_6$Cn$_7$n$_8$n$_9$n$_{10}$n$_{11}$Gn$_{12}$An$_{13}$AAn$_{14}$n$_{15}$AGn$_{16}$Un$_{17}$Cn$_{18}$n$_{19}$Un$_{20}$n$_{21}$ 3' wherein C, U, G, A, are ribonucleotides, and n$_1$ is G or dG, n$_2$ is U or dT, n$_3$ is G or dG, n$_4$ is C or dC, n$_5$ is C or dC, n$_6$ is U or dU, n$_7$ is G or dG, n$_8$ is U or dT, n$_9$ is C or dC, n$_{10}$ is G or dG, n$_{11}$ is A or dA, n$_{12}$ is U or dT or dU, n$_{13}$ is G or dG, n$_{14}$ is A or dA, n$_{15}$ is U or dT, n$_{16}$ is G or dG, n$_{17}$ is C or dC, n$_{18}$ is C or dC, n$_{19}$ is C or dC, n$_{20}$ is C or dC, n$_{21}$ is C or dC, and dG, dT, dC, dA and dU are 2'-deoxyribonucleotides.

In a fifth embodiment of the first aspect which is also an embodiment of the first, second, third and fourth embodiment of the first aspect, the central stretch of nucleotides comprises a nucleotide sequence selected from the group of (1)
[SEQ ID NO: 103]
5' CUdGUCGGAGACUACUCGUCGAGUAGAAAUAGGUCCCCUCC 3', (2)
[SEQ ID NO: 104]
5' CUGdTCGGAGACUACUCGUCGAGUAGAAAUAGGUCCCCUCC 3', (3)
[SEQ ID NO: 105]
5' CUGUCGGAdGACUACUCGUCGAGUAGAAAUAGGUCCCCUCC 3', (4)
[SEQ ID NO: 106]
5' CUGUCGGAGAdCUACUCGUCGAGUAGAAAUAGGUCCCCUCC 3', (5)
[SEQ ID NO: 107]
5' CUGUCGGAGACUAdCUCGUCGAGUAGAAAUAGGUCCCCUCC 3', (6)
[SEQ ID NO: 108]
5' CUGUCGGAGACUACUCdGUCGAGUAGAAAUAGGUCCCCUCC 3', (7)
[SEQ ID NO: 109]
5' CUGUCGGAGACUACUCGdTCGAGUAGAAAUAGGUCCCCUCC 3', (8)
[SEQ ID NO: 110]
5' CUGUCGGAGACUACUCGUdCGAGUAGAAAUAGGUCCCCUCC 3', (9)
[SEQ ID NO: 111]
5' CUGUCGGAGACUACUCGUCdGAGUAGAAAUAGGUCCCCUCC 3',

(10)
[SEQ ID NO: 112]
5' CUGUCGGAGACUACUCGUCGdAGUAGAAAUAGGUCCCCUCC 3',

(11)
[SEQ ID NO: 113]
5' CUGUCGGAGACUACUCGUCGAGdTAGAAAUAGGUCCCCUCC 3',

(12)
[SEQ ID NO: 114]
5' CUGUCGGAGACUACUCGUCGAGUAdGAAAUAGGUCCCCUCC 3'

(13)
[SEQ ID NO: 115]
5' CUGUCGGAGACUACUCGUCGAGUAGAAdAUAGGUCCCCUCC 3'

(14)
[SEQ ID NO: 116]
5' CUGUCGGAGACUACUCGUCGAGUAGAAAdTAGGUCCCCUCC 3',

(15)
[SEQ ID NO: 117]
5' CUGUCGGAGACUACUCGUCGAGUAGAAAUAGdGUCCCUCC 3',

(16)
[SEQ ID NO: 118]
5' CUGUCGGAGACUACUCGUCGAGUAGAAAUAGGUdCCCCUCC 3',

(17)
[SEQ ID NO: 119]
5' CUGUCGGAGACUACUCGUCGAGUAGAAAUAGGUCCdCCUCC 3',

(18)
[SEQ ID NO: 120]
5' CUGUCGGAGACUACUCGUCGAGUAGAAAUAGGUCCCdCUCC 3',

(19)
[SEQ ID NO: 121]
5' CUGUCGGAGACUACUCGUCGAGUAGAAAUAGGUCCCCUdCC 3',

(20)
[SEQ ID NO: 122]
5' CUGUCGGAGACUACUCGUCGAGUAGAAAUAGGUCCCCUCdC 3',

(21)
[SEQ ID NO: 123]
5' CUGUCGGAGACUACUCGUCGAGUAGAAAUAGGUCCdCCUdCC 3',

(22)
[SEQ ID NO: 130]
5' CUGUCGGAGACUACdUCGUCGAGUAGAAAUAGGUCCdCCUCC 3',

(23)
[SEQ ID NO: 131]
5' CUGUCGGAGACUACUCGUCGAGdUAGAAAUAGGUCCdCCUCC 3',

(24)
[SEQ ID NO: 132]
5' CUGUCGGAGACUACdUCGUCGAGdUAGAAAUAGGUCCdCCUCC 3',

(25)
[SEQ ID NO: 133]
5' CUGUCGGAGACUACdUCGUCGAGUAGAAAUAGGUCCdCCUdCC 3',

(26)
[SEQ ID NO: 134]
5' CUGUCGGAGACUACUCGUCGAGdUAGAAAUAGGUCCdCCUdCC 3',

(27)
[SEQ ID NO: 90]
5' CUGUCGGAGACUACdUCGUCGAGdUAGAAAUAGGUCCdCCUdCC 3', wherein C, U, G, A, are ribonucleotides, and
dG, dT, dC, dA and dU are 2'-deoxyribonucleotides.

In a sixth embodiment of the first aspect which is also an embodiment of the first, second, third, fourth and fifth embodiment of the first aspect, the central stretch of nucleotides comprises a nucleotide sequence of

[SEQ ID NO: 119]
5' CUGUCGGAGACUACUCGUCGAGUAGAAAUAGGUCCdCCUCC 3'
or

[SEQ ID NO: 123)
5' CUGUCGGAGACUACUCGUCGAGUAGAAAUAGGUCCdCCUdCC 3'
or

[SEQ ID NO: 131]
5' CUGUCGGAGACUACUCGUCGAGdUAGAAAUAGGUCCdCCUCC 3'.

In a seventh embodiment of the first aspect which is also an embodiment of the first, second, third and fourth embodiment of the first aspect, the central stretch of nucleotides consists of ribonucleotides and 2'-deoxyribonucleotides.

In an eight embodiment of the first aspect which is also an embodiment of the first, second, third and fourth embodiment of the first aspect, the central stretch of nucleotides consists of 2'-ribonucleotides.

In a ninth embodiment of the first aspect which is also an embodiment of the first, second, third, fourth, fifth, sixth, seventh and eighth embodiment of the first aspect, the nucleic acid molecule comprises in 5'->3' direction a first terminal stretch of nucleotides, the central stretch of nucleotides and a second terminal stretch of nucleotides, wherein
  the first terminal stretch of nucleotides comprises four to seven nucleotides, and
  the second terminal stretch of nucleotides comprises four to seven nucleotides, preferably
  the first terminal stretch of nucleotides comprises five to seven nucleotides, and
  the second terminal stretch of nucleotides comprises five to seven nucleotides.

In a tenth embodiment of the first aspect which is also an embodiment of the ninth embodiment of the first aspect,
the first terminal stretch of nucleotides comprises five nucleotides, and
the second terminal stretch of nucleotides comprises five nucleotides.

In an eleventh embodiment of the first aspect which is also an embodiment of the ninth and the tenth embodiment of the first aspect, the first terminal stretch of nucleotides comprises a nucleotide sequence of 5' $Z_1Z_2Z_3SZ_4WZ_5$ 3' and the second terminal stretch of nucleotides comprises a nucleotide sequence of 5' $Z_6Z_7Z_8Z_9Z_{10}Z_{11}Z_{12}$ 3',
wherein S, W, V, B, and K are ribonucleotides, and
$Z_1$ is S or absent, $Z_2$ is V or absent, $Z_3$ is B or absent, $Z_4$ is V or dG, $Z_5$ is G or dG, $Z_6$ is Y or dC, $Z_7$ is W or dA, $Z_8$ is B or dC, $Z_9$ is S or dG, $Z_{10}$ is S or dG or absent, $Z_{11}$ is B or absent, $Z_{12}$ is K or absent, and
dG, dC and dA are 2'-deoxyribonucleotides.

In a twelfth embodiment of the first aspect which is also an embodiment of the eleventh embodiment of the first aspect,
a) $Z_1$ is S, $Z_2$ is V, $Z_3$ is B, $Z_{10}$ is S or dG, $Z_{11}$ is B, $Z_{12}$ is K;
b) $Z_1$ is absent, $Z_2$ is V, $Z_3$ is B, $Z_{10}$ is S or dG, $Z_{11}$ is B, $Z_{12}$ is K;
c) $Z_1$ is S, $Z_2$ is V, $Z_3$ is B, $Z_{10}$ is S or dG, $Z_{11}$ is B, $Z_{12}$ is absent;
d) $Z_1$ is absent, $Z_2$ is V, $Z_3$ is B, $Z_{10}$ is S or dG, $Z_{11}$ is B, $Z_{12}$ is absent;
e) $Z_1$ is absent, $Z_2$ is absent, $Z_3$ is B, $Z_{10}$ is S or dG, $Z_{11}$ is B, $Z_{12}$ is absent;
f) $Z_1$ is absent, $Z_2$ is V, $Z_3$ is B, $Z_{10}$ is S or dG, $Z_{11}$ is absent, $Z_{12}$ is absent;
g) $Z_1$ is absent, $Z_2$ is absent, $Z_3$ is B, $Z_{10}$ is S or dG, $Z_{11}$ is absent, $Z_{12}$ is absent;
h) $Z_1$ is absent, $Z_2$ is absent, $Z_3$ is absent, $Z_{10}$ is S or dG, $Z_{11}$ is absent, $Z_{12}$ is absent;
i) $Z_1$ is absent, $Z_2$ is absent, $Z_3$ is B, $Z_{10}$ is absent, $Z_{11}$ is absent, $Z_{12}$ is absent; or
j) $Z_1$ is absent, $Z_2$ is absent, $Z_3$ is absent, $Z_{10}$ is absent, $Z_{11}$ is absent, $Z_{12}$ is absent.

In a 13th embodiment of the first aspect which is also an embodiment of the ninth, eleventh and twelfth embodiment of the first aspect,
the first terminal stretch of nucleotides comprises a nucleotide sequence of 5' CACCGUG 3' and the second terminal stretch of nucleotides comprises a nucleotide sequence of 5' CACGGUG 3'; or
the first terminal stretch of nucleotides comprises a nucleotide sequence of 5' GGCCGUG 3' and the second terminal stretch of nucleotides comprises a nucleotide sequence of 5' CACGGCU 3'; or
the first terminal stretch of nucleotides comprises a nucleotide sequence of 5' GUCAUG 3' and the second terminal stretch of nucleotides comprises a nucleotide sequence of 5' CACGGC 3'; or
the first terminal stretch of nucleotides comprises a nucleotide sequence of 5' GCCAUG 3' and the second terminal stretch of nucleotides comprises a nucleotide sequence of 5' CAUGGC 3'; or
the first terminal stretch of nucleotides comprises a nucleotide sequence of 5' GCCGUG 3' and the second terminal stretch of nucleotides comprises a nucleotide sequence of 5' CACGGC 3'; or
the first terminal stretch of nucleotides comprises a nucleotide sequence of 5' CCCGUG 3' and the second terminal stretch of nucleotides comprises a nucleotide sequence of 5' CACGGG 3'.

In a 14th embodiment of the first aspect which is also an embodiment of the ninth, tenth, eleventh and twelfth embodiment of the first aspect,
the first terminal stretch of nucleotides comprises a nucleotide sequence of 5' $CCZ_4UZ_5$ 3' and the second terminal stretch of nucleotides comprises a nucleotide sequence of 5' $Z_6Z_7Z_8Z_9Z_{10}$ 3', or
wherein C, G, A and U are ribonucleotides, and
$Z_4$ is G or dG, $Z_5$ is G or dG, $Z_6$ is C or dC, $Z_7$ is A or dA, $Z_8$ is C or dC, $Z_9$ is G or dG, $Z_{10}$ is G or dG,
dC, dG and dA are 2'-deoxyribonucleotides.

In a 15th embodiment of the first aspect which is also an embodiment of the ninth, tenth, eleventh, twelfth and 14th embodiment of the first aspect,
a) the first terminal stretch of nucleotides comprises a nucleotide sequence of 5' CCGUG 3' and the second terminal stretch of nucleotides comprises a nucleotide sequence of 5' CACGG 3'; or
b) the first terminal stretch of nucleotides comprises a nucleotide sequence of 5' CCdGUG 3' and the second terminal stretch of nucleotides comprises a nucleotide sequence of 5' CACGG 3'; or
c) the first terminal stretch of nucleotides comprises a nucleotide sequence of 5' CCGUdG 3' and the second terminal stretch of nucleotides comprises a nucleotide sequence of 5' CACGG 3'; or
d) the first terminal stretch of nucleotides comprises a nucleotide sequence of 5' CCGUG 3' and the second terminal stretch of nucleotides comprises a nucleotide sequence of 5' dCACGG 3'; or
e) the first terminal stretch of nucleotides comprises a nucleotide sequence of 5' CCGUG 3' and the second terminal stretch of nucleotides comprises a nucleotide sequence of 5' CdACGG 3'; or
f) the first terminal stretch of nucleotides comprises a nucleotide sequence of 5' CCGUG 3' and the second terminal stretch of nucleotides comprises a nucleotide sequence of 5' CAdCGG 3'; or
g) the first terminal stretch of nucleotides comprises a nucleotide sequence of 5' CCGUG 3' and the second terminal stretch of nucleotides comprises a nucleotide sequence of 5' CACdGG 3'; or
h) the first terminal stretch of nucleotides comprises a nucleotide sequence of 5' CCGUG 3' and the second terminal stretch of nucleotides comprises a nucleotide sequence of 5' CACGdG 3'; wherein
preferably the first terminal stretch of nucleotides comprises a nucleotide sequence of 5' CCGUG 3' and the second terminal stretch of nucleotides comprises a nucleotide sequence of 5' CACGG 3'.

In a 16th embodiment of the first aspect which is also an embodiment of the ninth, tenth, eleventh, twelfth and 14th embodiment of the first aspect,
a) the first terminal stretch of nucleotides comprises a nucleotide sequence of 5' GCGUG 3' and the second terminal stretch of nucleotides comprises a nucleotide sequence of 5' CACGC 3'; or
b) the first terminal stretch of nucleotides comprises a nucleotide sequence of 5' GGGUG 3' and the second terminal stretch of nucleotides comprises a nucleotide sequence of 5' CACCC 3'; or
c) the first terminal stretch of nucleotides comprises a nucleotide sequence of 5' GCCUG 3' and the second terminal stretch of nucleotides comprises a nucleotide sequence of 5' CAGGC 3'.

In a 17th embodiment of the first aspect which is also an embodiment of the ninth, eleventh and twelfth embodiment of the first aspect, the first terminal stretch of nucleotides comprises a nucleotide sequence of 5' CGUG 3' and the second terminal stretch of nucleotides comprises a nucleotide sequence of 5' CACG 3'; or the first terminal stretch of nucleotides comprises a nucleotide sequence of 5' CGUG 3' and the second terminal stretch of nucleotides comprises a nucleotide sequence of 5' UACG 3'; or the first terminal stretch of nucleotides comprises a nucleotide sequence of 5' GCAG 3' and the second terminal stretch of nucleotides comprises a nucleotide sequence of 5' CUGC 3'.

In an 18th embodiment of the first aspect which is also an embodiment of the first, second, third, fourth, eighth, ninth, tenth, eleventh, twelfth, 13th, 14th, 15th, 16th and 17th embodiment of the first aspect, the nucleic acid molecule comprises a nucleotide sequence selected from the group of SEQ ID NO: 2, SEQ ID NO: 7, SEQ ID NO: 15, SEQ ID NO: 16, SEQ ID NO: 18, SEQ ID NO: 19, SEQ ID NO: 21, SEQ ID NO: 22, SEQ ID NO: 24, SEQ ID NO: 25, SEQ ID NO: 26 and SEQ ID NO: 88, or a nucleic acid molecule having an identity of at least 85% to the nucleic acid molecule comprising a nucleotide sequence selected from the group of SEQ ID NO: 2, SEQ ID NO: 7, SEQ ID NO: 15, SEQ ID NO: 16, SEQ ID NO: 18, SEQ ID NO: 19, SEQ ID NO: 21, SEQ ID NO: 22, SEQ ID NO: 24, SEQ ID NO: 25, SEQ ID NO: 26 and SEQ ID NO: 88, or a nucleic acid molecule which is homologous to the nucleic acid molecule comprising a nucleotide sequence selected from the group of SEQ ID NO: 2, SEQ ID NO: 7, SEQ ID NO: 15, SEQ ID NO: 16, SEQ ID NO: 18, SEQ ID NO: 19, SEQ ID NO: 21, SEQ ID NO: 22, SEQ ID NO: 24, SEQ ID NO: 25, SEQ ID NO: 26 and SEQ ID NO: 88, wherein the homology is at least 85%.

In a 19th embodiment of the first aspect which is also an embodiment of the first, second, third, fourth, fifth, sixth, seventh, ninth, tenth, eleventh, twelfth, 13th, 14th, 15th, 16th and 17th embodiment of the first aspect, the nucleic acid molecule comprises a nucleotide sequence selected from the group of SEQ ID NO: 33, SEQ ID NO: 45, SEQ ID NO: 47, SEQ ID NO: 54, SEQ ID NO: 124 and SEQ ID NO: 078 or a nucleic acid molecule having an identity of at least 85% to the nucleic acid molecule comprising a nucleotide sequence selected from the group of SEQ ID NO: 33, SEQ ID NO: 45, SEQ ID NO: 47, SEQ ID NO: 54, SEQ ID NO: 124 and SEQ ID NO: 078, or a nucleic acid molecule which is homologous to the nucleic acid molecule comprising a nucleotide sequence selected from the group of SEQ ID NO: 33, SEQ ID NO: 45, SEQ ID NO: 47, SEQ ID NO: 54, SEQ ID NO: 124 and SEQ ID NO: 078, wherein the homology is at least 85%.

In a 20th embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th and 20th embodiment of the first aspect, the nucleotides of or the nucleotides forming the nucleic acid molecule are L-nucleotides.

In a 21st embodiment of the first aspect which is also an embodiment of the first, second, third, fourth, fifth, sixth, seventh, eighth, ninth, tenth, eleventh, twelfth, 13th, 14th, 15th, 16th, 17th, 18th and 19th embodiment of the first aspect, the nucleic acid molecule is an L-nucleic acid molecule.

In a 22nd embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th and 21st embodiment of the first aspect, the nucleic acid molecule comprises at least one binding moiety which is capable of binding CGRP, wherein such binding moiety consists of L-nucleotides.

In a 23rd embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th, 21st and 22nd embodiment of the first aspect, the nucleic acid is an antagonist of an activity mediated by CGRP.

In a 24th embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th, 21st, 22nd and 23rd embodiment of the first aspect, the nucleic acid molecule comprises a modification group, wherein excretion rate of the nucleic acid molecule comprising the modification group from an organism is decreased compared to a nucleic acid not comprising the modification group.

In a 25th embodiment of the first aspect which is also an embodiment of the first, second, third, fourth, fifth, sixth, seventh, eighth, ninth, tenth, eleventh, twelfth, 13th, 14th, 15th, 16th, 17th, 18th, 19th, 20th, 21st, 22nd and 23rd embodiment of the first aspect, the nucleic acid molecule comprises a modification group, wherein the nucleic acid molecule comprising the modification group has an increased retention time in an organism compared to a nucleic acid molecule not comprising the modification group.

In a 26th embodiment of the first aspect which is also an embodiment of the 24th and the 25th embodiment of the first aspect, the modification group is selected from the group comprising biodegradable and non-biodegradable modifications, preferably the modification group is selected from the group comprising polyethylene glycol, linear polyethylene glycol, branched polyethylene glycol, hydroxyethyl starch, a peptide, a protein, a polysaccharide, a sterol, polyoxypropylene, polyoxyamidate and poly(2-hydroxyethyl)-L-glutamine.

In a 27th embodiment of the first aspect which is also an embodiment of the 26th embodiment of the first aspect, the modification group is a polyethylene glycol, preferably consisting of a linear polyethylene glycol or branched polyethylene glycol, wherein the molecular weight of the polyethylene glycol is preferably from about 20,000 to about 120,000 Da, more preferably from about 30,000 to about 80,000 Da and most preferably about 40,000 Da.

In a 28th embodiment of the first aspect which is also an embodiment of the 26th embodiment of the first aspect, the modification group is hydroxyethyl starch, wherein preferably the molecular weight of the hydroxyethyl starch is from about 50 to about 1000 kDa, more preferably from about 100 to about 700 kDa and most preferably from 200 to 500 kDa.

In a 29th embodiment of the first aspect which is also an embodiment of the 24th, 25th, 26th, 27th and 28th embodiment of the first aspect, the modification group is coupled to the nucleic acid molecule via a linker, whereby preferably the linker is a biodegradable linker.

In a 30th embodiment of the first aspect which is also an embodiment of the 24th, 25th, 26th, 27th and 28th embodiment of the first aspect, the modification group is coupled to the 5'-terminal nucleotide and/or the 3'-terminal nucleotide of the nucleic acid molecule and/or to a nucleotide of the nucleic acid molecule between the 5'-terminal nucleotide of the nucleic acid molecule and the 3'-terminal nucleotide of the nucleic acid molecule.

In a 31st embodiment of the first aspect which is also an embodiment of the 24th, 25th, 26th, 27th 28th, 29th and 30th embodiment of the first aspect, the organism is an animal or a human body, preferably a human body.

The problem underlying the present invention is solved in a second aspect, which is also the first embodiment of the second aspect, by a nucleic acid molecule according to the first, second, third, fourth, fifth, sixth, seventh, eighth, ninth, tenth, eleventh, twelfth, $13^{th}$, $14^{th}$, $15^{th}$ $16^{th}$, $17^{th}$, $18^{th}$ $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$ and $31^{st}$ embodiment of the first aspect, for use in a method for the treatment and/or prevention of a disease.

In a second embodiment of the second aspect which is also an embodiment of the first embodiment of the second aspect, the disease is selected from the group comprising migraine, different forms of headache, acute pain, chronic pain, tolerance to morphine-based analgesia, osteoarthritis, angiogenesis, autoimmune diseases, tumor growth and inflammatory diseases, whereby preferably the acute pain and chronic pain is of inflammatory and/or neuropathic origin.

The problem underlying the present invention is solved in a third aspect, which is also the first embodiment of the third aspect, by a pharmaceutical composition comprising a nucleic acid molecule according to the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$ and $31^{st}$ embodiment of the first aspect and optionally a further constituent, wherein the further constituent is selected from the group comprising a pharmaceutically acceptable excipient, a pharmaceutically acceptable carrier and a pharmaceutically active agent.

In a second embodiment of the third aspect which is also an embodiment of the first embodiment of the third aspect the pharmaceutical composition comprises a nucleic acid molecule according to the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$ and $31^{st}$ embodiment of the first aspect and a pharmaceutically acceptable carrier.

The problem underlying the present invention is solved in a fourth aspect, which is also the first embodiment of the fourth aspect, by the use of a nucleic acid molecule to the first, second, third, fourth, fifth, sixth, seventh, eighth, ninth, tenth, eleventh, twelfth, $13^{th}$, $14^{th}$, $16^{th}$, $17^{th}$, $18^{th}$, $19^{th}$, $20^{th}$, $21^{st}$, $22^{nd}$, $23^{rd}$, $15^{th}$, $24^{th}$, $25^{th}$, $26^{th}$, $27^{th}$, $28^{th}$, $29^{th}$, $30^{th}$ and $31^{st}$ embodiment of the first aspect for the manufacture of a medicament.

In a second embodiment of the fourth aspect which is also an embodiment of the first embodiment of the fourth aspect the medicament is for use in human medicine or for use in veterinary medicine.

In a third embodiment of the fourth aspect which is also an embodiment of the first and the second embodiment of the fourth aspect the medicament is for the treatment and/or prevention of migraine, different forms of headache, acute pain, chronic pain, tolerance to morphine-based analgesia, osteoarthritis, angiogenesis, autoimmune diseases, tumor growth and inflammatory diseases, whereby preferably the acute pain and chronic pain is of inflammatory and/or neuropathic origin.

The problem underlying the present invention is solved in a fifth aspect, which is also the first embodiment of the fifth aspect, by the use of a nucleic acid molecule according to the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$ and $31^{st}$ embodiment of the first aspect, for the manufacture of a diagnostic means.

The problem underlying the present invention is solved in a sixth aspect, which is also the first embodiment of the sixth aspect, by a complex comprising a nucleic acid molecule according to the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$ and $31^{st}$ embodiment of the first aspect and CGRP, wherein preferably the complex is a crystalline complex.

The problem underlying the present invention is solved in a seventh aspect, which is also the first embodiment of the seventh aspect, by the use of a nucleic acid molecule according to the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$ and $31^{st}$ embodiment of the first aspect for the detection of CGRP.

The problem underlying the present invention is solved in an eighth aspect, which is also the first embodiment of the eighth aspect, by a method for the screening of an antagonist of an activity mediated by CGRP comprising the following steps:
   providing a candidate antagonist of the activity mediated by CGRP,
   providing a nucleic acid molecule of the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$$30^{th}$ and $31^{st}$ embodiment of the first aspect,
   providing a test system which provides a signal in the presence of an antagonist of the activity mediated by CGRP, and
   determining whether the candidate antagonist of the activity mediated by CGRP is an antagonist of the activity mediated by CGRP.

The problem underlying the present invention is solved in a ninth aspect, which is also the first embodiment of the ninth aspect, by a kit for the detection of CGRP comprising a nucleic acid molecule according to the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$ and $31^{st}$ embodiment of the first aspect and at least an instruction leaflet or a reaction vessel.

The problem underlying the present invention is solved in a tenth aspect, which is also the first embodiment of the tenth aspect, by a method for the detection of a nucleic acid molecule of the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$ and $31^{st}$ embodiment of the first aspect in a sample, wherein the method comprises the steps of:
   a) providing a capture probe, wherein the capture probe is at least partially complementary to a first part of the nucleic acid molecule of the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$ and $31^{st}$ embodiment of the first aspect, and a detection probe, wherein the detection probe is at least partially complementary to a second part of the nucleic acid molecule of the first, second, third, fourth, fifth, sixth, seventh, eighth, ninth, tenth, eleventh, twelfth, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$, $25^{th}$, $26^{th}$, $27^{th}$, $28^{th}$, $29^{th}$, $30^{th}$ and $31^{st}$ embodiment of the first aspect, or, alternatively, the capture probe is at least partially complementary to a second part of the nucleic acid molecule of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$ and 31$^{st}$ embodiment of the first aspect and the detection probe is at least partially complementary to the first part of the nucleic acid molecule of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$ and 31$^{st}$ embodiment of the first aspect;

b) adding the capture probe and the detection probe separately or combined to a sample containing the nucleic acid molecule or presumed to contain the nucleic acid molecule of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$ and 31$^{st}$ embodiment of the first aspect;

c) allowing the capture probe and the detection probe to react either simultaneously or in any order sequentially with the nucleic acid molecule of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$ and 31$^{st}$ embodiment of the first aspect or part thereof;

d) optionally detecting whether or not the capture probe is hybridized to the nucleic acid molecule of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$ and 31$^{st}$ embodiment of the first aspect provided in step a); and e) detecting a complex formed in step c) consisting of the nucleic acid molecule of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$ and 31$^{st}$ embodiment of the first aspect and the capture probe and the detection probe.

In a second embodiment of the tenth aspect which is also an embodiment of the first embodiment of the tenth aspect, the detection probe comprises a detection means, and/or wherein the capture probe is immobilized to a support, preferably a solid support.

In a third embodiment of the tenth aspect which is also an embodiment of the first and the second embodiment of the tenth aspect, any detection probe which is not part of the complex formed in step c) is removed from the reaction so that in step e) only a detection probe which is part of the complex, is detected.

In a fourth embodiment of the tenth aspect which is also an embodiment of the first, the second and the third embodiment of the tenth aspect, step e) comprises the step of comparing the signal generated by the detection means when the capture probe and the detection probe are hybridized in the presence of the nucleic acid molecule as defined in any one of claims 1 to 32 or part thereof, and in the absence of said nucleic acid molecule or part thereof In a 32$^{nd}$ embodiment of the first aspect which is also an embodiment of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$ and 31$^{st}$ embodiment of the first aspect, and which is also a second embodiment of the second aspect which is also an embodiment of the first embodiment of the second aspect, the CGRP is human CGRP, mouse CGRP, rat CGRP or CGRP from *maca mulatta*, preferably CGRP is human CGRP.

In a 33$^{rd}$ embodiment of the first aspect which is also an embodiment of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$ and 32$^{nd}$ embodiment of the first aspect, and which is also a third embodiment of the second aspect which is also an embodiment of the first and the second embodiment of the second aspect, the CGRP is α-CGRP or β-CGRP, preferably human α-CGRP, human α-CGRP or rat α-CGRP.

In a 34$^{th}$ embodiment of the first aspect which is also an embodiment of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$ and 33$^{rd}$ embodiment of the first aspect, and which is also a fourth embodiment of the second aspect which is also an embodiment of the first, second and third embodiment of the second aspect, the nucleic acid molecule has a binding affinity to human α-CGRP, expressed as $K_D$, of 10 nM or below, preferably of 1 nM or below, and more preferably of 100 pM or below.

In a 35$^{th}$ embodiment of the first aspect which is also an embodiment of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$ and 34$^{th}$ embodiment of the first aspect, and which is also a fifth embodiment of the second aspect which is also an embodiment of the first, second, third and fourth embodiment of the second aspect, the nucleic acid molecule has a binding affinity to human α-CGRP, expressed as IC50, of 10 nM or below, preferably of 1 nM or below, and more preferably of 100 pM or below.

In a 36$^{th}$ embodiment of the first aspect which is also an embodiment of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$ and 35$^{th}$ embodiment of the first aspect, and which is also a sixth embodiment of the second aspect which is also an embodiment of the first, second, third, fourth and fifth embodiment of the second aspect, the nucleic acid molecule has a binding affinity to human amylin, expressed as $K_D$, of 100 nM or more, preferably of 500 nM or more, and more preferably of 1000 nM or more.

In a 37$^{th}$ embodiment of the first aspect which is also an embodiment of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$ and 36$^{th}$ embodiment of the first aspect, and which is also a seventh embodiment of the second aspect which is also an embodiment of the first, second, third, fourth, fifth and sixth embodiment of the second aspect, the nucleic acid molecule has a binding affinity to human amylin, expressed as IC50, of 100 nM or more, preferably of 500 nM or more, and more preferably of 1000 nM or more.

In a 38$^{th}$ embodiment of the first aspect which is also an embodiment of the first, second, third, fourth, fifth, sixth, seventh, eighth, ninth, tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$, 33$^{rd}$, 34$^{th}$, 35$^{th}$, 36$^{th}$ and 37th embodiment of the first aspect, and which is also an eighth embodiment of the second aspect which is also an embodiment of the first, second, third, fourth, fifth, sixth and seventh embodiment of the second aspect, the nucleic acid molecule has a binding affinity to human α-CGRP, expressed as $K_D$, of 10 nM or below, preferably of 1 nM or below, and more preferably of 100 pM or below, wherein the nucleic acid molecule has a binding affinity human amylin, expressed as $K_D$, of 100 nM or more, preferably of 500 nM or more, and more preferably of 1000 nM or more, and/or the nucleic acid molecule has a binding affinity to human α-CGRP, expressed as IC50, of 10 nM or below, preferably of 1 nM or below, and more preferably of 100 pM or below, wherein the nucleic acid molecule has a binding affinity to human amylin, expressed as IC50, of 100 nM or more, preferably of 500 nM or more, and more preferably of 1000 nM or more.

While not wishing to be bound by any theory, the present inventors have surprisingly found that the nucleic acid molecule according to the present invention binds specifically and with high affinity to CGRP, thereby inhibiting the binding of CGRP to its CGRP receptor without cross-reacting to amylin. Therefore the nucleic acid molecule according to the present invention has the potential to be used for the treatment of CGRP-related disorders and diseases, such as pain-related disorders, including migraine and other diseases. Furthermore, the instant inventors have found that the nucleic acid molecule according to the present invention is suitable to block the interaction of CGRP with the CGRP receptor. Insofar, the nucleic acid molecule according to the present invention is an antagonist of the CGRP and/or an antagonist of the CGRP-CGRP receptor system.

An antagonist to CGRP is a molecule that binds to CGRP—such as the nucleic acid molecule according to the present invention—and antagonizes an activity mediated by CGRP to the CGRP receptor in an in vitro assay as described in the Example 5. One activity mediated by CGRP according to present invention is the induction of cAMP production in human neuroblastoma cells as described in the Example 5.

As to the various diseases, conditions and disorders which may be treated or prevented by using the nucleic acid molecule according to the present invention or a composition, preferably a pharmaceutical composition comprising the nucleic acid molecule according to the present invention, it has to be acknowledged that such diseases, conditions and disorders are those which are described herein, including and in particular those described and set forth in the introductory part of the instant application. Insofar, the respective passages of the specification and the introductory part of the specification form an integral part of the present disclosure teaching the suitability of the nucleic acid molecule of the present invention for the prevention and treatment, respectively, for said diseases, conditions, and disorders.

As used herein the term CGRP refers to any CGRP including, but not limited to, mammalian CGRP. Preferably, the mammalian CGRP is selected from the group comprising human CGRP, monkey CGRP, rat CGRP, mouse CGRP, pig CGRP, sheep CGRP, dog CGRP. More preferably the CGRP is human CGRP. As used herein the term CGRP refers to αCGRP and β-CGRP. Preferably α-CGRP is selected from the group comprising human α-CGRP, monkey α-CGRP, rat α-CGRP, mouse α-CGRP, pig α-CGRP, sheep α-CGRP, dog α-CGRP. More preferably the α-CGRP is human α-CGRP Sequence alignment (see FIG. 8B) demonstrates the following percentages of identical amino acids of human α-CGRP with α-CGRP from:

| | |
|---|---|
| *Macaca mulatta* (rhesus monkey) | 100% |
| *Rattus norvegicus* (rat) | 89% |
| *Mus musculus* (mouse) | 89% |
| *Sus scrofa* (pig) | 86% |
| *Ovis aries* (Sheep) | 89% |
| *Canis familiaris* (dog) | 92% |

As used herein the term CGRP receptor refers to any cell surface protein that transmits a CGRP signal into the cells by inducing a signal transduction event. CGRP receptors include, but are not limited to, mammalian CGRP receptors. Preferably, the mammalian CGRP receptor is selected from the group comprising human CGRP receptor, monkey CGRP receptor, rat CGRP receptor, mouse CGRP receptor, pig CGRP receptor, sheep CGRP receptor, dog CGRP receptor. More preferably the CGRP receptor is the human CGRP receptor.

Additionally, a nucleic molecule according to the present invention is preferred if the physiological effect of the CGRP-CGRP receptor axis is related to higher plasma levels of CGRP.

As a consequence of high sequence homology between CGRP and amylin (see alignment FIG. 9) previously identified CGRP-binding Spiegelmers (see WO2003/04372) showed cross-reactivity to amylin (example 7, FIG. 10). Thus, the present invention is based on the surprising finding that it is possible to generate a nucleic acid molecule binding with high affinity to human CGRP, thereby inhibiting and antagonizing the effects of CGRP, in particular the effects of CGRP on its receptor and that is highly specific in terms of binding to human CGRP while not showing cross-reactivity for human amylin.

It is within the present invention that the nucleic acid according to the present invention is a nucleic acid molecule. Insofar the terms nucleic acid and nucleic acid molecule are used herein in a synonymous manner if not indicated to the contrary. Moreover, such nucleic acid(s) is/are preferably also referred to herein as the nucleic acid molecule(s) according to the present invention, the nucleic acid(s) according to the present invention, the inventive nucleic acid(s) or the inventive nucleic acid molecule(s).

The features of the nucleic acid according to the present invention as described herein can be realised in any aspect of the present invention where the nucleic acid is used, either alone or in any combination.

As outlined in more detail herein, the present inventors have identified a number of different CGRP binding nucleic acid molecules that specifically binds to CGRP, whereby the nucleic acid molecules can be characterised in terms of stretches of nucleotides which are also referred to herein as disclosed (see Example 1).

The CGRP binding nucleic acid molecules of the invention comprises three different stretches of nucleotides: a first terminal stretch of nucleotides, a central stretch of nucleotides and a second terminal stretch of nucleotides. In general, a CGRP binding nucleic acid molecule of the present invention comprise at the 5'-end and the 3'-end each one of the terminal stretches of nucleotides, i.e. the first terminal stretch of nucleotides and the second terminal stretch of nucleotides (also referred to as 5'-terminal stretch of nucleotides and 3'-terminal stretch of nucleotides). The first terminal stretch of nucleotides and the second terminal stretch of nucleotides can, in principle due to their base complementarity, hybridize to each other, whereby upon hybridization a double-stranded structure is formed. However, such hybridization is not necessarily realized in the molecule under physiological and/or nonphysiological conditions. The three stretches of nucleotides of a CGRP binding nucleic acid molecule of the invention—the first terminal stretch of nucleotides, the central stretch of nucleotides and second terminal stretch of nucleotides—are arranged to each other in 5'→3'-direction: the first terminal stretch of nucleotides—the central stretch of nucleotides—the second terminal stretch of nucleotides. Alternatively, the second terminal stretch of nucleotides, the central stretch of nucleotides and the terminal first stretch of nucleotides are arranged to each other in 5'→3'-direction.

The length of the central stretch of nucleotides of the nucleic acids according to the present invention is preferably 40.

The length of the first terminal stretch of nucleotides of the nucleic acids according to the present invention is between four and seven nucleotides, preferably between five and seven nucleotides, more preferably five nucleotides.

The length of the second terminal stretch of nucleotides of the nucleic acids according to the present invention is between four and seven nucleotides, preferably between five and seven nucleotides, more preferably five nucleotides.

The differences in the sequences of the defined boxes or stretches between the different CGRP binding nucleic acid molecules of the invention influence the binding affinity to CGRP. Based on binding analysis of the different CGRP binding nucleic acid molecules of the present invention the central stretch and the nucleotides forming the same are individually and more preferably in their entirety essential for the binding of the CGRP binding nucleic acid molecule to CGRP.

The terms 'stretch' and 'stretch of nucleotide' are used herein in a synonymous manner if not indicated to the contrary.

In a preferred embodiment the nucleic acid according to the present invention is a single nucleic acid molecule. In a further embodiment, the single nucleic acid molecule is present as a multitude of the single nucleic acid molecule or as a multitude of the single nucleic acid molecule species.

It will be acknowledged by the ones skilled in the art that the nucleic acid molecule in accordance with the invention preferably consists of nucleotides which are covalently linked to each other, preferably through phosphodiester links or linkages.

It is within the present invention that the nucleic acids according to the present invention comprise two or more stretches or part(s) thereof can, in principle, hybridise with each other. Upon such hybridisation a double-stranded structure is formed. It will be acknowledged by the ones skilled in the art that such hybridisation may or may not occur, particularly under in vitro and/or in vivo conditions. Also, in case of such hybridisation, it is not necessarily the case that the hybridisation occurs over the entire length of the two stretches where, at least based on the rules for base pairing, such hybridisation and thus formation of a double-stranded structure may, in principle, occur. As preferably used herein, a double-stranded structure is a part of a nucleic acid molecule or a structure formed by two or more separate strands or two spatially separated stretches of a single strand of a nucleic acid molecule, whereby at least one, preferably two or more base pairs exist which are base pairing preferably in accordance with the Watson-Crick base pairing rules. It will also be acknowledged by the one skilled in the art that other base pairing such as Hoogsten base pairing may exist in or form such double-stranded structure. It is also to be acknowledged that the feature that two stretches hybridize preferably indicates that such hybridization is assumed to happen due to base complementarity of the two stretches regardless of whether such hybridization actually occurs in vivo and/or in vitro. In connection with the present invention such stretches are the first terminal stretch of nucleotides and the second stretch of nucleotides which, in an embodiment, may hybridize as defined above.

In a preferred embodiment the term arrangement as used herein, means the order or sequence of structural or functional features or elements described herein in connection with the nucleic acid(s) of the invention disclosed herein.

It will be acknowledged by the person skilled in the art that the nucleic acid according to the present invention is capable of binding to CGRP. Without wishing to be bound by any theory, the present inventors assume that the CGRP binding results from a combination of three-dimensional structural traits or elements of the nucleic acid molecule of the invention, which are caused by orientation and folding patterns of the primary sequence of nucleotides forming such traits or elements, whereby preferably such traits or elements are the first terminal stretch of nucleotides, the central stretch of nucleotides and the second terminal stretch of nucleotides of CGRP binding nucleic acid molecules. It is evident that the individual trait or element may be formed by various different individual sequences the degree of variation of which may vary depending on the three-dimensional structure such element or trait has to form for mediating the binding of the nucleic acid molecule of the invention to CGRP. The overall binding characteristic of the claimed nucleic acid results from the interplay of the various elements and traits, respectively, which ultimately results in the interaction of the claimed nucleic acid with its target, i. e. CGRP. Again without being wished to be bound by any theory, the central stretch of nucleotides that is characteristic for CGRP binding nucleic acids is important for mediating the binding of the claimed nucleic acid molecules with CGRP. Accordingly, the nucleic acids according to the present invention are suitable for the interaction with CGRP. Also, it will be acknowledged by the person skilled in the art that the nucleic acid according to the present invention is an antagonists to CGRP. Because of this the nucleic acid according to the present invention is suitable for the treatment and prevention, respectively, of any disease or condition which is associated with or caused by CGRP. Such diseases and conditions may be taken from the prior art which establishes that CGRP is involved or associated with said diseases and conditions, respectively, and which is incorporated herein by reference providing the scientific rationale for the therapeutic use of the nucleic acids according to the invention.

The nucleic acid molecule according to the present invention shall also comprise a nucleic acid molecule which is essentially homologous to the particular nucleotide sequences disclosed herein. The term substantially homologous shall be understood such as the homology is at least 75%, preferably at least 85%, more preferably at least 90% and most preferably more that at least 95%, 96%, 97%, 98% or 99%.

The actual percentage of homologous nucleotides present in a nucleic acid molecule according to the present invention will depend on the total number of nucleotides present in the nucleic acid. The percent modification can be calculated based upon the total number of nucleotides present in the nucleic acid molecule.

The homology between two nucleic acid molecules can be determined as known to the person skilled in the art. More specifically, a sequence comparison algorithm may be used for calculating the percent sequence homology for the test sequence(s) relative to the reference sequence, based on the designated program parameters. The test sequence is preferably the sequence or nucleic acid molecule which is said to be homologous or to be tested whether it is homologous, and if so, to what extent, to a different nucleic acid molecule, whereby such different nucleic acid molecule is also referred to as the reference sequence. In an embodiment, the reference sequence is a nucleic acid molecule as described herein, preferably a nucleic acid molecule having a sequence according to any one SEQ ID NO: 2, SEQ ID NO: 7, SEQ ID NO: 15, SEQ ID NO: 16, SEQ ID NO: 18, SEQ ID NO: 19, SEQ ID NO: 21, SEQ ID NO: 22, SEQ ID NO: 24, SEQ ID NO: 25, SEQ ID NO: 26, SEQ ID NO: 88, SEQ ID NO: 33, SEQ ID NO: 45, SEQ ID NO: 47, SEQ ID NO: 54, SEQ ID NO: 124 and SEQ ID NO: 078. Optimal alignment of sequences for comparison can be conducted, e.g., by the local homology algorithm of Smith & Waterman (Smith & Waterman, 1981) by the homology alignment algorithm of Needleman & Wunsch (Needleman & Wunsch, 1970) by the search for similarity method of Pearson & Lipman (Pearson & Lipman, 1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity is the algorithm used in the basic local alignment search tool (hereinafter "BLAST"), see, e.g. Altschul et al (Altschul et al. 1990 and Altschul et al, 1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al (McGinnis et al., 2004).

The nucleic acid molecule according to the present invention shall also comprise a nucleic acid molecule which has a certain degree of identity relative to the nucleic acid molecule(s) of the present invention disclosed herein and defined by its/their nucleotide sequence. More preferably, the instant invention also comprises those nucleic acid molecules which have an identity of at least 75%, preferably at least 85%, more preferably at least 90% and most preferably more than at least 95%, 96%, 97%, 98% or 99% relative to the nucleic acid molecule of the present invention defined by their nucleotide sequence or a part thereof.

The term inventive nucleic acid or nucleic acid molecule according to the present invention shall also comprise a nucleic acid molecule comprising a nucleic acid sequence disclosed herein or part thereof, such as, e.g., a metabolite or derivative of the nucleic acid according to the present invention, preferably to the extent that the nucleic acid molecule or said parts are involved in the or capable of binding to CGRP. Such a nucleic acid molecule may be derived from the ones disclosed herein by, e.g., truncation. Truncation may be related to either one or both of the ends of a nucleic acid molecule of the present invention as disclosed herein. Also, truncation may be related to the inner sequence of nucleotides, i.e. it may be related to one or several of the nucleotide(s) between the 5'terminal nucleotide and the 3' terminal nucleotide, respectively. Moreover, truncation shall comprise the deletion of as little as a single nucleotide from the sequence of a nucleic acid molecule of the present invention disclosed herein. Truncation may also be related to more than one stretch of nucleotides of the nucleic acid molecule of the present invention, whereby the stretch of nucleotides can be as little as one nucleotide long. The binding of a nucleic acid molecule according to the present invention can be determined by the ones skilled in the art using routine experiments or by using or adopting a method as described herein, preferably as described herein in the example part.

The nucleic acid molecule according to the present invention may be either a D-nucleic acid molecule or an L-nucleic acid molecule. Preferably, the nucleic acid molecule according to the present invention is an L-nucleic acid molecule, more preferably, the nucleic acid molecule according to the present invention is a Spiegelmer.

It is also within the present invention that, in an embodiment, each and any of the nucleic acid molecules described herein in their entirety in terms of their nucleic acid sequence(s) are limited to the particular indicated nucleotide sequence(s). In other words, the terms "comprising" or "comprise(s)" shall be interpreted in such embodiment in the meaning of containing or consisting of.

It is also within the present invention that the nucleic acid according to the present invention is part of a longer nucleic acid whereby this longer nucleic acid comprises several parts whereby at least one such part is a nucleic acid, or a part thereof, according to the present invention. The other part(s) of these longer nucleic acid can be either one or several D-nucleic acid(s) or L-nucleic acid(s). Any combination may be used in connection with the present invention. These other part(s) of this longer nucleic acid can exhibit a function which is different from binding, preferably from binding to CGRP. One possible function is to allow interaction with other molecules, whereby such other molecules preferably are different from CGRP such as, e.g., for immobilization, cross-linking, detection or amplification. In a further embodiment of the present invention the nucleic acids according to the invention comprise, as individual or combined moieties, several of the nucleic acids of the present invention. Such nucleic acid comprising several of the nucleic acids of the present invention is also encompassed by the term longer nucleic acid.

An L-nucleic acid as used herein is a nucleic acid or nucleic acid molecule consisting of L-nucleotides, preferably consisting completely of L-nucleotides.

A D-nucleic acid as used herein is nucleic acid or nucleic acid molecule consisting of D-nucleotides, preferably consisting completely of D-nucleotides.

The terms nucleic acid and nucleic acid molecule are used herein in an interchangeable manner if not explicitly indicated to the contrary.

Also, if not indicated to the contrary, any nucleotide sequence is set forth herein in 5'→3' direction.

As preferably used herein any position of a nucleotide is determined or referred to relative to the 5' end of a sequence, a stretch or a substretch containing such nucleotide. Accordingly, a second nucleotide is the second nucleotide counted from the 5' end of the sequence, stretch and substretch, respectively. Also, in accordance therewith, a penultimate nucleotide is the second nucleotide counted from the 3' end of a sequence, stretch and substretch, respectively.

Irrespective of whether the nucleic acid molecule of the invention consists of D-nucleotides, L-nucleotides or a combination of both with the combination being, e.g., a random combination or a defined sequence of stretches consisting of at least one L-nucleotide and at least one D-nucleic acid, the nucleic acid may consist of desoxyribonucleotide(s), ribonucleotide(s) or combinations thereof.

It is also within the present invention that the nucleic acid molecule consists of both ribonucleotides and 2'deoxyribonucleotides. The 2'deoxyribonucleotides and ribonucleotides are shown in FIGS. 11A-B and 12. In order to distinguish between ribonucleotides and 2'deoxyribonucleotides in the sequences of the nucleic acid molecules according to the present invention the following reference code is used herein.

The nucleic acid molecule according to the present invention mainly consists of 2'deoxyribonucleotides, wherein dG is 2'deoxy-guanosine-5'-monophosphate, dC is 2'deoxy-cytidine-5'-monophosphate, dA is 2'deoxy-adenosine-5'-monophosphate, dT is 2'deoxy-thymidine-5'-monophosphate, and dU is 2'deoxy-uridine-5'-monophosphate.

The nucleic acid molecule according to the present invention mainly consists of ribonucleotides, wherein G is guanosine-5'-monophosphate, C is cytidine 5'-monophosphate, A is adenosine-5'-monophosphate, and U is uridine-5'monophosphate.

Designing the nucleic acid molecule of the invention as an L-nucleic acid molecule is advantageous for several reasons. L-nucleic acid molecules are enantiomers of naturally occurring nucleic acids. D-nucleic acid molecules, however, are not very stable in aqueous solutions and particularly in biological systems or biological samples due to the widespread presence of nucleases. Naturally occurring nucleases, particularly nucleases from animal cells are not capable of degrading L-nucleic acids. Because of this, the biological half-life of an L-nucleic acid molecule is significantly increased in such a system, including the animal and human body. Due to the lacking degradability of L-nucleic acid molecules no nuclease degradation products are generated and thus no side effects arising therefrom are observed in such a system including the animal and human body. This aspect distinguishes L-nucleic acid molecules from factually all other compounds which are used in the therapy of diseases and/or disorders involving the presence of CGRP or which are mediated by CGRP. An L-nucleic acid molecule which specifically binds to a target molecule through a mechanism different from Watson Crick base pairing, or an aptamer which consists partially or completely of L-nucleotides, particularly with those parts of the aptamer being involved in the binding of the aptamer to the target molecule, is also called a Spiegelmer. Aptamers and Spiegelmers as such are known to a person skilled in the art and are, among others, described in 'The Aptamer Handbook' (eds. Klussmann, 2006).

It is also within the present invention that the nucleic acid molecule of the invention, regardless whether it is present as D-nucleic acid, L-nucleic acid or D,L-nucleic acid or whether it is DNA or RNA, may be present as single stranded or double stranded nucleic acid. Typically, the nucleic acid molecule of the invention is a single stranded nucleic acid molecule which exhibits defined secondary structures due to the primary sequence and may thus also form tertiary structures. The nucleic acid molecule of the invention, however, may also be double stranded in the meaning that two strands which are complementary or partially complementary to each other are hybridised to each other.

The nucleic acid molecule of the invention may be modified. Such modification may be related to the single nucleotide of the nucleic acid molecule and is well known in the art. Examples for such modification are described by, among others, Venkatesan et al. (Venkatesan, Kim et al. 2003) and Kusser (Kusser 2000). Such modification can be a H atom, a F atom or O—CH$_3$ group or NH$_2$-group at the 2' position of one, several of all of the individual nucleotides of which the nucleic acid molecule consists. Also, the nucleic acid molecule according to the present invention can comprise at least one LNA nucleotide. In an embodiment the nucleic acid molecule according to the present invention consists of LNA nucleotides.

In an embodiment, the nucleic acid molecule according to the present invention may be a multipartite nucleic acid molecule. A multipartite nucleic acid molecule as used herein is a nucleic acid molecule which consists of at least two separate nucleic acid strands. These at least two nucleic acid strands form a functional unit whereby the functional unit is a ligand to a target molecule and, preferably, an antagonist to the target molecule, in the instant case of CGRP. The at least two nucleic acid strands may be derived from any of the nucleic acid molecule of the invention by either cleaving a nucleic acid molecule of the invention to generate at least two strands or by synthesising one nucleic acid molecule corresponding to a first part of the full-length nucleic acid molecule of the invention and another nucleic acid molecule corresponding to another part of the full-length nucleic acid molecule of the invention. Depending on the number of parts forming the full-length nucleic acid molecules the corresponding number of parts having the required nucleotide sequence will be synthesized It is to be acknowledged that both the cleavage approach and the synthesis approach may be applied to generate a multipartite nucleic acid molecule where there are more than two strands as exemplified above. In other words, the at least two separate nucleic acid strands are typically different from two strands being complementary and hybridising to each other although a certain extent of complementarity between said at least two separate nucleic acid strands may exist and whereby such complementarity may result in the hybridisation of said separate strands.

Finally it is also within the present invention that a fully closed, i.e. circular structure for the nucleic acid molecule according to the present invention is realized, i.e. that the nucleic acid molecule according to the present invention is closed in an embodiment, preferably through a covalent linkage, whereby more preferably such covalent linkage is made between the 5' end and the 3' end of the nucleic acid sequences as disclosed herein or any derivative thereof.

A possibility to determine the binding constants of the nucleic acid molecule according to the present invention is the use of the methods as described in example 4 herein, which confirms the above finding that the nucleic acid according to the present invention exhibits a favourable $K_D$ value range. An appropriate measure in order to express the intensity of the binding between the individual nucleic acid molecule and the target which is in the present case CGRP is the so-called $K_D$ value which as such as well as the method for its determination are known to the one skilled in the art.

Preferably, the $K_D$ value shown by the nucleic acid according to the present invention is below 1 µM. A $K_D$ value of about 1 µM is said to be characteristic for a non-specific binding of a nucleic acid to a target. As will be acknowledged by the ones skilled in the art, the $K_D$ value of a group of compounds such as various embodiments of the nucleic acid molecule according to the present invention is within a certain range. The above-mentioned $K_D$ of about 1 µM is a preferred upper limit for the $K_D$ value. The lower limit for the $K_D$ of target binding nucleic acids such as the one of the nucleic acid molecule of the invention can be as little as about 10 picomolar or can be higher. It is within the present invention that the $K_D$ values of individual nucleic acid molecule of the present invention binding to CGRP is preferably within this range. Preferred ranges of $K_D$ values can be defined by choosing any first number within this range and any second number within this range. Preferred upper $K_D$ values are 250 nM and 100 nM, preferred lower $K_D$ values are 50 nM, 10 nM, 1 nM, 100 pM and 10 pM. The more preferred upper $K_D$ value is 10 nM, the more preferred lower $K_D$ value is 100 pM.

Preferably CGRP is human alpha-CGRP, wherein the nucleic acid molecule has a binding affinity to human alpha-CGRP, expressed as $K_D$, of 10 nM or below, preferably of 1 nM or below, and more preferably of 100 pM or below.

As shown in Example 7 for the nucleic acid molecule according to the present invention no binding to human amylin could be detected by surface plasmon resonance measurement. Preferably the nucleic acid molecule according to the present invention has a binding affinity to human amylin, expressed as $K_D$, of 100 nM or more, preferably of 500 nM or more, and more preferably of 1000 nM or more.

In addition to the binding properties of the nucleic acid molecule according to the present invention, the nucleic acid molecule according to the present invention inhibits the function of the respective target molecule which is in the present case CGRP. The inhibition of the function of CGRP—for instance the stimulation of the respective receptors as described previously—is achieved by binding of a nucleic acid molecule according to the present invention to CGRP and forming a complex of a nucleic acid molecule according to the present invention and CGRP. Such complex of a nucleic acid molecule and CGRP cannot stimulate the receptors that normally are stimulated by CGRP, i.e. CGRP which is not present in a complex with a nucleic acid molecule of the invention. Accordingly, the inhibition of receptor function by a nucleic acid molecule according to the present invention is independent from the respective receptor that can be stimulated by CGRP but results from preventing the stimulation of the receptor by CGRP by the nucleic acid molecule according to the present invention.

A possibility to determine the inhibitory constant of the nucleic acid molecule according to the present invention is the use of the methods as described in example 5 which confirms the above finding that the nucleic acid molecule according to the present invention exhibit a favourable inhibitory constant which allows the use of said nucleic acid molecule in a therapeutic treatment scheme. An appropriate measure in order to express the intensity of the inhibitory effect of the individual nucleic acid molecule on interaction of the target which is in the present case CGRP, and the respective receptor, is the so-called half maximal inhibitory concentration (abbr. $IC_{50}$) which as such as well as the method for its determination are known to the one skilled in the art.

Preferably, the $IC_{50}$ value shown by the nucleic acid molecule according to the present invention is below 1 μM. An $IC_{50}$ value of about 1 μM is said to be characteristic for a non-specific inhibition of target functions, preferably the inhibition of the activation of the target receptor by the target, by a nucleic acid molecule of the invention. As will be acknowledged by the ones skilled in the art, the $IC_{50}$ value of a group of compounds such as various embodiments of the nucleic acid molecule according to the present invention is within a certain range. The above-mentioned $IC_{50}$ of about 1 μM is a preferred upper limit for the $IC_{50}$ value. The lower limit for the $IC_{50}$ of target binding nucleic acid molecules can be as little as about 10 picomolar or can be higher. It is within the present invention that the $IC_{50}$ values of individual nucleic acids binding to CGRP is preferably within this range. Preferred ranges can be defined by choosing any first number within this range and any second number within this range. Preferred upper $IC_{50}$ values are 250 nM and 100 nM, preferred lower $IC_{50}$ values are 50 nM, 10 nM, 1 nM, 100 pM and 10 pM. The more preferred upper $IC_{50}$ value is 5 nM, the more preferred lower $IC_{50}$ value is 100 pM.

In a preferred embodiment CGRP is human alpha-CGRP, wherein the nucleic acid molecule has a binding affinity to human alpha-CGRP, expressed as IC50, of 10 nM or below, preferably of 1 nM or below, and more preferably of 100 pM or below.

As shown in Example 7 for the nucleic acid molecule according to the present invention an IC50>1000 nM for human amylin and an IC50>100 nM for rat amylin was measured. In a preferred embodiment the nucleic acid according to the present invention molecule has a binding affinity to human amylin, expressed as IC50, of 100 nM or more, preferably of 500 nM or more, and more preferably of 1000 nM or more.

Preferably the nucleic acid molecule has a binding affinity to human alpha-CGRP, expressed as $K_D$, of 10 nM or below, preferably of 1 nM or below, and more preferably of 100 pM or below, wherein the nucleic acid molecule has a binding affinity human amylin, expressed as $K_D$, of 100 nM or more, preferably of 500 nM or more, and more preferably of 1000 nM or more, and/or the nucleic acid molecule has a binding affinity to human alpha-CGRP, expressed as IC50, of 10 nM or below, preferably of 1 nM or below, and more preferably of 100 pM or below, wherein the nucleic acid molecule has a binding affinity to human amylin, expressed as IC50, of 100 nM or more, preferably of 500 nM or more, and more preferably of 1000 nM or more.

The nucleic acid molecules according to the present invention may have any length provided that they are still able to bind to the target molecule which is in the instant case CGRP. It will be acknowledged in the art that there are preferred lengths of the nucleic acids according to the present inventions. Typically, the length is between 15 and 120 nucleotides. It will be acknowledged by the ones skilled in the art that any integer between 15 and 120 is a possible length for the nucleic acids according to the present invention. More preferred ranges for the length of the nucleic acids according to the present invention are lengths of about 20 to 100 nucleotides, about 20 to 80 nucleotides, about 20 to 60 nucleotides, about 20 to 52 nucleotides and about 48 to 54 nucleotides.

It is within the present invention that the nucleic acid molecule comprises a moiety which preferably is a high molecular weight moiety and/or which preferably allows to modify the characteristics of the nucleic acid in terms of, among others, residence time in the animal body, preferably the human body. A particularly preferred embodiment of such modification is PEGylation and HESylation of the nucleic acid molecule according to the present invention. As used herein PEG stands for poly(ethylene glycole) and HES for hydroxyethyl starch. PEGylation as preferably used herein is the modification of a nucleic acid according to the present invention whereby such modification consists of a PEG moiety which is attached to a nucleic acid according to the present invention. HESylation as preferably used herein is the modification of a nucleic acid according to the present invention whereby such modification consists of a HES moiety which is attached to a nucleic acid according to the present invention. These modifications as well as the process of modifying a nucleic acid using such modifications, is described in European patent application EP 1 306 382, the disclosure of which is herewith incorporated herein by reference in its entirety.

In the case of PEG being such high molecular weight moiety the molecular weight is preferably about 20,000 to about 120,000 Da, more preferably from about 30,000 to about 80,000 Da and most preferably about 40,000 Da. In the case of HES being such high molecular weight moiety the molecular weight is preferably from about 50 to about 1000 kDa, more preferably from about 100 to about 700 kDa and most preferably from 200 to 500 kDa. HES exhibits a molar substitution of 0.1 to 1.5, more preferably of 1 to 1.5 and exhibits a substitution grade expressed as the C2/C6 ratio of approximately 0.1 to 15, preferably of approximately 3 to 10. The process of HES modification is, e.g., described in German patent application DE 1 2004 006 249.8 the disclosure of which is herewith incorporated herein by reference in its entirety.

The modification can, in principle, be made to the nucleic acid molecules of the present invention at any position thereof. Preferably such modification is made either to the 5'-terminal nucleotide, the 3'-terminal nucleotide and/or any nucleotide between the 5' nucleotide and the 3' nucleotide of the nucleic acid molecule.

The modification and preferably the PEG and/or HES moiety can be attached to the nucleic acid molecule of the present invention either directly or indirectly, preferably indirectly through a linker. It is also within the present invention that the nucleic acid molecule according to the present invention comprises one or more modifications, preferably one or more PEG and/or HES moiety. In an embodiment the individual linker molecule attaches more than one PEG moiety or HES moiety to a nucleic acid molecule according to the present invention. The linker used in connection with the present invention can itself be either linear or branched. This kind of linkers are known to the ones skilled in the art and are further described in patent applications WO2005/074993 and WO2003/035665.

In a preferred embodiment the linker is a biodegradable linker. The biodegradable linker allows to modify the characteristics of the nucleic acid according to the present invention in terms of, among other, residence time in an animal body, preferably in a human body, due to release of the modification from the nucleic acid according to the present invention. Usage of a biodegradable linker may allow a better control of the residence time of the nucleic acid according to the present invention. A preferred embodiment of such biodegradable linker is a biodegradable linker as described in, but not limited to, international patent applications WO2006/052790, WO2008/034122, WO2004/092191 and WO2005/099768.

It is within the present invention that the modification or modification group is a biodegradable modification, whereby the biodegradable modification can be attached to the nucleic acid molecule of the present invention either directly or indirectly, preferably through a linker. The biodegradable modification allows to modify the characteristics of the nucleic acid according to the present invention in terms of, among other, residence time in an animal body, preferably in a human body, due to release or degradation of the modification from the nucleic acid according to the present invention. Usage of biodegradable modification may allow a better control of the residence time of the nucleic acid according to the present invention. A preferred embodiment of such biodegradable modification is biodegradable as described in, but not restricted to, international patent applications WO2002/065963, WO2003/070823, WO2004/113394 and WO2000/41647, preferably in WO2000/41647, page 18, line 4 to 24.

Beside the modifications as described above, other modifications can be used to modify the characteristics of the nucleic acids according to the present invention, whereby such other modifications may be selected from the group of proteins, lipids such as cholesterol, and sugar chains such as amylase, dextran etc.

Without wishing to be bound by any theory, by modifying the nucleic acid molecule according to the present invention with a high molecular weight moiety such as a polymer and more particularly one or several of the polymers disclosed herein, which are preferably physiologically acceptable, the excretion kinetic of the thus modified nucleic acid molecule of the invention from an animal or human body to which the modified nucleic acid molecule of the invention is administered is changed. More particularly, due to the increased molecular weight of the thus modified nucleic acid molecule of the invention and due to the nucleic acid molecule of the invention not being subject to metabolism particularly when in the L form, i.e. being an L-nucleic acid molecule, excretion from an animal body, preferably from a mammalian body and more preferably from a human body is decreased. As excretion typically occurs via the kidneys, the present inventors assume that the glomerular filtration rate of the thus modified nucleic acid molecule is significantly reduced compared to a nucleic acid molecule not having this kind of high molecular weight modification which results in an increase in the residence time of the modified nucleic acid molecule in the animal body. In connection therewith it is particularly noteworthy that, despite such high molecular weight modification the specificity of the nucleic acid molecule according to the present invention is not affected in a detrimental manner. Insofar, the nucleic acid molecule according to the present invention has among others, the surprising characteristic—which normally cannot be expected from a pharmaceutically active compound—that a pharmaceutical formulation providing for a sustained release is not necessarily required for providing a sustained release of the nucleic acid molecule according to the present invention. Rather, the nucleic acid molecule according to the present invention in its modified form comprising a high molecular weight moiety, can as such already be used as a sustained release-formulation as it acts, due to its modification, already as if it was released from a sustained-release formulation. Insofar, the modification(s) of the nucleic acid molecule according to the present invention as disclosed herein and the thus modified nucleic acid molecule according to the present invention and any composition comprising the same may provide for a distinct, preferably controlled pharmacokinetics and biodistribution thereof. This also includes residence time in the circulation of the animal and human body and distribution to tissues in such animal and human. Such modifications are further described in the patent application WO2003/035665.

However, it is also within the present invention that the nucleic acid according to the present invention does not comprise any modification and particularly no high molecular weight modification such as PEGylation or HESylation. Such embodiment is particularly preferred when the nucleic acid according to the present invention shows preferential distribution to any target organ or tissue in the body or when a fast clearance of the nucleic acid according to the present invention from the body after administration to the body is desired. An nucleic acid molecule according to the present invention as disclosed herein with a preferential distribution profile to any target organ or target tissue in the body would allow establishment of effective local concentrations in the target tissue while keeping systemic concentration of the nucleic acid molecule low. This would allow the use of low doses which is not only beneficial from an economic point of view, but also reduces unnecessary exposure of other tissues to the nucleic acid agent, thus reducing the potential risk of side effects. Fast clearance of the nucleic acid molecule according to the present invention from the body after administration might be desired, among others, in case of in vivo imaging or specific therapeutic dosing requirements using the nucleic acid molecule according to the present invention or a medicament comprising the same.

The nucleic acid molecule according to the present invention, and/or the antagonist according to the present invention may be used for the generation or manufacture of a medicament or a pharmaceutical composition. Such medicament or a pharmaceutical composition according to the present invention contains at a nucleic acid molecule of the invention optionally together with, at least one further pharmaceutically active compound, whereby the nucleic acid molecule of the invention preferably acts as pharmaceutically active compound itself. Such medicament comprises in a preferred embodiment at least a pharmaceutically acceptable carrier. Such carrier may be, e.g., water, buffer, PBS, glucose solution, preferably a 5% glucose, salt balanced solution, citrate, starch, sugar, gelatine or any other acceptable carrier substance. Such carrier is generally known to the one skilled in the art. It will be acknowledged by the person skilled in the art that any embodiments, use and aspects of or related to the medicament of the present invention is also applicable to the pharmaceutical composition of the present invention, and vice versa.

The indications, diseases and disorders for the treatment and/or prevention of which the nucleic acid molecule, the pharmaceutical composition and medicament of the present invention or prepared in accordance with the present invention result from the involvement, either direct or indirect, of CGRP in the respective pathogenic mechanism.

Based on involvement of CGRP in pathways relevant for or involved in migraine and other headache manifestations, it is evident that a nucleic acid molecule of the present invention, a pharmaceutical compositions of the present invention containing one or several thereof and a medicament of the present invention containing one or several thereof are useful in the treatment and/or prevention of said disease, disorders and diseased conditions.

The use of a nucleic acid molecule of the present invention, a pharmaceutical composition of the present invention containing one or several thereof and a medicament of the present invention containing one or several thereof is not restricted to potential therapeutic interventions in migraine and other headache manifestations as described above. Beyond that they are applicable to diseases and/or disorders and/or diseased conditions for which a pathophysiological involvement of CGRP has been described. Accordingly, such diseases and/or disorders and/or diseased conditions include, but are not limited to migraine, different forms of headache, acute pain, chronic pain, tolerance to morphine-based analgesia, osteoarthritis, angiogenesis, tumor growth, autoimmune diseases and/or inflammatory diseases, whereby preferably the acute pain and chronic pain is of inflammatory and/or neuropathic origin.

Of course, because the CGRP binding nucleic acid molecule according to the present invention interacts with or bind to CGRP, a skilled person will generally understand that the CGRP binding nucleic acid molecule according to the present invention can be easily used for the treatment, prevention and/or diagnosis of any disease as described herein of humans and animals. In connection therewith, it is to be acknowledged, in an embodiment, that the nucleic acid molecule according to the present invention can be used for the treatment and prevention of any of the diseases, disorder or condition described herein, irrespective of the mode of action underlying such disease, disorder and condition.

In order to avoid any unnecessary repetition, it should be acknowledged that due to the involvement of the CGRP-CGRP receptor axis as outlined in connection therewith said axis may be addressed by the nucleic acid molecule according to the present invention such that the claimed therapeutic, preventive and diagnostic effect is achieved. It should furthermore be acknowledged that the particularities of the diseases, disorders and conditions, of the patients and any detail of the treatment regimen described in connection therewith, may be subject to preferred embodiments of the instant application.

Acute and Chronic Pain. CGRP is highly expressed by nociceptive nerve fibres. There is accumulating evidence that CGRP is involved in the development and perpetuation of acute and chronic pain. Inflammations can be a potent trigger for acute and chronic pain sensations. In chronic pancreatitis pain is the most challenging symptom. It is promoted by increased expression of NGF in the pancreas that in turn induces upregulation of CGRP in the dorsal root ganglion (Winston, He et al. 2005; Wick, Hoge et al. 2006; Liu, Shenoy et al. 2011). Intrathecal administration of CGRP(8-37) can antagonize this mechanism and reduce hyperalgesia (Liu, Shenoy et al. 2011). In animal models of arthritis intrathecal CGRP(8-37) and Olcegepant significantly inhibited neuronal activity and increased the threshold of hindlimb withdrawal reflexes (McDougall 2006; Adwanikar, Ji et al. 2007). CGRP-deficient mice failed to demonstrate hyperalgesia after experimental induction of joint inflammation (Zhang and McDougall 2006). Furthermore, CGRP has been found at high levels in the synovial fluid of arthritic temporomandibular joints in association with spontaneous pain (Kopp 2001). In a model of deep tissue inflammation intravenous CGRP(8-37) blocked plasma extravasation and abolished both head and hindlimb mechanical allodynia (Ambalavanar, Moritani et al. 2006).

Elevated CGRP expression is observed in models of neuropathic pain (Zheng, Wang et al. 2008; Nitzan-Luques, Devor et al. 2011). CGRP(8-37) is effective in abolishing mechanical and thermal allodynia elicited by spinal hemisection or spinal nerve transection (Bennett, Chastain et al. 2000; Lee and Kim 2007). Similarly, CGRP(8-37) and Olecgepant effectively attenuated thermal hyperalgesia after partial sciatic nerve ligation (Ma and Quirion 2006). In models of diabetic neuropathic pain intravenous CGRP(8-37) significantly attenuated the hyperalgesic activity in mice with STZ-induced diabetes (Gabra and Sirois 2004). CGRP may furthermore be involved in post herpetic neuralgia that is thought to be a consequence of nerve damage caused by herpes zoster (Hou, Barr et al. 2011).

Low back pain is known to be to originate in sacroiliac joints. Histological studies of human tissue showed that CGRP is present the superficial layer of sacral and iliac cartilage (Szadek, Hoogland et al. 2010). In agreement, CGRP expression was increased in the dorsal root ganglion during adjuvant-induced low back pain in rats (Lee, Kim et al. 2009).

Evidence for an involvement of CGRP in cancer pain is provided by studies showing that increased tumor innervation with CGRP-positive fibres and CGRP release is associated with hyperalgesia (Wacnik, Baker et al. 2005; Schweizerhof, Stosser et al. 2009). Intra-tumor injection of CGRP(8-37) partially blocks tumor-associated hyperalgesia (Wacnik, Baker et al. 2005).

Pain is a characteristic symptom of irritable bowel syndrome. In a noninflammatory model of chronic colonic hypersensitivity blockade of CGRP receptor reduced colonic hypersensitivity. This suggests CGRP antagonism as a potential treatment for abdominal pain in irritable bowel syndrome (Bourdu, Dapoigny et al. 2005).

In cases of therapeutic interventions in migraine, others forms of headache, acute and chronic pain the nucleic acid molecule, the pharmaceutical composition and medicament of the invention or prepared in accordance with the present invention can be used in combinatorial therapies with established anagetics such as NSAIDs, ergot alkaloid derivatives (e.g. dihydroergotamine) and triptans, $5\text{-HT}_{1B/1D}$ receptor agonists (e.g. Sumatriptan).

Tolerance to Morphine-Based Analgesia. Prolonged exposure to morphine-based drugs leads to a gradual decrease of analgesic efficacy, limiting their clinical use. CGRP is suggested to be involved in mediating this tolerance to morphine-based analgesics. In rats, chronic intrathecal morphine treatment leads to tolerance to its antinociceptive effects and induces an up-regulation CGRP in the spinal dorsal horn. In turn, CGRP released from these nerve terminals contributes to the development of tolerance to morphine-induced analgesia. In animal models, intrathecal treatment with Olcegepant or CGRP(8-37) blocks these downstream effects, thereby leading to the maintenance of the analgesic properties of chronically used morphine. Accordingly, CGRP antagonists can potentially be used as adjuncts in opiate-based therapies (Powell, Ma et al. 2000; Wang, Ma et al. 2009).

Osteoarthritis. Hip joints from patients with painful osteoarthritis (abbr. OA) had a threefold higher density of CGRP-positive nerves compared to controls and histology of synovial tissues from rheumatoid arthritis and OA patients showed a significantly higher density of CGRP-positive nerve fibres in OA (Saxler, Loer et al. 2007; Dirmeier, Capellino et al. 2008). In agreement, the percentage of CGRP-positive fibres innervating the joint was significantly increased in an animal model of OA (Ferreira-Gomes, Adaes et al. 2010). The analgetic effect of a transient receptor potential cation channel subfamily V member 1 antagonist was associated with reduced spinal levels of CGRP in an OA model (Puttfarcken, Han et al. 2010). In addition to its role in nociception, CGRP may also directly be involved in bone metabolism. CGRP signaling maintains bone mass by stimulating osteoblast proliferation and differentiation and by suppression of RANKL-induced osteoclastogenesis and bone resorption (Han, Zhang et al. 2010; Wang, Shi et al. 2010).

Tumor Angiogenesis and Growth. In CGRP-deficient mice tumor growth and tumor-associated angiogenesis of transplanted lung carcinoma cells are significantly reduced. In wt mice, CGRP(8-37) or denervation suppressed carcinoma cell growth. These results indicate that CGRP facilitates tumor-associated angiogenesis and tumor growth. There is indication that the downstream molecule relevant to CGRP-dependent enhancement of angiogenesis is VEGF (Toda, Suzuki et al. 2008). In human, elevated CGRP expression has been identified in both plasma and tumours from specific cancers; including small cell lung carcinomas, prostate cancer, breast cancer and thyroid cancer. In prostate cancer, serum CGRP correlated with high-grade/stage disease. RAMP 1 mRNA expression has been detected in benign and malignant pheochromocytomas, Conn's adenoma and pancreatic cancers (Hay, Walker et al. 2011).

Ischemia-Induced Angiogenesis. Ischemia induces angiogenesis as a compensatory mechanism. CGRP levels were increased in rat hind limp ischemic tissue and adenoviral overexpression of CGRP resulted in increased capillary density in ischemic hind limbs (Zheng, Li et al. 2010). CGRP-deficient mice showed an impaired blood flow recovery and decreased capillary density after experimental hind limb ischemia. Subcutaneous infusion of CGRP(8-37) via miniosmotic pump delayed angiogenesis (Mishima, Ito et al. 2011).

Inflammation. There is evidence that CGRP directly impacts on inflammatory processes. CGRP is upregulated in animal models of arthritis (Nohr, Schafer et al. 1999; Chen, Willcockson et al. 2008). In a model of multiple sclerosis it was shown that CGRP promotes pathogenic T cell responses (Mikami, Watanabe et al. 2012). Increased CGRP levels were also observed in animal models of type 2 diabetes (Gram, Hansen et al. 2005; Tanaka, Shimaya et al. 2011). In a mouse model of psoriasis denervation or inhibition of CGRP by CGRP(8-37) resulted in significant reductions in $CD4^+$ cell numbers and acanthosis (Ostrowski, Belkadi et al. 2011). A role for CGRP in skin inflammation is furthermore suggested by studies showing that CGRP inhibits chemokine production by human dermal microvascular endothelial cells (Huang, Stohl et al. 2011) and that it modulated cytokines production by T cells from atopic dermatitis patients (Antunez, Torres et al. 2009).

Anxiety. Infusion of CGRP evokes anxiety-like responses in rats suggesting that CGRP antagonism may be a clinically useful strategy for anxiety reduction (Sink, Walker et al. 2011).

Neurodegenerative Diseases. A recent study showed that a mutation of androgen receptor which is crucial for the pathogenesis of spinal and bulbar muscular atrophy (SBMA) is associated with increased CGRP expression and that suppression of CGRP expression reduces clinical symptoms (Minamiyama, Katsuno et al. 2012).

A pathogenic role of CGRP has been suggested in various other diseases including cystic fibrosis (Xie, Fisher et al. 2011), mastocytosis (Maintz, Wardelmann et al. 2011), polycystic ovary syndrome (PCOS) (Zhang, Gong et al. 2012), non-erosive reflux disease (Xu, Li et al. 2012)

In a further embodiment, the medicament comprises a further pharmaceutically active agent. Such further pharmaceutically active compounds are, among others but not limited thereto, compounds for treatment and/or prevention of migraine, acute and chronic pain, whereby the compounds are selected from the group comprising triptanes, NSAIDs, opioids, N-type voltage-gated calcium channels blockers (Ziconotide), antidepressant and antiepileptic drugs. It will be understood by the one skilled in the art that given the various indications which can be addressed in accordance with the present invention by the nucleic acid molecule according to the present invention, said further pharmaceutically active agent(s) may be any one which in principle is suitable for the treatment and/or prevention of such diseases. The nucleic acid molecule according to the present invention, particularly if present or used as a medicament, preferably, is or is to be combined with triptanes, NSAIDs, opioids, N-type voltage-gated calcium channels blockers (Ziconotide), antidepressant and antiepileptic drugs.

It is within the present invention that the medicament of the invention is alternatively or additionally used, in principle, for the prevention of any of the diseases disclosed in connection with the use of the medicament for the treatment of said diseases. Respective markers therefore, i.e. for the respective diseases are known to the ones skilled in the art. Preferably, the respective marker is CGRP.

In one embodiment of the medicament of the present invention, such medicament is for use in combination with other treatments for any of the diseases disclosed herein, particularly those for which the medicament of the present invention is to be used.

"Combination therapy" (or "co-therapy") includes the administration of a medicament of the present invention and at least a second or further pharmaceutically active agent as part of a specific treatment regimen intended to provide the beneficial effect from the co-action of these therapeutic agents, i.e. the nucleic acid molecule of the present invention and said second or further agent. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may be, but generally is not, intended to encompass the administration of two or more of these therapeutic agents as part of separate monotherapy regimens. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to a subject a single capsule having a fixed ratio of each therapeutic agent or in multiple, single capsules for each of the therapeutic agents, whereby the multiple, single capsules are administered at the same time or in a timely manner so that the therapeutic effect is obtained as if the multiple single capsules were administered simultaneously.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes.

For example, a first therapeutic agent of the combination may be administered by injection while the other therapeutic agents of the combination may be administered topically.

Alternatively, for example, all therapeutic agents may be administered topically or all therapeutic agents may be administered by injection. "Combination therapy" can also embrace the administration of the therapeutic agents as described above in further combination with other biologically or pharmaceutically active ingredients. Where the combination therapy further comprises a non-drug treatment, the non-drug treatment may be conducted at any suitable time as long as a beneficial effect from the co-action of the combination of the therapeutic agents and non-drug treatment is achieved. For example, in appropriate cases, the beneficial effect is still achieved when the non-drug treatment is temporally separated from the administration of the therapeutic agents, perhaps by days or even weeks.

As outlined in general terms above, the medicament according to the present invention can be administered, in principle, in any form known to the ones skilled in the art. A preferred route of administration is systemic administration, more preferably by parenteral administration, preferably by injection. Alternatively, the medicament may be administered locally. Other routes of administration comprise intramuscular, intraperitoneal, and subcutaneous, per orum, intranasal, intratracheal or pulmonary with preference given to the route of administration that is the least invasive, while ensuring efficiency.

Parenteral administration is generally used for subcutaneous, intramuscular or intravenous injections and infusions. Additionally, one approach for parenteral administration employs the implantation of a slow-release or sustained-released systems, which assures that a constant level of dosage is maintained, that is well known to the ordinary skill in the art.

Furthermore, preferred medicaments of the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, preferably, be continuous rather than intermittent throughout the dosage regimen. Other preferred topical preparations include creams, ointments, lotions, aerosol sprays and gels.

Subjects that will respond favorably to a method of the invention include medical and veterinary subjects in general, including human beings and human patients. Among other subjects for whom the method and means of the invention are useful, are cats, dogs, large animals, avians such as chickens, and the like.

The medicament of the present invention will generally comprise an effective amount of the active component(s) of the therapy, including, but not limited to, a nucleic acid molecule of the present invention, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the medicament of the present invention.

In a further aspect the present invention is related to a pharmaceutical composition. Such pharmaceutical composition comprises at least a nucleic acid molecule according to the present invention and preferably a pharmaceutically acceptable binder. Such binder can be any binder used and/or known in the art. More particularly, such binder is any binder as discussed in connection with the manufacture of the medicament disclosed herein, however, is not limited thereto. In a further embodiment, the pharmaceutical composition of the present invention comprises a further pharmaceutically active agent.

The preparation of a medicament and a pharmaceutical composition of the invention is known to those of skill in the art in light of the present disclosure. Typically, such composition may be prepared as, injectable, either as a liquid solution or a suspension; a solid form suitable for solution in, or suspension in, a liquid prior to injection; as a tablet or other a solid for oral administration; as a time release capsules; or in any other form currently used, including eye drops, cream, lotion, salve, inhalant and the like. The use of sterile formulations, such as saline-based washes, by surgeons, physicians or health care workers to treat a particular area in the operating field may also be particularly useful. Composition of the invention may also be delivered via microdevice, micropar ticle or sponge.

Upon formulation, a medicament of the invention will be administered in a manner compatible with the dosage formulation, and in such amount as is pharmacologically effective. The formulation is easily administered in a variety of dosage forms, such as the type of injectable solutions described above, but drug release capsules and the like can also be employed.

The medicament of the invention can also be administered in oral dosage forms as timed release and sustained release tablets or capsules, pills, powders, granules, elixirs, tinctures, suspensions, syrups and emulsions. Suppositories are advantageously prepared from fatty emulsions or suspensions.

The pharmaceutical composition or medicament of the invention may be sterilized and/or contain an adjuvant, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

A liquid, particularly, an injectable composition can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

The medicament and nucleic acid molecule, respectively, of the present invention can also be administered in the form of a liposome delivery system, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, what is well known to the ordinary skill in the art. For example, the nucleic acid molecule can be provided as a complex with a lipophilic compound or non-immunogenic, high molecular weight compound constructed using methods known in the art. Additionally, liposomes may bear such nucleic acid molecules on their surface for targeting and carrying cytotoxic agents internally to mediate cell killing. An example of nucleic-acid associated complexes is provided in U.S. Pat. No. 6,011,020.

The medicament and nucleic acid molecule, respectively, of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolylysine substituted with palmitoyl residues. Furthermore, the medicaments and nucleic acid molecules, respectively, of the present invention may be coupled to a class of biodegradable polymers useful in achieving controlled release of a drag, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition and medicament, respectively, to be administered may also contain minor amounts of non-toxic auxiliary substances such as wetting or emulsifying agents, pH buffering agents, and other substances such as for example, sodium acetate, and triethanolamine oleate.

The dosage regimen utilizing the nucleic acid molecule and medicament, respectively, of the present invention is selected in accordance with a variety of factors including type, species, age, weight, sex and medical condition of the patient; the severity of the condition to be treated; the route of administration; the renal and hepatic function of the patient; and the particular aptamer or salt thereof employed. An ordinarily skilled physician or veterinarian can readily determine and prescribe the effective amount of the drug required to prevent, counter or arrest the progress of the condition.

Effective plasma levels of the nucleic acid molecule according to the present invention preferably range from 500 fM to 200 preferably from 1 nM to 20 µM, more preferably from 5 nM to 20 µM, most preferably 50 nM to 20 µM in the treatment of any of the diseases disclosed herein.

The nucleic acid molecule and medicament, respectively, of the present invention may preferably be administered in a single daily dose, every second or third day, weekly, every second week, in a single monthly dose or every third month.

It is within the present invention that a medicament of the invention as described herein constitutes a pharmaceutical composition disclosed herein and preferably a pharmaceutical composition of the invention.

In a further aspect the present invention is related to a method for the treatment of a subject who is in need of such treatment, whereby the method comprises the administration of a pharmaceutically active amount of nucleic acid molecule according to the present invention. In an embodiment, the subject suffers from a disease or is at risk to develop such disease, whereby the disease is any of those disclosed herein, particularly any of those diseases disclosed in connection with the use of any of the nucleic acid molecule according to the present invention for the manufacture of a medicament.

As preferably used herein a diagnostic or diagnostic agent or diagnostic means is suitable to detect, either directly or indirectly CGRP, preferably CGRP as described herein and more preferably CGRP as described herein in connection with the various disorders and diseases described herein. The diagnostic is suitable for the detection and/or follow-up of any of the disorders and diseases, respectively, described herein. Such detection is possible through the binding of the nucleic acids according to the present invention to CGRP. Such binding can be either directly or indirectly be detected. The respective methods and means are known to the ones skilled in the art. Among others, the nucleic acid molecule according to the present invention may comprise a label which allows the detection of the nucleic acid molecule according to the present invention, preferably the nucleic acid molecule bound to CGRP. Such a label is preferably selected from the group comprising radioactive, enzymatic and fluorescent labels. In principle, all known assays developed for antibodies can be adopted for the nucleic acid molecule according to the present invention whereby the target-binding antibody is substituted by a target-binding nucleic acid molecule of the invention. In antibody-assays using unlabeled target-binding antibodies the detection is preferably done by a secondary antibody which is modified with radioactive, enzymatic and fluorescent labels and bind to the target-binding antibody at its Fc-fragment. In the case of a nucleic acid, preferably a nucleic acid molecule according to the present invention, the nucleic acid is modified with such label, whereby preferably such label is selected from the group comprising biotin, Cy-3 and Cy-5, and such label is detected by an antibody directed against such label, e.g. an anti-biotin antibody, an anti-Cy3 antibody or an anti-Cy5 antibody, or—in the case that the label is biotin—the label is detected by streptavidin or avidin which naturally binds to biotin. Such antibody, streptavidin or avidin in turn is preferably modified with a respective label, e.g. a radioactive, enzymatic or fluorescent label (like secondary antibody) which provides a signal allowing detection.

In a further embodiment the nucleic acid molecules according to the invention is detected or analysed by a second detection means, wherein the said detection means is a molecular beacon. The methodology of molecular beacon is known to persons skilled in the art and reviewed by Mairal et al. (Mairal et al., 2008).

It will be acknowledged that the detection of CGRP using the nucleic acid molecule according to the present invention will particularly allow the detection of CGRP as defined herein.

In connection with the detection of CGRP a preferred method of the invention comprises the following steps:
(a) providing a sample which is to be tested for the presence of CGRP,
(b) providing a nucleic acid molecule according to the present invention,
(c) reacting the sample with the nucleic acid, preferably in a reaction vessel, whereby step (a) can be performed prior to step (b), or step (b) can be performed prior to step (a).

In a preferred embodiment a further step d) is provided, which consists the detection of the reaction of the sample with the nucleic acid molecule. Preferably, the nucleic acid molecule of step b) is immobilised to a surface. The surface may be the surface of a reaction vessel such as a reaction tube, a well of a plate, or the surface of a device contained in such reaction vessel such as, for example, a bead. The immobilisation of the nucleic acid molecule to the surface can be made by any means known to the ones skilled in the art including, but not limited to, non-covalent or covalent linkages. Preferably, the linkage is established via a covalent chemical bond between the surface and the nucleic acid molecule. However, it is also within the present invention that the nucleic acid molecule of the invention is indirectly immobilised to a surface, whereby such indirect immobilisation involves the use of a further component or a pair of interaction partners. Such further component is preferably a compound which specifically interacts with the nucleic acid to be immobilised which is also referred to as interaction partner, and thus mediates the attachment of the nucleic acid molecule to the surface. The interaction partner is preferably selected from the group comprising nucleic acids, polypeptides, proteins and antibodies. Preferably, the interaction partner is an antibody, more preferably a monoclonal antibody. Alternatively, the interaction partner is a nucleic acid, preferably a functional nucleic acid. More preferably such functional nucleic acid is selected from the group comprising aptamers, Spiegelmers, and nucleic acids which are at least partially complementary to the nucleic acid. In a further alternative embodiment, the binding of the nucleic acid to the surface is mediated by a multi-partite interaction partner. Such multi-partite interaction partner is preferably a pair of interaction partners or an interaction partner consisting of a first member and a second member, whereby the first member is comprised by or attached to the nucleic acid molecule and the second member is attached to or comprised by the surface. The multi-partite interaction partner is preferably selected from the group of pairs of interaction partners comprising biotin and avidin, biotin and streptavidin, and biotin and neutravidin. Preferably, the first member of the pair of interaction partners is biotin.

A preferred result of such method is the formation of an immobilised complex of CGRP and the nucleic acid molecule of the invention, whereby more preferably said complex is detected. It is within an embodiment that from the complex the CGRP moiety is detected.

A respective detection means which is in compliance with this requirement is, for example, any detection means which is specific for that/those part(s) of the CGRP. A particularly preferred detection means is a detection means which is selected from the group comprising nucleic acids, polypeptides, proteins and antibodies, the generation of which is known to the ones skilled in the art.

The method of the invention for the detection of CGRP also comprises in an embodiment that the sample is removed from the reaction vessel which has preferably been used to perform step c).

The method of the invention comprises in a further embodiment also the step of immobilising an interaction partner of CGRP on a surface, preferably a surface as defined above, whereby the interaction partner is defined as herein and preferably as above in connection with the respective method and more preferably comprises nucleic acids, polypeptides, proteins and antibodies in their various embodiments. In this embodiment, a particularly preferred detection means is a nucleic acid molecule according to the present invention, whereby such nucleic acid may preferably be labelled or non-labelled. In case such nucleic acid molecule is labelled it can be directly or indirectly detected. Such detection may also involve the use of a second detection means which is, preferably, also selected from the group comprising nucleic acids, polypeptides, proteins. Such detection means are preferably specific for the nucleic acid molecule according to the present invention. In a more preferred embodiment, the second detection means is a molecular beacon. Either the nucleic acid molecule or the second detection means or both may comprise in a preferred embodiment a detection label. The detection label is preferably selected from the group comprising biotin, a bromo-desoxyuridine label, a digoxigenin label, a fluorescence label, a UV-label, a radio-label, and a chelator molecule. Alternatively, the second detection means interacts with the detection label which is preferably contained by, comprised by or attached to the nucleic acid molecule. Particularly preferred combinations are as follows:

the detection label is biotin and the second detection means is an antibody directed against biotin, or the detection label is biotin and the second detection means is an avidin or an avidin carrying molecule, or the detection label is biotin and the second detection means is a streptavidin or a streptavidin carrying molecule, or the detection label is biotin and the second detection means is a neutravidin or a neutravidin carrying molecule, or the detection label is a bromo-desoxyuridine and the second detection means is an antibody directed against bromo-desoxyuridine, or the detection label is a digoxigenin and the second detection means is an antibody directed against digoxigenin, or the detection label is a chelator and the second detection means is a radio-nuclide, whereby it is preferred that said detection label is attached to the nucleic acid molecule. It is to be acknowledged that this kind of combination is also applicable to the embodiment where the nucleic acid is attached to the surface. In such embodiment it is preferred that the detection label is attached to the interaction partner.

Finally, it is also within the present invention that the second detection means is detected using a third detection means, preferably the third detection means is an enzyme, more preferably showing an enzymatic reaction upon detection of the second detection means, or the third detection means is a means for detecting radiation, more preferably radiation emitted by a radio-nuclide. Preferably, the third detection means is specifically detecting and/or interacting with the second detection means.

Also in the embodiment with an interaction partner of CGRP being immobilised on a surface and the nucleic acid molecule according to the present invention is preferably added to the complex formed between the interaction partner and the CGRP, the sample can be removed from the reaction, more preferably from the reaction vessel where step c) and/or d) are performed.

In an embodiment the nucleic acid molecule according to the present invention comprises a fluorescence moiety and whereby the fluorescence of the fluorescence moiety is different upon complex formation between the nucleic acid and CGRP and free CGRP.

In a further embodiment the nucleic acid molecule is a derivative of the nucleic acid molecule according to the present invention, whereby the derivative of the nucleic acid comprises at least one fluorescent derivative of adenosine replacing adenosine. In a preferred embodiment the fluorescent derivative of adenosine is ethenoadenosine.

In a further embodiment the complex consisting of the derivative of the nucleic acid molecule according to the present invention and the CGRP is detected using fluorescence.

In an embodiment of the method a signal is created in step (c) or step (d) and preferably the signal is correlated with the concentration of CGRP in the sample.

In a preferred aspect, the assays being part of the method of the invention may be performed in 96-well plates, where components are immobilized in the reaction vessels as described above and the wells acting as reaction vessels.

The nucleic acid molecule of the invention may further be used as starting material for drug discovery. Basically, there are two possible approaches. One approach is the screening of compound libraries whereas such compound libraries are preferably low molecular weight compound libraries. In an embodiment the screening is a high throughput screening. Preferably, high throughput screening is the fast, efficient, trial-and-error evaluation of compounds in a target based assay. In best case the analysis is carried by colorimetric measurement. Libraries as used in connection therewith are known to the one skilled in the art.

In case of screening of compound libraries, such as by using competitive assay which is known to the one skilled in the arts, appropriate CGRP analogues, CGRP agonists or CGRP antagonists may be identified. Such competitive assays may be set up as follows. The nucleic acid molecule of the invention, preferably a Spiegelmer which is a target binding L-nucleic acid, is coupled to a solid phase. In order to identify CGRP analogues labelled CGRP may be added to the assay. A potential analogue competes with the CGRP molecules binding to the Spiegelmer which goes along with a decrease in the signal obtained by the respective label.

Screening for agonists or antagonists may involve the use of a cell culture assay as known to the ones skilled in the art.

The kit according to the present invention may comprise at least one or several of the nucleic acid molecule, preferably for the detection of CGRP. Additionally, the kit may comprise at least one or several positive or negative controls. A positive control may, for example, be CGRP, particularly the one against which the nucleic acid molecule of the invention is selected or to which it binds, preferably, in liquid form. A negative control may, e.g., be a peptide which is defined in terms of biophysical properties similar to CGRP but which is not recognized by the nucleic acid molecule of the invention.

Furthermore, said kit may comprise one or several buffers. The various ingredients may be contained in the kit in dried or lyophilised form or solved in a liquid. The kit may comprise one or several containers which in turn may contain one or several ingredients of the kit. In a further embodiment, the kit comprises an instruction or instruction leaflet which provides to the user information on how to use the kit and its various ingredients.

The pharmaceutical and bioanalytical determination of the nucleic acid molecule according to the present invention is elementarily for the assessment of its pharmacokinetic and biodynamic profile in several humours, tissues and organs of the human and non-human body. For such purpose, any of the detection methods disclosed herein or known to a person skilled in the art may be used. In a further aspect of the present invention a sandwich hybridisation assay for the detection of the nucleic acid molecule according to the present invention is provided. Within the detection assay a capture probe and a detection probe are used. The capture probe is complementary to a first part and the detection probe to a second part of the nucleic acid molecule according to the present invention. The capture probe is immobilised to a surface or matrix. The detection probe preferably carries a marker molecule or label that can be detected as previously described herein.

The detection of the nucleic acid molecule according to the present invention can be carried out as follows: The nucleic acid molecule according to the present invention hybridises with one of its ends to the capture probe and with the other end to the detection probe. Afterwards, unbound detection probe is removed by, e. g., one or several washing steps. The amount of bound detection probe which preferably carries a label or marker molecule can be measured subsequently as, for example, outlined in more detail in WO/2008/052774 which is incorporated herein by reference.

As preferably used herein, the term treatment comprises in a preferred embodiment additionally or alternatively prevention and/or follow-up.

As preferably used herein, the terms disease and disorder shall be used in an interchangeable manner, if not indicated to the contrary.

As used herein, the term comprise is preferably not intended to limit the subject matter followed or described by said term.

The various SEQ ID NOs, the chemical nature of the nucleic acid molecules according to the present invention, the actual sequence thereof and the internal reference number is summarized in the following table.

TABLE 1

| SEQ ID NO. | Internal Reference | | Sequence |
|---|---|---|---|
| 001 | 212-G1-001 | L-RNA | CGUGCUGUCGGAGACUACUCGUCGAGUAGAAAUAGGUCCCCUCCCACG |
| 002 | 226-F2-001 | L-RNA | CCGUGCUGUCGGAGACUACUCGUCGAGUAGAAAUAGGUCCCCUCCCACGG |
| 003 | 212-F1-001 | L-RNA | CGUGCUGUUGGAGACUACUUGUUAAGUAGAUAUAGGUUCCCUCCCACG |
| 004 | 224-B2-001 | L-RNA | GCGUGCUGUCGGAGACUACGCUUCGCGUAGAGAUAGGUCCCCUCCCACGC |
| 005 | 224-E1-001 | L-RNA | GCAGCUGUCGGAGACUCACCGUCGGUGAGAAAUAGGUCCCCUCCCUGC |
| 006 | 226-A2-002 | L-RNA | CGUGAUAUCGGAGACUACUCGUGGAGUAGAAAUAGGUCCCCUCCCACG |
| 007 | 226-A3-001 | L-RNA | CCGUGCUGUCGGAGACUACUCAUCGAGUAGAAAUAGGUCCCCUCCCACGG |
| 008 | 226-G2-002 | L-RNA | CGUGCAGUCGGAGACUACUCAUCGAGUAGAAAUAGGUCCCUUCCCACG |
| 009 | 226-C2-002 | L-RNA | CGUGCUGUCGGAGACUACUCGUAGAGUGGAGAUAGGUCCCCUCCCACG |

TABLE 1-continued

| | | | |
|---|---|---|---|
| 010 | 226-E1-002 | L-RNA | CGUGCUGUCGGAGACUACUCGUAGAGUAGAGAUAAGUCCCCUCCUACG |
| 011 | 226-F1-001 | L-RNA | CCGUGCUGUCGGAGACUACUCGUAGAGUAGAUAUAGGUCCCCUCCCACGG |
| 012 | 226-C3-001 | L-RNA | CCGUGCUGUCGGAGACUACUCGUAGAGUAGAAAUAGGUCCCCUCCCACGG |
| 013 | 231-A1-001 | L-RNA | GUCAUGCUGUCGGAGACUACUCAUCGAGUAGAAAUAGGUCCCCUCCCACGGC |
| 014 | 231-G2-001 | L-RNA | GCCAUGCUGUCGGAGACUACUCAUCGAGUAGAAAUAGAUCCCCUCCCAUGGC |
| 015 | 231-C1-001 | L-RNA | GCCGUGCUGUCGGAGACUACUCAUCGAGUAGAAAUAGGUCCCCUCCCACGGC |
| 016 | 231-C2-001 | L-RNA | GCCGUGCUGUCGGAGACUACUCGUUGAGUAGAAAUAGGUCCCCUCCCACGGC |
| 017 | 231-D1-001 | L-RNA | GCCGUGCUGUCGGAGACUACUCGUUGAGUAGAAAUAGGUCCCGUCCCACGGC |
| 018 | 231-F1-001 | L-RNA | GCCGUGCUGUCGGAGACUACUCGCCGAGUAGAAAUAGGUCCCCUCCCACGGC |
| 019 | 231-E1-001 | L-RNA | CCCGUGCUGUCGGAGACUACUCGUCGAGUAGAAAUAGGUCCCCUCCCACGGG |
| 020 | 231-B3-001 | L-RNA | CACCGUGCUGUCGGAUACUACUCGCCGAGUAGAAAUAGGUCCCCUCCCACGGUG |
| 021 | 231-A2-001 | L-RNA | GGCCGUGCUGUCGGAGACUACUCGCCGAGUAGAAAUAGGUCCCCUCCCACGGCU |
| 022 | 231-E2-001 | L-RNA | CCCGUGCUGUCGGAGACUACUCGUAGGGUAGAAAUAGGUCCCCUCCCACGGG |
| 023 | 231-H2-001 | L-RNA | GCCGUGUUGUCGGAGACUACCCCCAGGGUAGAAAUAGGUCCCCUCCCACGGC |
| 024 | 226-F2-003 | L-RNA | GCGUGCUGUCGGAGACUACUCGUCGAGUAGAAAUAGGUCCCCUCCCACGC |
| 025 | 226-F2-004 | L-RNA | GGGUGCUGUCGGAGACUACUCGUCGAGUAGAAAUAGGUCCCCUCCCACCC |
| 026 | 226-F2-005 | L-RNA | GCCUGCUGUCGGAGACUACUCGUCGAGUAGAAAUAGGUCCCCUCCCAGGC |
| 027 | 226-F2-001-D03 | L-RNA/L-DNA | CCdGUGCUGUCGGAGACUACUCGUCGAGUAGAAAUAGGUCCCCUCCCACGG |
| 028 | 226-F2-001-D05 | L-RNA/L-DNA | CCGUdGCUGUCGGAGACUACUCGUCGAGUAGAAAUAGGUCCCCUCCCACGG |
| 029 | 226-F2-001-D08 | L-RNA/L-DNA | CCGUGCUdGUCGGAGACUACUCGUCGAGUAGAAAUAGGUCCCCUCCCACGG |
| 030 | 226-F2-001-D09 | L-RNA/L-DNA | CCGUGCUGdTCGGAGACUACUCGUCGAGUAGAAAUAGGUCCCCUCCCACGG |
| 031 | 226-F2-001-D14 | L-RNA/L-DNA | CCGUGCUGUCGGAdGACUACUCGUCGAGUAGAAAUAGGUCCCCUCCCACGG |
| 032 | 226-F2-001-D16 | L-RNA/L-DNA | CCGUGCUGUCGGAGAdCUACUCGUCGAGUAGAAAUAGGUCCCCUCCCACGG |
| 033 | 226-F2-001-D19 | L-RNA/L-DNA | CCGUGCUGUCGGAGACUAdCUCGUCGAGUAGAAAUAGGUCCCCUCCCACGG |
| 034 | 226-F2-001-D22 | L-RNA/L-DNA | CCGUGCUGUCGGAGACUACUCdGUCGAGUAGAAAUAGGUCCCCUCCCACGG |
| 035 | 226-F2-001-D23 | L-RNA/L-DNA | CCGUGCUGUCGGAGACUACUCGdTCGAGUAGAAAUAGGUCCCCUCCCACGG |
| 036 | 226-F2-001-D24 | L-RNA/L-DNA | CCGUGCUGUCGGAGACUACUCGUdCGAGUAGAAAUAGGUCCCCUCCCACGG |
| 037 | 226-F2-001-D25 | L-RNA/L-DNA | CCGUGCUGUCGGAGACUACUCGUCdGAGUAGAAAUAGGUCCCCUCCCACGG |
| 038 | 226-F2-001-D26 | L-RNA/L-DNA | CCGUGCUGUCGGAGACUACUCGUCGdAGUAGAAAUAGGUCCCCUCCCACGG |
| 039 | 226-F2-001-D28 | L-RNA/L-DNA | CCGUGCUGUCGGAGACUACUCGUCGAGdTAGAAAUAGGUCCCCUCCCACGG |
| 040 | 226-F2-001-D30 | L-RNA/L-DNA | CCGUGCUGUCGGAGACUACUCGUCGAGUAdGAAAUAGGUCCCCUCCCACGG |
| 041 | 226-F2-001-D33 | L-RNA/L-DNA | CCGUGCUGUCGGAGACUACUCGUCGAGUAGAAdAUAGGUCCCCUCCCACGG |
| 042 | 226-F2-001-D34 | L-RNA/L-DNA | CCGUGCUGUCGGAGACUACUCGUCGAGUAGAAAdTAGGUCCCCUCCCACGG |
| 043 | 226-F2-001-D37 | L-RNA/L-DNA | CCGUGCUGUCGGAGACUACUCGUCGAGUAGAAAUAGdGUCCCCUCCCACGG |
| 044 | 226-F2-001-D39 | L-RNA/L-DNA | CCGUGCUGUCGGAGACUACUCGUCGAGUAGAAAUAGGUdCCCCUCCCACGG |
| 045 | 226-F2-001-D41 | L-RNA/L-DNA | CCGUGCUGUCGGAGACUACUCGUCGAGUAGAAAUAGGUCCdCCUCCCACGG |
| 046 | 226-F2-001-D42 | L-RNA/L-DNA | CCGUGCUGUCGGAGACUACUCGUCGAGUAGAAAUAGGUCCCdCUCCCACGG |
| 047 | 226-F2-001-D44 | L-RNA/L-DNA | CCGUGCUGUCGGAGACUACUCGUCGAGUAGAAAUAGGUCCCCUdCCCACGG |
| 048 | 226-F2-001-D45 | L-RNA/L-DNA | CCGUGCUGUCGGAGACUACUCGUCGAGUAGAAAUAGGUCCCCUCdCCACGG |
| 049 | 226-F2-001-D46 | L-RNA/L-DNA | CCGUGCUGUCGGAGACUACUCGUCGAGUAGAAAUAGGUCCCCUCCdCACGG |

TABLE 1-continued

| 050 | 226-F2-001-D47 | L-RNA/L-DNA | CCGUGCUGUCGGAGACUACUCGUCGAGUAGAAAUAGGUCCCCUCCCdACGG |
| 051 | 226-F2-001-D48 | L-RNA/L-DNA | CCGUGCUGUCGGAGACUACUCGUCGAGUAGAAAUAGGUCCCCUCCCAdCGG |
| 052 | 226-F2-001-D49 | L-RNA/L-DNA | CCGUGCUGUCGGAGACUACUCGUCGAGUAGAAAUAGGUCCCCUCCCACdGG |
| 053 | 226-F2-001-D50 | L-RNA/L-DNA | CCGUGCUGUCGGAGACUACUCGUCGAGUAGAAAUAGGUCCCCUCCCACGdG |
| 054 | 226-F2-001-D41/D44 | L-RNA/L-DNA | CCGUGCUGUCGGAGACUACUCGUCGAGUAGAAAUAGGUCCdCCUdCCCACGG |
| 055 | 212-G1-001 | D-RNA | CGUGCUGUCGGAGACUACUCGUCGAGUAGAAAUAGGUCCCCUCCCACG |
| 056 | 226-F2-001 | D-RNA | CCGUGCUGUCGGAGACUACUCGUCGAGUAGAAAUAGGUCCCCUCCCACGG |
| 057 | 212-F1-001 | D-RNA | CGUGCUGUUGGAGACUACUUGUUAAGUAGAUAUAGGUUCCCUCCCACG |
| 058 | 224-B2-001 | D-RNA | GCGUGCUGUCGGAGACUACGCUUCGCGUAGAGAUAGGUCCCCUCCCACGC |
| 059 | 224-E1-001 | D-RNA | GCAGCUGUCGGAGACUCACCGUCGGUGAGAAAUAGGUCCCCUCCCUGC |
| 060 | 226-A2-002 | D-RNA | CGUGAUAUCGGAGACUACUCGUGGAGUAGAAAUAGGUCCCCUCCCACG |
| 061 | 226-A3-001 | D-RNA | CCGUGCUGUCGGAGACUACUCAUCGAGUAGAAAUAGGUCCCCUCCCACGG |
| 062 | 226-G2-002 | D-RNA | CGUGCAGUCGGAGACUACUCAUCGAGUAGAAAUAGGUCCCUUCCCACG |
| 063 | 226-C2-002 | D-RNA | CGUGCUGUCGGAGACUACUCGUAGAGUGGAGAUAGGUCCCCUCCCACG |
| 064 | 226-E1-002 | D-RNA | CGUGCUGUCGGAGACUACUCGUAGAGUAGAGAUAAGUCCCCUCCUACG |
| 065 | 226-F1-001 | D-RNA | CCGUGCUGUCGGAGACUACUCGUAGAGUAGAUAUAGGUCCCCUCCCACGG |
| 066 | 226-C3-001 | D-RNA | CCGUGCUGUCGGAGACUACUCGUAGAGUAGAAAUAGGUCCCCUCCCACGG |
| 067 | 231-A1-001 | D-RNA | GUCAUGCUGUCGGAGACUACUCAUCGAGUAGAAAUAGGUCCCCUCCCACGGC |
| 068 | 231-G2-001 | D-RNA | GCCAUGCUGUCGGAGACUACUCAUCGAGUAGAAAUAGAUCCCCUCCCAUGGC |
| 069 | 231-C1-001 | D-RNA | GCCGUGCUGUCGGAGACUACUCAUCGAGUAGAAAUAGGUCCCCUCCCACGGC |
| 070 | 231-C2-001 | D-RNA | GCCGUGCUGUCGGAGACUACUCGUUGAGUAGAAAUAGGUCCCCUCCCACGGC |
| 071 | 231-D1-001 | D-RNA | GCCGUGCUGUCGGAGACUACUCGUUGAGUAGAAAUAGGUCCCGUCCCACGGC |
| 072 | 231-F1-001 | D-RNA | GCCGUGCUGUCGGAGACUACUCGCCGAGUAGAAAUAGGUCCCCUCCCACGGC |
| 073 | 231-E1-001 | D-RNA | CCCGUGCUGUCGGAGACUACUCGUCGAGUAGAAAUAGGUCCCCUCCCACGGG |
| 074 | 231-B3-001 | D-RNA | CACCGUGCUGUCGGAUACUACUCGCCGAGUAGAAAUAGGUCCCCUCCCACGGUG |
| 075 | 231-A2-001 | D-RNA | GGCCGUGCUGUCGGAGACUACUCGCCGAGUAGAAAUAGGUCCCCUCCCACGGCU |
| 076 | 231-E2-001 | D-RNA | CCCGUGCUGUCGGAGACUACUCGUAGGGUAGAAAUAGGUCCCCUCCCACGGG |
| 077 | 231-H2-001 | D-RNA | GCCGUGUUGUCGGAGACUACCCCCAGGGUAGAAAUAGGUCCCCUCCCACGGC |
| 078 | 226-F2-001-D41-40kDa-PEG, NOX-L41 | L-RNA/L-DNA | 40kDa-PEG-CCGUGCUGUCGGAGACUACUCGUCGAGUAGAAAUAGGUCCdCCUCCCACGG |
| 079 | 226-F2-003 | D-RNA | GCGUGCUGUCGGAGACUACUCGUCGAGUAGAAAUAGGUCCCCUCCCACGC |
| 080 | 226-F2-004 | D-RNA | GGGUGCUGUCGGAGACUACUCGUCGAGUAGAAAUAGGUCCCCUCCCACCC |
| 081 | 226-F2-005 | D-RNA | GCCUGCUGUCGGAGACUACUCGUCGAGUAGAAAUAGGUCCCCUCCCAGGC |
| 082 | Human alpha-CGRP, h-αCGRP, alpha CGRP from macaca mulatta | L-peptide | ACDTATCVTHRLAGLLSRSGGVVKNNFVPTNVGSKAF |
| 083 | Human beta-CGRP | L-peptide | ACNTATCVTHRLAGLLSRSGGMVKSNFVPTNVGSKAF |
| 084 | Human amylin, h-Amylin | L-peptide | KCNTATCATQRLANFLVHSSNNFGAILSSTNVGSNTY |
| 085 | Human calcitonin | L-peptide | CGNLSTCMLGTYTQDFNKFHTFPQTAIGVGAP |

TABLE 1-continued

| | | | |
|---|---|---|---|
| 086 | Human adreno-medullin | L-peptide | YRQSMNNFQGLRSFGCRFGTCTVQKLAHQIYQFTDKDKDNVAPRSKISPQGY |
| 087 | Human intermedin | L-peptide | TQAQLLRVGCVLGTCQVQNLSHRLWQLMGPAGRQDSAPVDPSSPHSY |
| 088 | 226-F2-001-5'-40kDa-PEG | L-RNA/L-DNA | 40kDa-PEG-CCGUGCUGUCGGAGACUACUCGUCGAGUAGAAAUAGGUCCCCUCCCACGG |
| 089 | Alpha-CGRP from rat, r-αCGRP, CGRP from mouse | L-peptide | SCNTATCVTHRLAGLLSRSGGVVKDNFVPTNVGSEAF |
| 090 | | L-RNA/L-DNA | CUGUCGGAGACUACdUCGUCGAGdUAGAAAUAGGUCCdCCUdCC |
| 091 | Alpha-CGRP from sus scorfa | L-peptide | SCNTATCVTHRLAGLLSRSGGMVKSNFVPTDVGSEAF |
| 092 | Alpha-CGRP from sheep | L-peptide | SCNTATCVTHRLAGLLSRSGGVVKSNFVPTNVGSQAF |
| 093 | Alpha-CGRP from dog | L-peptide | SCNTATCVTHRLAGLLSRSGGVVKNNFVPTNVGSEAF |
| 094 | r-Amylin | L-peptide | KCNTATCATQRLANFLVRSSNNFGAILSPTNVGSNTY |
| 095 | | L-RNA | HWRUYGGAKACUMMBYNYNRVKKRGADAUARRUYCCBUCC |
| 096 | | L-RNA | CUGUYGGAGACUMMUBDYHRVKKAGADAUAGGUYCCCUCC |
| 097 | | L-RNA | CUGUCGGAGACUACUCRYHGRGUAGAAAUAGGUCCCCUCC |
| 098 | | L-RNA | CUGUCGGAGACUACUCGUCGAGUAGAAAUAGGUCCCCUCC |

| SEQ ID NO. | | SEQUENCE |
|---|---|---|
| 099 | L-RNA/L-DNA | HWn$_1$n$_2$YGGAn$_3$An$_4$UMn$_5$n$_6$Yn$_7$n$_8$n$_9$n$_{10}$n$_{11}$Kn$_{12}$Rn$_{13}$ADn$_{14}$n$_{15}$ARn$_{16}$Un$_{17}$Cn$_{18}$n$_{19}$Un$_{20}$n$_{21}$<br>n$_1$ is R or dG, n$_2$ is U or dT, n$_3$ is K or dG, n$_4$ is C or dC, n$_5$ is M or dC, n$_6$ is B or dU, n$_7$ is N or dG, n$_8$ is Y or dT, n$_9$ is N or dC, n$_{10}$ is R or dG, n$_{11}$ is V or dA, n$_{12}$ is K or dT or dU, n$_{13}$ is G or dG, n$_{14}$ is A or dA, n$_{15}$ is U or dT, n$_{16}$ is R or dG, n$_{17}$ is Y or dC, n$_{18}$ is C or dC, n$_{19}$ is B or dC, n$_{20}$ is C or dC, n$_{21}$ is C or dC |
| 100 | L-RNA/L-DNA | CUn$_1$n$_2$YGGAn$_3$An$_4$UMn$_5$n$_6$Bn$_7$n$_8$n$_9$n$_{10}$n$_{11}$Kn$_{12}$An$_{13}$ADn$_{14}$n$_{15}$AGn$_{16}$Un$_{17}$Cn$_{18}$n$_{19}$Un$_{20}$n$_{21}$<br>n$_1$ is G or dG, n$_2$ is U or dT, n$_3$ is G or dG, n$_4$ is C or dC, n$_5$ is M or dC, n$_6$ is B or dU, n$_7$ is D or dG, n$_8$ is Y or dT, n$_9$ is H or dC, n$_{10}$ is R or dG, n$_{11}$ is V or dA, n$_{12}$ is K or dT or dU, n$_{13}$ is G or dG, n$_{14}$ is A or dA, n$_{15}$ is U or dT, n$_{16}$ is G or dG, n$_{17}$ is Y or dC, n$_{18}$ is C or dC, n$_{19}$ is C or dC, n$_{20}$ is C or dC, n$_{21}$ is C or dC |
| 101 | L-RNA/L-DNA | CUn$_1$n$_2$CGGAn$_3$An$_4$UAn$_5$n$_6$Cn$_7$n$_8$n$_9$n$_{10}$n$_{11}$Gn$_{12}$An$_{13}$AAn$_{14}$n$_{15}$AGn$_{16}$Un$_{17}$Cn$_{18}$n$_{19}$Un$_{20}$n$_{21}$<br>n$_1$ is G or dG, n$_2$ is U or dT, n$_3$ is G or dG, n$_4$ is C or dC, n$_5$ is C or dC, n$_6$ is U or dU, n$_7$ is R or dG, n$_8$ is Y or dT, n$_9$ is H or dC, n$_{10}$ is G or dG, n$_{11}$ is R or dA, n$_{12}$ is U or dT or dU, n$_{13}$ is G or dG, n$_{14}$ is A or dA, n$_{15}$ is U or dT, n$_{16}$ is G or dG, n$_{17}$ is C or dC, n$_{18}$ is C or dC, n$_{19}$ is C or dC, n$_{20}$ is C or dC, n$_{21}$ is C or dC |
| 102 | L-RNA/L-DNA | CUn$_1$n$_2$CGGAn$_3$An$_4$UAn$_5$n$_6$Cn$_7$n$_8$n$_9$n$_{10}$n$_{11}$Gn$_{12}$An$_{13}$AAn$_{14}$n$_{15}$AGn$_{16}$Un$_{17}$Cn$_{18}$n$_{19}$Un$_{20}$n$_{21}$<br>n$_1$ is G or dG, n$_2$ is U or dT, n$_3$ is G or dG, n$_4$ is C or dC, n$_5$ is C or dC, n$_6$ is U or dU, n$_7$ is G or dG, n$_8$ is U or dT, n$_9$ is C or dC, n$_{10}$ is G or dG, n$_{11}$ is A or dA, n$_{12}$ is U or dT or dU, n$_{13}$ is G or dG, n$_{14}$ is A or dA, n$_{15}$ is U or dT, n$_{16}$ is G or dG, n$_{17}$ is C or dC, n$_{18}$ is C or dC, n$_{19}$ is C or dC, n$_{20}$ is C or dC, n$_{21}$ is C or dC |
| 103 | L-RNA/L-DNA | CUdGUCGGAGACUACUCGUCGAGUAGAAAUAGGUCCCCUCC |
| 104 | L-RNA/L-DNA | CUGdTCGGAGACUACUCGUCGAGUAGAAAUAGGUCCCCUCC |
| 105 | L-RNA/L-DNA | CUGUCGGAdGACUACUCGUCGAGUAGAAAUAGGUCCCCUCC |
| 106 | L-RNA/L-DNA | CUGUCGGAGAdCUACUCGUCGAGUAGAAAUAGGUCCCCUCC |
| 107 | L-RNA/L-DNA | CUGUCGGAGACUAdCUCGUCGAGUAGAAAUAGGUCCCCUCC |
| 108 | L-RNA/L-DNA | CUGUCGGAGACUACUCdGUCGAGUAGAAAUAGGUCCCCUCC |
| 109 | L-RNA/L-DNA | CUGUCGGAGACUACUCGdTCGAGUAGAAAUAGGUCCCCUCC |
| 110 | L-RNA/L-DNA | CUGUCGGAGACUACUCGUdCGAGUAGAAAUAGGUCCCCUCC |

TABLE 1-continued

| 111 | L-RNA/L-DNA | CUGUCGGAGACUACUCGUCdGAGUAGAAAUAGGUCCCCUCC |
| 112 | L-RNA/L-DNA | CUGUCGGAGACUACUCGUCGdAGUAGAAAUAGGUCCCCUCC |
| 113 | L-RNA/L-DNA | CUGUCGGAGACUACUCGUCGAGdTAGAAAUAGGUCCCCUCC |
| 114 | L-RNA/L-DNA | CUGUCGGAGACUACUCGUCGAGUAdGAAAUAGGUCCCCUCC |
| 115 | L-RNA/L-DNA | CUGUCGGAGACUACUCGUCGAGUAGAAdAUAGGUCCCCUCC |

| SEQ ID NO. | Internal Reference | | Sequence |
|---|---|---|---|
| 116 | | L-RNA/L-DNA | CUGUCGGAGACUACUCGUCGAGUAGAAAdTAGGUCCCCUCC |
| 117 | | L-RNA/L-DNA | CUGUCGGAGACUACUCGUCGAGUAGAAAUAGdGUCCCCUCC |
| 118 | | L-RNA/L-DNA | CUGUCGGAGACUACUCGUCGAGUAGAAAUAGGUdCCCCUCC |
| 119 | | L-RNA/L-DNA | CUGUCGGAGACUACUCGUCGAGUAGAAAUAGGUCCdCCUCC |
| 120 | | L-RNA/L-DNA | CUGUCGGAGACUACUCGUCGAGUAGAAAUAGGUCCCdCUCC |
| 121 | | L-RNA/L-DNA | CUGUCGGAGACUACUCGUCGAGUAGAAAUAGGUCCCCUdCC |
| 122 | | L-RNA/L-DNA | CUGUCGGAGACUACUCGUCGAGUAGAAAUAGGUCCCCUCdC |
| 123 | | L-RNA/L-DNA | CUGUCGGAGACUACUCGUCGAGUAGAAAUAGGUCCdCCUdCC |
| 124 | 226-F2-001-D41-dU20 | L-RNA/L-DNA | CCGUGCUGUCGGAGACUACdUCGUCGAGUAGAAAUAGGUCCdCCUCCCACGG |
| 125 | 226-F2-001-D41-dU28 | L-RNA/L-DNA | CCGUGCUGUCGGAGACUACUCGUCGAGdUAGAAAUAGGUCCdCCUCCCACGG |
| 126 | 226-F2-001-D41-dU20-28 | L-RNA/L-DNA | CCGUGCUGUCGGAGACUACdUCGUCGAGdUAGAAAUAGGUCCdCCUCCCACGG |
| 127 | 226-F2-001-D41/D44-dU20 | L-RNA/L-DNA | CCGUGCUGUCGGAGACUACdUCGUCGAGUAGAAAUAGGUCCdCCUdCCCACGG |
| 128 | 226-F2-001-D41/D44-dU28 | L-RNA/L-DNA | CCGUGCUGUCGGAGACUACUCGUCGAGdUAGAAAUAGGUCCdCCUdCCCACGG |
| 129 | 226-F2-001-D41/D44-dU20-28 | L-RNA/L-DNA | CCGUGCUGUCGGAGACUACdUCGUCGAGdUAGAAAUAGGUCCdCCUdCCCACGG |
| 130 | | L-RNA/L-DNA | CUGUCGGAGACUACdUCGUCGAGUAGAAAUAGGUCCdCCUCC |
| 131 | | L-RNA/L-DNA | CUGUCGGAGACUACUCGUCGAGdUAGAAAUAGGUCCdCCUCC |
| 132 | | L-RNA/L-DNA | CUGUCGGAGACUACdUCGUCGAGdUAGAAAUAGGUCCdCCUCC |
| 133 | | L-RNA/L-DNA | CUGUCGGAGACUACdUCGUCGAGUAGAAAUAGGUCCdCCUdCC |
| 134 | | L-RNA/L-DNA | CUGUCGGAGACUACUCGUCGAGdUAGAAAUAGGUCCdCCUdCC |
| 135 | | L-RNA | 5'-40kDa-PEG-GGACUGAUGGCGCGGUCCUAUUACGCCGAUAGGGUGAGGGGA |

The present invention is further illustrated by the figures, examples and the sequence listing from which further features, embodiments and advantages may be taken, wherein FIG. 1A-B show an alignment of sequences of CGRP binding nucleic acid molecules of the invention and relative activity to human alpha-CGRP in a competition binding assay;

FIG. 2 shows derivatives of CGRP binding nucleic acid molecule 226-F2-001 with different first and second terminal stretches;

FIG. 3A-D shows derivatives of CGRP binding nucleic acid molecule 226-F2-001 including the $K_D$ value and relative binding activity to human alpha-CGRP as determined by surface plasmon resonance measurement;

FIG. 4 is a diagram showing the kinetic evaluation by Biacore measurement of CGRP binding Spiegelmers 226-F2-001 and 226-F2-001-D41 to immobilized human alpha-CGRP, whereby the data for 1000, 500, 250, 125, 62.5, 31.25, 15.63, 7.8, 3.9, 1.95 and 0 nM of Spiegelmers 226-F2-001 and 226-F2-001-D41 are indicated as response units;

FIG. 5 is a diagram showing the kinetic evaluation by Biacore measurement of CGRP binding Spiegelmers 226-F2-001 and 226-F2-001-D44 to immobilized human alpha-CGRP, whereby the data for 1000, 500, 250, 125, 62.5, 31.25, 15.63, 7.8, 3.9, 1.95 and 0 nM of Spiegelmers 226-F2-001 and 226-F2-001-D44 are indicated as response units;

FIG. 6 is a diagram showing the kinetic evaluation by Biacore measurement of CGRP binding Spiegelmers 226-F2-001-D41 and 226-F2-001-D41/44 to immobilized human alpha-CGRP, whereby the data for 1000, 500, 250, 125, 62.5, 31.25, 15.63, 7.8, 3.9, 1.95 and 0 nM of Spiegelmers 226-F2-001-D41 and 226-F2-001-D41/44 are indicated as response units;

FIG. 7A is a diagram showing inhibition of human alpha-CGRP-induced cAMP production by CGRP binding Spiegelmers 212-G1-001 (black diamonds) and 226-F2-001 (black circles), whereby a) the generated amounts of cAMP per well were normalized to the largest value of each data set and depicted as percent activity against Spiegelmer concentration, b) the Spiegelmer concentrations at which cAMP production is inhibited by 50% ($IC_{50}$) were calculated using nonlinear regression (four parameter fit) with Prism5 software, c) the $IC_{50}$ values for 212-G1-001 and 226-F2-001 determined were 8.7 nM and 3.5 nM, respectively;

FIG. 7B is a diagram showing inhibition of human CGRP-induced cAMP production by CGRP binding Spiegelmers 226-F2-001-5'40 kDa-PEG (black circles) and NOX-L41 (also referred to as 226-F2-001-D41-5'40 kDa-PEG, black squares), whereby a) the generated amounts of cAMP per well were normalized to the largest value of each data set and depicted as percent activity against Spiegelmer concentration, b) the Spiegelmer concentrations at which cAMP production is inhibited by 50% ($IC_{50}$) were calculated using nonlinear regression (four parameter fit) with Prism5 software, c) the $IC_{50}$ values for 226-F2-001-5'40 kDa-PEG and NOX-L41 determined were 3.8 nM and 0.39 nM, respectively;

FIG. 8A shows an amino acid sequence alignment of human alpha-CGRP, human beta-CGRP, human amylin, human calcitonin, human adrenomedullin and human intermedin;

FIG. 8B shows an amino acid sequence alignment of alpha-CGRP from human, *macaca mulatta*, rat, mouse, sus scorfa, sheep and dog;

FIG. 9 shows an amino acid sequence alignment of human and rat CGRP and human and rat amylin; $IC_{50}$ values determined by in vitro assay with the human CGRP receptor and dissociation constants $K_D$ determined by kinetic Biacore measurement for CGRP binding Spiegelmers NOX-L41 (also referred to as 226-F2-001-D41-5'40 kDa-PEG) and 226-F2-001-D41;

Figure 4:
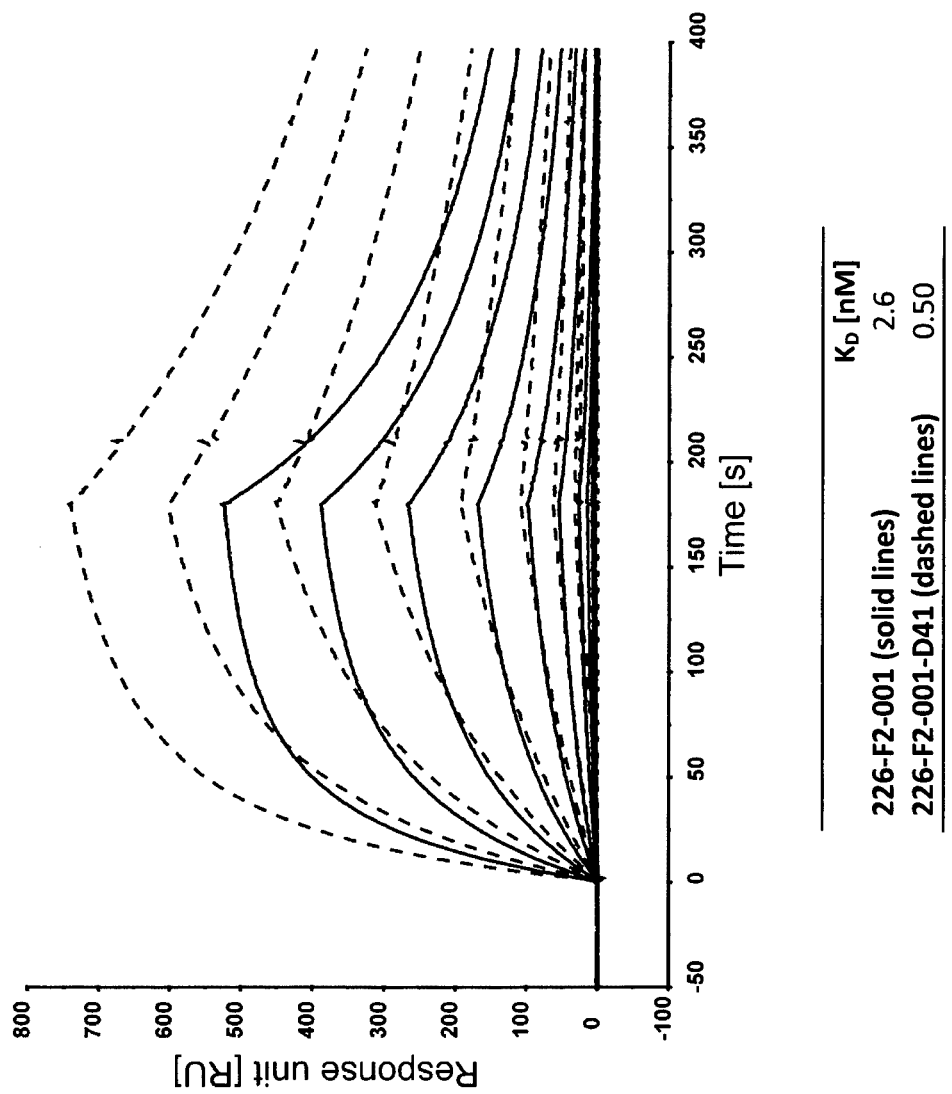
Figure 5:
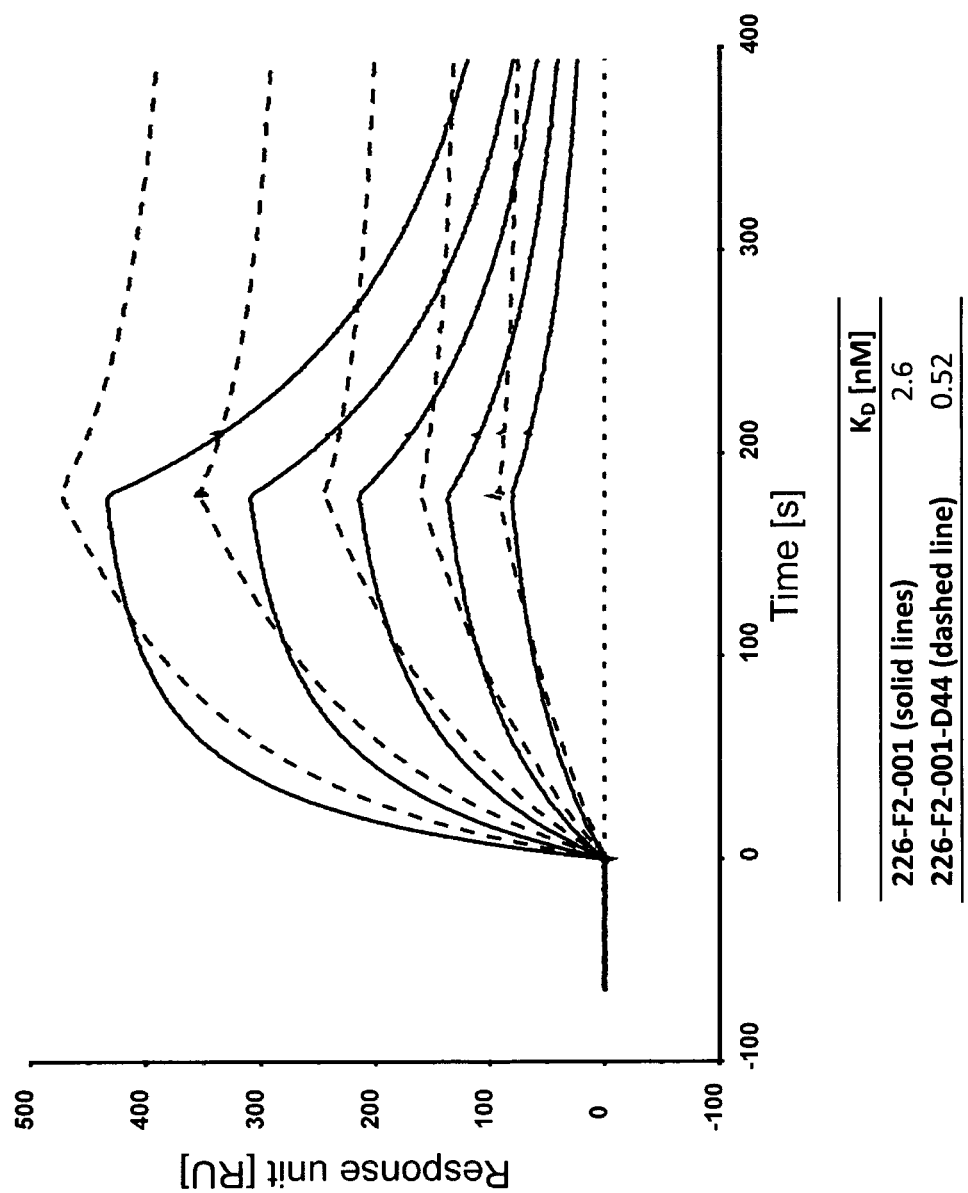
Figure 6:
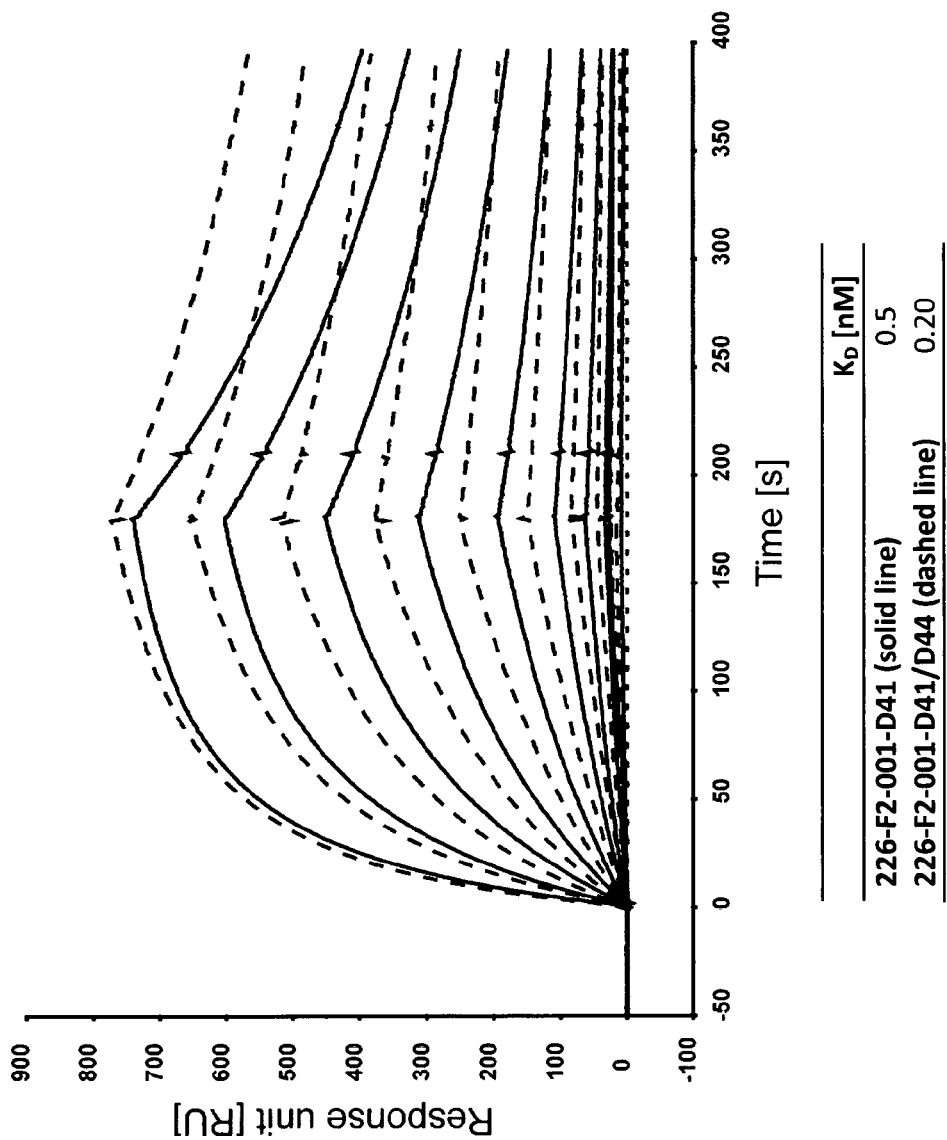
Figure 10:
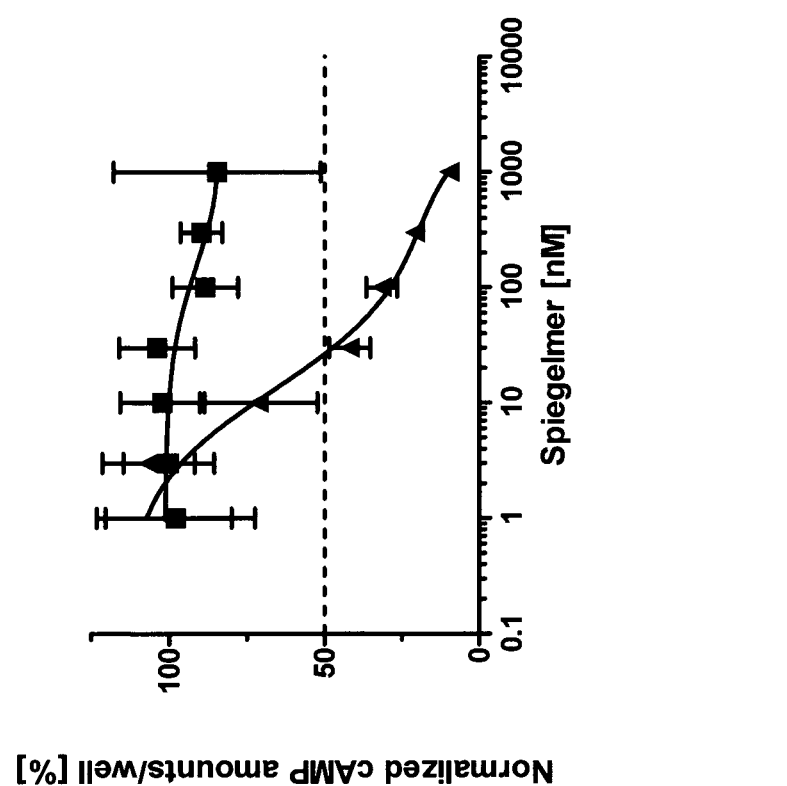
Figure 11B:
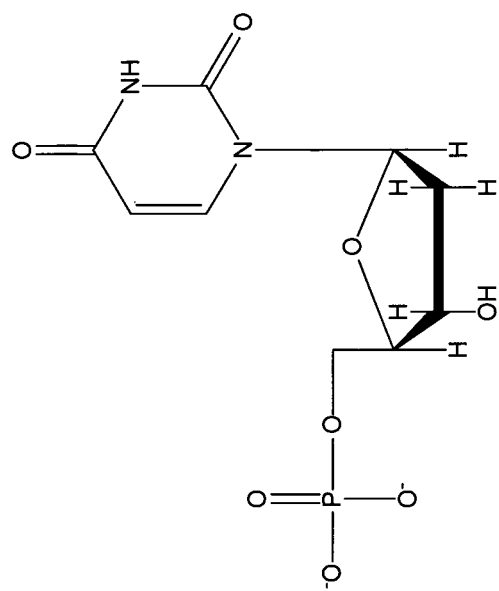
Figure 13:
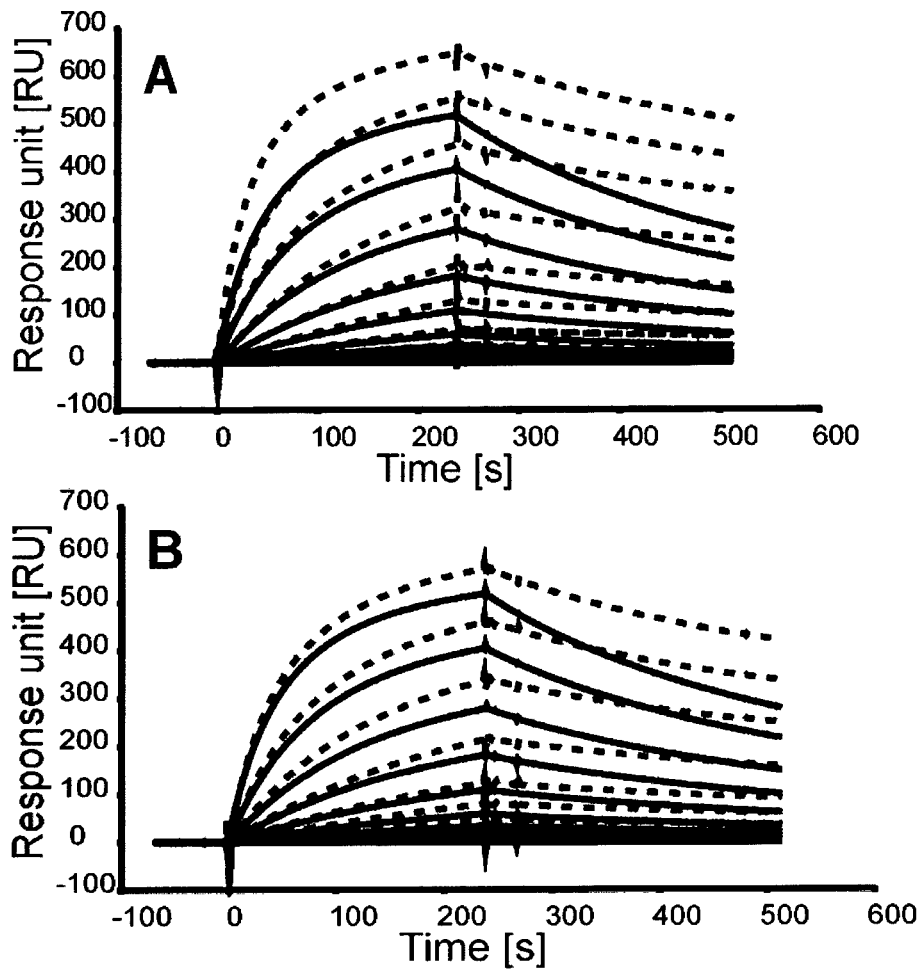

FIG. 10 is a diagram showing inhibition of human amylin-induced cAMP production by CGRP-binding Spiegelmer NOX-L41 (also referred to as 226-F2-001-D41-5'40 kDa-PEG, black squares) and an amylin-binding control Spiegelmer (black triangles), whereby the generated amounts of cAMP per well were normalized to the largest value of each data set and depicted as percent activity against Spiegelmer concentration;

FIG. 11A-B shows the 2'deoxyribonucleotides that the nucleic acid molecules according to the present invention consist of FIG. 12 shows the ribonucleotides that the nucleic acid molecules according to the present invention consist of FIG. 13 is a diagram showing the kinetic evaluation by Biacore measurement of CGRP binding Spiegelmers 226-F2-001-D41, 226-F2-001-D41-dU20 and 226-F2-001-D41-dU28 to immobilized human CGRP, whereby the data for 500-250-125-62.5-31.3-15.6-7.8(2×)-3.9-1.95-0.98-0.48-0 nM of Spiegelmers 226-F2-001-D41, 226-F2-001-D41-dU20 and 226-F2-001-D41-dU28 are indicated as response units.

EXAMPLE 1

Nucleic Acid Molecules Capable of Specifically Binding CGRP

Several CGRP binding nucleic acid molecules and derivatives thereof were identified: the nucleotide sequences of which are depicted in FIGS. 1 to 3. The binding affinity of CGRP binding nucleic acid molecules to human alpha-CGRP and their antagonistic function with regard to the interaction human alpha-CGRP and the CGRP receptor were characterized as a) aptamers, i. e. as D-nucleic acid molecules using a comparative competition pull-down assay (Example 3)

b) Spiegelmers, i. e. L-nucleic acid by surface plasmon resonance measurement (Example 4), and by an in vitro assay with cells expressing the human CGRP receptor (Example 5).

The Spiegelmers and aptamers were synthesized as described in Example 2.

The nucleic acid molecules thus generated exhibit slightly different sequences, whereby the sequences can be summarized or grouped as a sequence family.

For definition of ribonucleotide sequence motifs, the IUPAC abbreviations for ambiguous nucleotides are used:

| | | |
|---|---|---|
| S | strong | G or C; |
| W | weak | A or U; |
| R | purine | G or A; |
| Y | pyrimidine | C or U; |
| K | keto | G or U; |
| M | imino | A or C; |
| B | not A | C or U or G; |
| D | not C | A or G or U; |
| H | not G | A or C or U; |
| V | not U | A or C or G; |
| N | all | A or G or C or U. |

For differentiation between the 2'-deoxyribonucleotides and the ribonucleotides the following abbreviations are used:

For 2'-deoxyribonucleotides: dG, dC, dT, dA and dU (see FIGS. 11A and 11B).

For ribonucleotides: G, C, T, U (see FIG. 12).

If not indicated to the contrary, any nucleic acid sequence or sequence of stretches, respectively, is indicated in the 5'→3' direction.

As depicted in FIGS. 1 to 3 CGRP binding nucleic acid molecules comprise one central stretch of nucleotides defining a potential CGRP binding motif, whereby FIG. 1 (FIGS. 1 A and 1B) shows the different sequences of the sequence family and FIGS. 2 to 3 show derivatives of nucleic acid molecule 226-F2-001.

In general, CGRP binding nucleic acid molecules comprise at the 5'-end and the 3'-end terminal stretches of nucleotides: the first terminal stretch of nucleotides and the second terminal stretch of nucleotides. The first terminal stretch of nucleotides and the second terminal stretch of nucleotides can hybridize to each other, whereby upon hybridization a double-stranded structure is formed. However, such hybridization is not necessarily given in the molecule in vivo and/or in vitro.

The three stretches of nucleotides of CGRP binding nucleic acid molecules—the first terminal stretch of nucleotides, the central stretch of nucleotides and the second terminal stretch of nucleotides—are arranged to each other in 5'→3'-direction: the first terminal stretch of nucleotides—the central stretch of nucleotides—the second terminal stretch of nucleotides. However, alternatively, the first terminal stretch of nucleotides, the central stretch of nucleotides and the second terminal stretch of nucleotides are arranged to each other in 5'→3'-direction: the second terminal stretch of nucleotides—the central stretch of nucleotides—the first terminal stretch of nucleotides.

The sequences of the defined stretches may be different between the CGRP binding nucleic acid molecules which influences the binding affinity to CGRP, preferably human alpha-CGRP. Based on binding analysis of the different CGRP binding nucleic acid molecules the central stretch of nucleotides and their nucleotide sequences as described in the following are individually and more preferably in their entirety essential for binding to CGRP, preferably human alpha-CGRP.

The CGRP binding nucleic acid molecules according to the present invention as shown in FIGS. 1A and 1B consist of ribonucleotides. CGRP binding nucleic acid molecule 212-G1-001 has a binding affinity with a $K_D$ of 5.12 nM for human alpha-CGRP (determined by plasmon resonance measurement, see Example 4). CGRP binding nucleic acid molecules 226-F2-001, 212-F1-001, 224-B2-001, 224-E1-001, 226-A2-002, 226-A3-001, 226-G2-002, 226-G1-002, 226-C2-002, 226-E1-002, 226-F1-001, 226-C3-001, 231-A1-001, 231-02-001, 231-C1-001, 231-C2-001, 231-D1-001, 231-F1-001, 231-E1-001, 231-B3-001, 231-A2-001, 231-E2-001 and 231-H2-001 were tested in a comparative competition pull-down assay vs. CGRP binding nucleic acid 212-G1-001 for their ability to bind human alpha-CGRP (see Example 3, FIGS. 1A and 1B).

CGRP binding nucleic acid molecules 226-F2-001, 226-A3-001, 226-C3-001, 231-A1-001, 231-C1-001, 231-C2-001, 231-F1-001, 231-E1-001, 231-A2-001 and 231-E2-001 showed better binding affinity than 212-G1-001. CGRP binding nucleic acid molecules 212-F1-001, 224-B2-001, 224-E1-001, and 226-F1-001 showed binding affinity similar to 212-G1-001. CGRP binding nucleic acid molecules 226-A2-002, 226-G2-002, 226-C2-002, 226-E1-002, 231-G2-001, 231-D1-001, 231-B3-001 and 231-H2-001 showed weaker binding affinity than 212-G1-001 (FIGS. 1A and 1B).

The CGRP binding nucleic acid molecules 212-G1-001, 226-F2-001, 212-F1-001, 224-B2-001, 224-E1-001, 226-A2-002, 226-A3-001, 226-02-002, 226-C2-002, 226-E1-002, 226-F1-001, 226-C3-001, 231-A1-001, 231-02-001, 231-C1-001, 231-C2-001, 231-D1-001, 231-F1-001, 231-E1-001, 231-B3-001, 231-A2-001, 231-E2-001 and 231-H2-001 consist of ribonucleotides and share the sequence

[SEQ ID NO: 95]
5' HWRUYGGAKACUMMBYNYNRVKKRGADAUARRUYCCBUCC 3'.

The CGRP binding nucleic acid molecules 226-F2-001, 212-F1-001, 224-B2-001, 224-E1-001, 226-A3-001, 226-F1-001, 226-C3-001, 231-A1-001, 231-C1-001, 231-C2-001, 231-F1-001, 231-E1-001, 231-A2-001 and 231-E2-001 showed the similar or better binding affinity to human alpha-CGRP than 212-G1-001 and share the sequence

[SEQ ID NO: 96]
5' CUGUYGGAGACUMMUBDYHRVKKAGADAUAGGUYCCCUCC 3'.

The CGRP binding nucleic acid molecules 226-F2-001, 226-A3-001, 226-C3-001, 231-A1-001, 231-C1-001, 231-C2-001, 231-F1-001, 231-E1-001, 231-A2-001 and 231-E2-001 showed the best binding affinity to human alpha-CGRP and share the sequence

[SEQ ID NO: 97]
5' CUGUCGGAGACUACUCRYHGRGUAGAAAUAGGUCCCCUCC 3', whereby the sequence

[SEQ ID NO: 98]
5' CUGUCGGAGACUACUCGUCGAGUAGAAAUAGGUCCCCUCC 3' is the preferred embodiment thereof.

The inventors surprisingly found that the binding affinity of CGRP binding nucleic acid molecule 226-F2-001 to human alpha-CGRP was improved by replacing ribonucleotides by 2'-deoxyribonucleotides within the sequence of the central stretch of nucleotides, and the first and the second terminal stretch of nucleotides. In particular, replacing up to two ribonucleotides by 2'-deoxyribonucleotides in the CGRP binding nucleic acid molecule 226-F2-001 resulted in improved binding affinity to human alpha-CGRP as determined by plasmon resonance measurement (for protocol, see Example 4. In more detail, the inventors have surprisingly found that a) replacing one ribonucleotide by one 2'-deoxyribonucleotide at position 3, 4, 9, 11, 14, 15, 17, 18, 19, 20, 21, 23, 25, 28, 29, 32, 34, 36, 37, 39 and 40 in the central stretch of nucleotides of CGRP binding nucleic acid molecule 226-F2-001 resulted in improved binding affinity to human CGRP in comparison to the binding affinity of CGRP binding nucleic acid molecule 226-F2-001 (see FIGS. 3A, 3B, 3C and 3D; Spiegelmers 226-F2-001-D08, 226-F2-001-D09, 226-F2-001-D14, 226-F2-001-D16, 226-F2-001-D19, 226-F2-001-D22, 226-F2-001-D23, 226-F2-001-D24, 226-F2-001-D25, 226-F2-001-D26, 226-F2-001-D28, 226-F2-001-D30, 226-F2-001-D33, 226-F2-001-D34, 226-F2-001-D37, 226-F2-001-D39, 226-F2-001-D41, 226-F2-001-D42, 226-F2-001-D44, 226-F2-001-D45, 226-F2-001-dU-20 and 226-F2-001-dU-28);

b) replacing one ribonucleotide by one 2'-deoxyribonucleotide at position 3 or 5 or in the first terminal stretch of nucleotides of CGRP binding nucleic acid molecule 226-F2-001 resulted in improved binding affinity to human CGRP in comparison to the binding affinity of CGRP binding nucleic acid molecule 226-F2-001 (see FIG. 3A; Spiegelmers 226-F2-001-D03 and 226-F2-011-D05);

c) replacing one ribonucleotide by one 2'-deoxyribonucleotide at any position in the second terminal stretch of nucleotides of CGRP binding nucleic acid molecule 226-F2-001 resulted in improved binding affinity to human CGRP in comparison to the binding affinity of CGRP binding nucleic acid molecule 226-F2-001 (see FIGS. 3A and 3C; Spiegelmers 226-F2-001-D46, 226-F2-001-D47, 226-F2-001-D48, 226-F2-001-D49, 226-F2-001-D50);

d) replacing two ribonucleotides by two 2'-deoxyribonucleotides at position 36 and 39 or at position 36 and 15 or at position 36 and 23 in the central stretch of nucleotides of CGRP binding nucleic acid molecule 226-F2-001 resulted in improved binding affinity to human CGRP in comparison to the binding affinity of CGRP binding nucleic acid molecule 226-F2-001 (see FIGS. 3A, 3C and 3D; Spiegelmers 226-F2-001-D41/44, 226-F2-001-D41-dU-20 and 226-F2-001-D41-dU28);

e) replacing three ribonucleotides by three 2'-deoxyribonucleotides at position 36, 39 and 15 or at position 36, 39 and 23 in the central stretch of nucleotides of CGRP binding nucleic acid molecule 226-F2-001 resulted in improved binding affinity to human CGRP in comparison to the binding affinity of CGRP binding nucleic acid molecule 226-F2-001 (see FIG. 3D; Spiegelmers 226-F2-001-D41/D44-dU20, 226-F2-001-D41/D44-dU28).

Based on the data shown that replacing ribonucleotides by 2'-deoxyribonucleotides at several positions of the central stretch of nucleotides of CGRP binding nucleic acid molecules lead to improved binding to human alpha-CGRP the central stretch of all tested CGRP binding nucleic acid molecules can be summarized in the following generic formula

[SEQ ID NO: 99]
5' HWn$_1$n$_2$YGGAn$_3$An$_4$UMn$_5$n$_6$Yn$_7$n$_8$n$_9$n$_{10}$n$_{11}$Kn$_{12}$Rn$_{13}$ADn$_{14}$n$_{15}$ARn$_{16}$Un$_{17}$Cn$_{18}$n$_{19}$Un$_{20}$n$_{21}$ 3', wherein H, W, Y, G, A, U, M, B, K, R, D, C are ribonucleotides, and n$_1$ is R or dG, n$_2$ is U or dT, n$_3$ is K or dG, n$_4$ is C or dC, n$_5$ is M or dC, n$_6$ is B or dU, n$_7$ is N or dG, n$_8$ is Y or dT, n$_9$ is N or dC, n$_{10}$ is R or dG, n$_{11}$ is V or dA, n$_{12}$ is K or dT or dU, n$_{13}$ is G or dG, n$_{14}$ is A or dA, n$_{15}$ is U or dT, n$_{16}$ is R or dG, n$_{17}$ is Y or dC, n$_{18}$ is C or dC, n$_{19}$ is B or dC, n$_{20}$ is C or dC, n$_{21}$ is C or dC, and dG, dT, dC, dA and dU are 2'-deoxyribonucleotides.

The generic formula

[SEQ ID NO: 100]
5' CUn$_1$n$_2$YGGAn$_3$An$_4$UMn$_5$n$_6$Bn$_7$n$_8$n$_9$n$_{10}$n$_{11}$Kn$_{12}$An$_{13}$ADn$_{14}$n$_{15}$AGn$_{16}$Un$_{17}$Cn$_{18}$n$_{19}$Un$_{20}$n$_{21}$ 3' summarizes the sequences of the central stretches of the CGRP binding nucleic acid molecules 226-F2-001 and derivatives thereof, 212-F1-001, 224-B2-001, 224-E1-001, 226-A3-001, 226-F1-001, 226-C3-001, 231-A1-001, 231-C1-001, 231-C2-001, 231-F1-001, 231-E1-001, 231-A2-00 and 231-E2-001 that showed similar or better binding affinity to human alpha-CGRP than 212-G1-001, wherein C, U, Y, G, A, M, B, Y, H, K, D, R and V are ribonucleotides, and n$_1$ is G or dG, n$_2$ is U or dT, n$_3$ is G or dG, n$_4$ is C or dC, n$_5$ is M or dC, n$_6$ is B or dU, n$_7$ is D or dG, n$_8$ is Y or dT, n$_9$ is H or dC, n$_{10}$ is R or dG, n$_{11}$ is V or dA, n$_{12}$ is K or dT or dU, n$_{13}$ is G or dG, n$_{14}$ is A or dA, n$_{15}$ is U or dT, n$_{16}$ is G or dG, n$_{17}$ is Y or dC, n$_{18}$ is C or dC, n$_{19}$ is C or dC, n$_{20}$ is C or dC, n$_{21}$ is C or dC, and dG, dT, dC, dA and dU are 2'-deoxyribonucleotides.

The generic formula

[SEQ ID NO: 101]
5' CUn$_1$n$_2$CGGAn$_3$An$_4$An$_5$n$_6$Cn$_7$n$_8$n$_9$n$_{10}$n$_{11}$Gn$_{12}$An$_{13}$AAn$_{14}$n$_{15}$AGn$_{16}$Un$_{17}$Cn$_{18}$n$_{19}$Un$_{20}$n$_{21}$ 3' summarizes the sequences of the central stretches of the CGRP binding nucleic acid molecules with the best binding affinity for CGRP (Spiegelmer 226-F2-001 and derivatives thereof, and Spiegelmers 226-A3-001, 226-C3-001, 231-A1-001, 231-C1-001, 231-C2-001, 231-F1-001, 231-E1-001, 231-A2-001 and 231-E2-001)

wherein C, U, Y, G, A, H and R are ribonucleotides, and n$_1$ is G or dG, n$_2$ is U or dT, n$_3$ is G or dG, n$_4$ is C or dC, n$_5$ is C or dC, n$_6$ is U or dU, n$_7$ is R or dG, n$_8$ is Y or dT, n$_9$ is H or dC, n$_{10}$ is G or dG, n$_{11}$ is R or dA, n$_{12}$ is U or dT or dU, n$_{13}$ is G or dG, n$_{14}$ is A or dA, n$_{15}$ is U or dT, n$_{16}$ is G or dG, n$_{17}$ is C or dC, n$_{18}$ is C or dC, n$_{19}$ is C or dC, n$_{20}$ is C or dC, n$_{21}$ is C or dC, and dG, dT, dC, dA and dU are 2'-deoxyribonucleotides.

The central stretches of nucleotides of CGRP binding nucleic acid 226-F2-001 and its derivatives that show, due to replacing ribonucleotides by 2'-deoxyribonucleotides at several positions of the central stretch of nucleotides, improved binding to CGRP in comparison to 226-F2-001, can be summarized in the following generic formula:

[SEQ ID NO: 102]
5' CUn$_1$n$_2$CGGAn$_3$An$_4$UAn$_5$n$_6$Cn$_7$n$_8$n$_9$n$_{10}$n$_{11}$Gn$_{12}$An$_{13}$AAn$_{14}$n$_{15}$AGn$_{16}$Un$_{17}$Cn$_{18}$n$_{19}$Un$_{20}$n$_{21}$ 3' wherein C, U, G, A, are ribonucleotides, and n$_1$ is G or dG, n$_2$ is U or dT, n$_3$ is G or dG, n$_4$ is C or dC, n$_5$ is C or dC, n$_6$ is U or dU, n$_7$ is G or dG, n$_8$ is U or dT, n$_9$ is C or dC, n$_{10}$ is G or dG, n$_{11}$ is A or dA, n$_{12}$ is U or dT or dU, n$_{13}$ is G or dG, n$_{14}$ is A or dA, n$_{15}$ is U or dT, n$_{16}$ is G or dG, n$_{17}$ is C or dC, n$_{18}$ is C or dC, n$_{19}$ is C or dC, n$_{20}$ is C or dC, n$_{21}$ is C or dC, and dG, dT, dC, dA and dU are 2'-deoxyribonucleotides, wherein in a preferred embodiment the central stretch of nucleotides comprise the sequence (1)
[SEQ ID NO: 103]
5' CUdGUCGGAGACUACUCGUCGAGUAGAAAUAGGUCCCCUCC 3', (2)
[SEQ ID NO: 104]
5' CUGdTCGGAGACUACUCGUCGAGUAGAAAUAGGUCCCCUCC 3', (3)
[SEQ ID NO: 105]
5' CUGUCGGAdGACUACUCGUCGAGUAGAAAUAGGUCCCCUCC 3', (4)
[SEQ ID NO: 106]
5' CUGUCGGAGAdCUACUCGUCGAGUAGAAAUAGGUCCCCUCC 3', (5)
[SEQ ID NO: 107]
5' CUGUCGGAGACUAdCUCGUCGAGUAGAAAUAGGUCCCCUCC 3', (6)
[SEQ ID NO: 108]
5' CUGUCGGAGACUACUCdGUCGAGUAGAAAUAGGUCCCCUCC 3', (7)
[SEQ ID NO: 109]
5' CUGUCGGAGACUACUCGdTCGAGUAGAAAUAGGUCCCCUCC 3', (8)
[SEQ ID NO: 110]
5' CUGUCGGAGACUACUCGUdCGAGUAGAAAUAGGUCCCCUCC 3', (9)
[SEQ ID NO: 111]
5' CUGUCGGAGACUACUCGUCdGAGUAGAAAUAGGUCCCCUCC 3',

(10)
[SEQ ID NO: 112]
5' CUGUCGGAGACUACUCGUCGdAGUAGAAAUAGGUCCCCUCC 3',

(11)
[SEQ ID NO: 113]
5' CUGUCGGAGACUACUCGUCGAGdTAGAAAUAGGUCCCCUCC 3',

(12)
[SEQ ID NO: 114]
5' CUGUCGGAGACUACUCGUCGAGUAdGAAAUAGGUCCCCUCC 3'

(13)
[SEQ ID NO: 115]
5' CUGUCGGAGACUACUCGUCGAGUAGAAdAUAGGUCCCCUCC 3'

(14)
[SEQ ID NO: 116]
5' CUGUCGGAGACUACUCGUCGAGUAGAAAdTAGGUCCCCUCC 3',

(15)
[SEQ ID NO: 117]
5' CUGUCGGAGACUACUCGUCGAGUAGAAAUAGdGUCCCCUCC 3',

(16)
[SEQ ID NO: 118]
5' CUGUCGGAGACUACUCGUCGAGUAGAAAUAGGU<u>dc</u>CCCUCC 3',

(17)
[SEQ ID NO: 119]
5' CUGUCGGAGACUACUCGUCGAGUAGAAAUAGGUCC<u>dc</u>CUCC 3',

(18)
[SEQ ID NO: 120]
5' CUGUCGGAGACUACUCGUCGAGUAGAAAUAGGUCCC<u>dc</u>UCC 3',

(19)
[SEQ ID NO: 121]
5' CUGUCGGAGACUACUCGUCGAGUAGAAAUAGGUCCCCU<u>dc</u>C3',

(20)
[SEQ ID NO: 122]
5' CUGUCGGAGACUACUCGUCGAGUAGAAAUAGGUCCCCUC<u>dc</u> 3',

(21)
[SEQ ID NO: 123]
5' CUGUCGGAGACUACUCGUCGAGUAGAAAUAGGUCC<u>dc</u>CU<u>dc</u>C 3',

(22)
[SEQ ID NO: 130]
5' CUGUCGGAGACUAC<u>dU</u>CGUCGAGUAGAAAUAGGUCC<u>dc</u>CUCC 3',

(23)
[SEQ ID NO: 131]
5' CUGUCGGAGACUACUCGUCGAG<u>dU</u>AGAAAUAGGUCC<u>dc</u>CUCC 3',

(24)
[SEQ ID NO: 132]
5' CUGUCGGAGACUAC<u>dU</u>CGUCGAG<u>dU</u>AGAAAUAGGUCC<u>dc</u>CUCC 3',

(25)
[SEQ ID NO: 133]
5' CUGUCGGAGACUAC<u>dU</u>CGUCGAGUAGAAAUAGGUCC<u>dc</u>CU<u>dc</u>C 3',

(26)
[SEQ ID NO: 134]
5' CUGUCGGAGACUACUCGUCGAG<u>dU</u>AGAAAUAGGUCC<u>dc</u>CU<u>dc</u>C 3',

(27)
[SEQ ID NO: 90]
5' CUGUCGGAGACUAC<u>dU</u>CGUCGAG<u>dU</u>AGAAAUAGGUCC<u>dc</u>CU<u>dc</u>C 3', wherein in a more preferred embodiment the central stretch of nucleotides comprise the sequence 5' CUGUCGGAGACUACUCGUCGAGUAGAAAUAGGUCC<u>dc</u>CUCC 3'
(see Spiegelmer 226-F2-001-D41,
[SEQ ID NO: 119]),
or 5' CUGUCGGAGACUACUCGUCGAGUAGAAAUAGGUCC<u>dc</u>CU<u>dc</u>C 3'
(see Spiegelmer 226-F2-001-D41/44,
[SEQ ID NO: 123]),
or 5' CUGUCGGAGACUACUCGUCGAG<u>dU</u>AGAAAUAGGUCC<u>dc</u>CUCC 3'
(see Spiegelmer 226-F2-001-D41-dU28,
[SEQ ID NO: 131]].

The first and the second terminal stretches of CGRP binding nucleic acid molecules of the invention comprise four, five, six or seven nucleotides (FIG. 1 to FIG. 3), whereby the stretches optionally hybridize with each other, whereby upon hybridization a double-stranded structure is formed. This double-stranded structure can consist of one to seven base-pairs. However, such hybridization is not necessarily given in the molecule in vivo and in vitro.

Analyzing the first terminal stretch of nucleotides and the second terminal stretch of nucleotides of all tested CGRP binding nucleic acid molecules the generic formula for the first terminal stretch of nucleotides is 5' $Z_1Z_2Z_3SZ_4WZ_5$ 3' and the generic formula for the second terminal stretch of nucleotides is 5' $Z_6Z_7Z_8Z_9Z_{10}Z_{11}Z_{12}$ 3', wherein
$Z_1$ is S or absent, $Z_2$ is V or absent, $Z_3$ is B or absent, $Z_4$ is V or dG, $Z_5$ is G or dG, $Z_6$ is Y or dC, $Z_7$ is W or dA, $Z_8$ is B or dC, $Z_9$ is S or dG, $Z_{10}$ is S or dG or absent, $Z_{11}$ is B or absent, $Z_{12}$ is K or absent, and
wherein S, W, V, B, Y, and K are ribonucleotides, and
dG, dC and dA are 2'-deoxyribonucleotides,
whereby in a preferred embodiment,
  a) $Z_1$ is S, $Z_2$ is V, $Z_3$ is B, $Z_{10}$ is S or dG, $Z_{11}$ is B, $Z_{12}$ is K,
  b) $Z_1$ is absent, $Z_2$ is V, $Z_3$ is B, $Z_{10}$ is S or dG, $Z_{11}$ is B, $Z_{12}$ is K,
  c) $Z_1$ is S, $Z_2$ is V, $Z_3$ is B, $Z_{10}$ is S or dG, $Z_{11}$ is B, $Z_{12}$ is absent,
  d) $Z_1$ is absent, $Z_2$ is V, $Z_3$ is B, $Z_{10}$ is S or dG, $Z_{11}$ is B, $Z_{12}$ is absent,
  e) $Z_1$ is absent, $Z_2$ is absent, $Z_3$ is B, $Z_{10}$ is S or dG, $Z_{11}$ is B, $Z_{12}$ is absent,
  f) $Z_1$ is absent, $Z_2$ is V, $Z_3$ is B, $Z_{10}$ is S or dG, $Z_{11}$ is absent, $Z_{12}$ is absent
  g) $Z_1$ is absent, $Z_2$ is absent, $Z_3$ is B, $Z_{10}$ is S or dG, $Z_{11}$ is absent, $Z_{12}$ is absent,
  h) $Z_1$ is absent, $Z_2$ is absent, $Z_3$ is absent, $Z_{10}$ is S or dG, $Z_{11}$ is absent, $Z_{12}$ is absent,
  i) $Z_1$ is absent, $Z_2$ is absent, $Z_3$ is B, $Z_{10}$ is absent, $Z_{11}$ is absent, $Z_{12}$ is absent
  j) $Z_1$ is absent, $Z_2$ is absent, $Z_3$ is absent, $Z_{10}$ is absent, $Z_{11}$ is absent, $Z_{12}$ is absent.

The CGRP binding nucleic acid molecules comprising a first and a second terminal stretch consisting of ribonucleotides comprise the following combination of first and second terminal stretches:
  a) the first terminal stretch of nucleotides comprises a nucleotide sequence of 5' CACCGUG 3' and the second terminal stretch of nucleotides comprises a nucleotide sequence of 5' CACGGUG 3'; or
  b) the first terminal stretch of nucleotides comprises a nucleotide sequence of 5' GGCCGUG 3' and the second terminal stretch of nucleotides comprises a nucleotide sequence of 5' CACGGCU 3'; or
  c) the first terminal stretch of nucleotides comprises a nucleotide sequence of 5' GUCAUG 3' and the second terminal stretch of nucleotides comprises a nucleotide sequence of 5' CACGGC 3'; or
  d) the first terminal stretch of nucleotides comprises a nucleotide sequence of 5' GCCAUG 3' and the second terminal stretch of nucleotides comprises a nucleotide sequence of 5' CAUGGC 3'; or
  e) the first terminal stretch of nucleotides comprises a nucleotide sequence of 5' GCCGUG 3' and the second terminal stretch of nucleotides comprises a nucleotide sequence of 5' CACGGC 3'; or
  f) the first terminal stretch of nucleotides comprises a nucleotide sequence of 5' CCCGUG 3' and the second terminal stretch of nucleotides comprises a nucleotide sequence of 5' CACGGG 3'; or
  g) the first terminal stretch of nucleotides comprises a nucleotide sequence of 5' GCGUG 3' and the second terminal stretch of nucleotides comprises a nucleotide sequence of 5' CACGC 3'; or
  h) the first terminal stretch of nucleotides comprises a nucleotide sequence of 5' GGGUG 3' and the second terminal stretch of nucleotides comprises a nucleotide sequence of 5' CACCC 3'; or i) the first terminal stretch of nucleotides comprises a nucleotide sequence of 5' GCCUG 3' and the second terminal stretch of nucleotides comprises a nucleotide sequence of 5' CAGGC 3'; or j) the first terminal stretch of nucleotides comprises a nucleotide sequence of 5' CGUG 3' and the second terminal stretch of nucleotides comprises a nucleotide sequence of 5' CACG 3'; or k) the first terminal stretch of nucleotides comprises a nucleotide sequence of 5' CGUG 3' and the second terminal stretch of nucleotides comprises a nucleotide sequence of 5' UACG 3'; or l) the first terminal stretch of nucleotides comprises a nucleotide sequence of 5' GCAG 3' and the second terminal stretch of nucleotides comprises a nucleotide sequence of 5' CUGC 3'.

The CGRP binding nucleic acid molecules comprising a first and a second terminal stretch consisting of ribonucleotides and 2'-deoxynucleotides comprise the following combination of first and second terminal stretches:

the first terminal stretch of nucleotides comprises a nucleotide sequence of 5' CCZ$_4$UZ$_5$ 3' and the second terminal stretch of nucleotides comprises a nucleotide sequence of 5' Z$_6$Z$_7$Z$_8$Z$_9$Z$_{10}$ 3', or wherein C, G, A and U are ribonucleotides, and Z$_4$ is G or dG, Z$_5$ is G or dG, Z$_6$ is C or dC, Z$_7$ is A or dA, Z$_8$ is C or dC, Z$_9$ is G or dG, Z$_{10}$ is G or dG, dC, dG and dA are 2'-deoxyribonucleotides, wherein in a preferred embodiment a) the first terminal stretch of nucleotides comprises a nucleotide sequence of 5' CCGUG 3' and the second terminal stretch of nucleotides comprises a nucleotide sequence of 5' CACGG 3'; or b) the first terminal stretch of nucleotides comprises a nucleotide sequence of 5' CCdGUG 3' and the second terminal stretch of nucleotides comprises a nucleotide sequence of 5' CACGG 3'; or c) the first terminal stretch of nucleotides comprises a nucleotide sequence of 5' CCGUdG 3' and the second terminal stretch of nucleotides comprises a nucleotide sequence of 5' CACGG 3'; or d) the first terminal stretch of nucleotides comprises a nucleotide sequence of 5' CCGUG 3' and the second terminal stretch of nucleotides comprises a nucleotide sequence of 5' dCACGG 3'; or e) the first terminal stretch of nucleotides comprises a nucleotide sequence of 5' CCGUG 3' and the second terminal stretch of nucleotides comprises a nucleotide sequence of 5' CdACGG 3'; or f) the first terminal stretch of nucleotides comprises a nucleotide sequence of 5' CCGUG 3' and the second terminal stretch of nucleotides comprises a nucleotide sequence of 5' CAdCGG 3'; or g) the first terminal stretch of nucleotides comprises a nucleotide sequence of 5' CCGUG 3' and the second terminal stretch of nucleotides comprises a nucleotide sequence of 5' CACdGG 3'; or h) the first terminal stretch of nucleotides comprises a nucleotide sequence of 5' CCGUG 3' and the second terminal stretch of nucleotides comprises a nucleotide sequence of 5' CACGdG 3'.

The binding affinity of CGRP binding Spiegelmers 212-G1-001, 226-F2-001, 226-F2-001-D41, 226-F2-001-D44, 226-F2-001-D41/D44 and 226-F2-001-D41-dU28 to human alpha-CGRP, expressed as K$_D$, was determined by plasmon resonance measurement (Example 4, FIGS. 4, 5, 6 and 13):

212-G1-001: K$_D$ of 5.12 nM,
226-F2-001: K$_D$ of 2.62 nM,
226-F2-001-D41: K$_D$ of 0.55 nM,
226-F2-001-D44: K$_D$ of 0.52 nM,
226-F2-001-D41/D44: K$_D$ of 0.2 nM,
226-F2-001-D41-dU28: K$_D$ of 0.07 nM
226-F2-001-D41-dU28: K$_D$ of 0.21 nM.

CGRP binding molecules 212-G1-001 and 226-F2-001 share the identical central stretch of nucleotides (see FIG. 1A). As shown by the affinity measurement (see above) a first and second terminal stretch with five nucleotides (see 226-F2-001) instead of four nucleotides (see 212-G1-001) led to a significant improvement of binding affinity to human CCRP.

Moreover, as shown above and in FIGS. 4, 5, and 6, the replacement of one (see 226-F2-001-D41 and 226-F2-001-D44) or two ribonucleotide(s) (see 226-F2-001-D41/D44) by 2'-deoxyribonucleotie(s) in the CGRP binding molecule 226-F2-001 led to a significant improvement of binding affinity to human alpha-CCRP.

In general, Spiegelmers are modified with PEG moiety for their use in vivo. CGRP binding nucleic acid molecules 226-F2-001 and 226-F2-001-D41 were synthesized as Spiegelmers comprising an amino-group at its 5'-end. To said amino-modified Spiegelmers a 40 kDa PEG-moiety was coupled leading to CGRP binding Spiegelmers 226-F2-001-5'-40 kDa-PEG and 226-F2-001-D41-40 kDa-PEG (also referred to as NOX-L41). Synthesis and PEGylation of Spiegelmer is described in Example 2. The PEG-modification of CGRP binding nucleic acid molecules 226-F2-001 and 226-F2-001-D41 had no influence of the binding and function of the Spiegelmers (see below).

The CGRP binding molecules 212-G1-001, 226-F2-001, 226-F2-001-5'-40 kDa-PEG and 226-F2-001-D41-5'40 kDa-PEG (also referred to as NOX-L41) are able to antagonize the function of human CGRP to its receptor in vitro with the following IC$_{50}$ (Example 5, FIGS. 7A and 7B):

212-G1-001: IC$_{50}$ of 8.7 nM,
226-F2-001: IC$_{50}$ of 3.5 nM,
226-F2-001-5'40 kDaPEG: IC$_{50}$ of 3.8 nM,
226-F2-001-D41-5'40 kDa-PEG: IC$_{50}$ of 0.39 nM.

In agreement with affinity measurements (see above), a first and second terminal stretch with five nucleotides (see 226-F2-001) instead of four nucleotides (see 212-G1-001) led to a significant stronger inhibition of the function of human alpha-CCRP (FIG. 7A).

Moreover, as shown above and in FIG. 7B replacement of one ribonucleotide by 2'-deoxyribonucleotide (226-F2-001-5'-40 kDa-PEG and NOX-L41, also referred to as 226-F2-001-D41-5'40 kDa-PEG) led to a significantly stronger inhibition of the function of human alpha-CCRP (see FIG. 7B).

EXAMPLE 2

Synthesis and Derivatization of Aptamers and Spiegelmers

Small Scale Synthesis

Aptamers (D-RNA nucleic acids or D-DNA modified D-RNA nucleic acids) and Spiegelmers (L-RNA nucleic acids or L-DNA modified L-RNA nucleic acids) were produced by solid-phase synthesis with an ABI 394 synthesizer (Applied Biosystems, Foster City, Calif., USA) using 2'TBDMS RNA and DNA phosphoramidite chemistry with standard exocyclic amine protecting groups (Damha and Ogilvie, 1993). For the RNA part of the oligonucleotide rA(N-Bz)-, rC(N-Ac)-, rG(N-ibu)-, and rU-phosphoramidites in the D- and L-configuration were used, while for the DNA part dA(N-Bz)-, dC(N-

Ac)-, dG(N-ibu)-, dT and dU in the D- and L-configuration were applied. All phosphoramidites were purchased from ChemGenes, Wilmington, Mass. After synthesis and deprotection aptamers and Spiegelmers were purified by gel electrophoresis.

Large Scale Synthesis Plus Modification

Spiegelmers were produced by solid-phase synthesis with an ÄktaPilot100 synthesizer (GE Healthcare, Freiburg) using 2'TBDMS RNA and DNA phosphoramidite chemistry with standard exocyclic amine protecting groups (Damha and Ogilvie, 1993). L-rA(N-Bz)-, L-rC(N-Ac)-, L-rG(N-ibu)-, L-rU-, L-dA(N-Bz)-, L-dC(N-Ac)-, L-dG(N-ibu)-, and L-dT-phosphoramidites were purchased from ChemGenes, Wilmington, Mass. The 5'-amino-modifier was purchased from American International Chemicals Inc. (Framingham, Mass., USA). Synthesis of the unmodified or a 5'-amino-modified Spiegelmer was started on L-riboA, L-riboC, L-riboG, L-riboU, L-2'deoxyA, L-2'deoxyC, L-2'deoxyG, or L-2'deoxyT modified CPG pore size 1000 Å (Link Technology, Glasgow, UK. For coupling of the RNA and DNA phosphoramidites (15 min per cycle), 0.3 M benzylthiotetrazole (CMS-Chemicals, Abingdon, UK) in acetonitrile, and 2 equivalents of the respective 0.2 M phosphoramidite solution in acetonitrile was used. An oxidation-capping cycle was used. Further standard solvents and reagents for oligonucleotide synthesis were purchased from Biosolve (Valkenswaard, NL). The Spiegelmer was synthesized DMT-ON; after deprotection, it was purified via preparative RP-HPLC (Wincott et al., 1995) using Source15RPC medium (Amersham). The 5'DMT-group was removed with 80% acetic acid (30 min at RT). In case of 5'amino-modified Spiegelmers the 5'MMT-group was removed with 80% acetic acid (90 min at RT). Subsequently, aqueous 2 M NaOAc solution was added and the Spiegelmer was desalted by tangential-flow filtration using a 5 K regenerated cellulose membrane (Millipore, Bedford, Mass.).

PEGylation of Spiegelmers

In order to prolong the Spiegelmer's plasma residence time in vivo, a 40 kDa polyethylene glycol (PEG) moiety was covalently coupled at the 5'-end of the Spiegelmers.

For PEGylation (for technical details of the method for PEGylation see European patent application EP 1 306 382), the purified 5'-amino modified Spiegelmer was dissolved in a mixture of $H_2O$ (2.5 ml), DMF (5 ml), and buffer A (5 ml; prepared by mixing citric acid. $H_2O$ [7 g], boric acid [3.54 g], phosphoric acid [2.26 ml], and 1 M NaOH [343 ml] and adding water to a final volume of 1 l; pH=8.4 was adjusted with 1 M HCl).

The pH of the Spiegelmer solution was brought to 8.4 with 1 M NaOH. Then, 40 kDa PEG-NHS ester (Jenkem Technology, Allen, Tex., USA) was added at 37° C. every 30 min in six portions of 0.25 equivalents until a maximal yield of 75 to 85% was reached. The pH of the reaction mixture was kept at 8-8.5 with 1 M NaOH during addition of the PEG-NHS ester.

The reaction mixture was blended with 4 ml urea solution (8 M), and 4 ml buffer B (0.1 M triethylammonium acetate in $H_2O$) and heated to 95° C. for 15 min. The PEGylated Spiegelmer was then purified by RP-HPLC with Source 15RPC medium (Amersham), using an acetonitrile gradient (buffer B; buffer C: 0.1 M triethylammonium acetate in acetonitrile). Excess PEG eluted at 5% buffer C, PEGylated Spiegelmer at 10-15% buffer C. Product fractions with a purity of >95% (as assessed by HPLC) were combined and mixed with 40 ml 3 M NaOAC. The PEGylated Spiegelmer was desalted by tangential-flow filtration (5 K regenerated cellulose membrane, Millipore, Bedford Mass.).

EXAMPLE 3

Ranking of D-Alpha-CGRP Binding Aptamers by a Competitive Pull-Down Binding Assay A pull-down binding assay was used for comparative ranking of a set of different test aptamers. For this purpose non-labeled aptamers competed with a labeled reference aptamer for binding to biotinylated D-CGRP, thus decreasing the binding signal according to the affinity of the test aptamers to D-CGRP. The reference aptamer was radioactively labeled at the 5'-end by T4 polynucleotide kinase (Invitrogen, Karlsruhe, Germany) using [$\gamma$-$^{32}$P]-labeled ATP (Hartmann Analytic, Braunschweig, Germany) to a specific radioactivity of 400000-800000 cpm/pmol. The binding reactions were performed at 37° C. with 150 pM radioactively labeled reference aptamer together with a constant amount of 10-20 nM biotinylated D-CGRP in 360 μl selection buffer (20 mM Tris-HCl pH 7.4; 150 mM NaCl; 5 mM KCl; 1 mM $MgCl_2$; 1 mM $CaCl_2$; 0.1% [w/vol] Tween-20; 10 μg/ml HSA; 10 μg/ml Yeast RNA) for 2-4 hours. These conditions resulted in about 5-10% binding of the reference aptamer to biotinylated D-CGRP after immobilization and washing on NeutrAvidin agarose or Streptavidin Ultralink Plus (both from Pierce Biotechnology, Rockford, USA). For competition non-labeled test aptamers were added at 5 nM, 50 nM, and 500 nM together with the constant amount of the labeled reference aptamer to the binding reactions. After completion of binding, immobilization, appropriate washing and determination of immobilized radioactivity with a scintillation counter the aptamer that was found most active in the test served then as a new reference for comparative analysis of further aptamer variants. The results are shown in FIGS. 1A-B.

EXAMPLE 4

Biacore Measurement of Spiegelmers Binding to CGRP and Related Peptides

Biacore Assay Setup

Human CGRP and related peptides were immobilized by amine coupling procedure on a carboxymethylated (abbr. CM) dextran-coated sensor chip using a 1:1 mixture of 0.4 M EDC (1-ethyl-3-(3-dimethylaminopropyl) carbodiimide in $H_2O$; GE, BR-1000-50) and 0.1M NHS (N-hydroxysuccinimide in $H_2O$; GE, BR-1000-50). The reference flow cell on the same sensor chip was blocked with biotin.

General Kinetic Evaluation

The CGRP binding Spiegelmers were dissolved in water to a stock concentration of 100 μM (quantification by measurement of absorption at 260 nm), heated up to 95° C. for 30 seconds in a water bath or thermo mixer and snap cooled on ice to assure a homogenous dissolved solution.

Kinetic parameters and dissociation constants were evaluated by a series of Spiegelmer injections at concentrations of 1000, 500, 250, 125, 62.5, 31.25, 15.63, 7.8, 3.9, 1.95 and 0 nM or at concentrations of 500-250-125-62.5-31.3-15.6-7.8 (2×)-3.9-1.95-0.98-0.48-0 nM diluted in running buffer. In all experiments, the analysis was performed at 37° C. using the Kinject command defining an association time of 240 to 360 and a dissociation time of 240 to 360 seconds at a flow of 30 μl/min. The assay was double referenced, whereas FC1 served as (blocked) surface control (bulk contribution of each Spiegelmer concentration) and a series of buffer injections without analyte determined the bulk contribution of the buffer itself. Data analysis and calculation of dissociation constant $K_D$ was done with the BIAevaluation 3.1.1 software (BIA- CORE AB, Uppsala, Sweden) using a modified Langmuir 1:1 stoichiometric fitting algorithm.

Data analysis and calculation of dissociation constant $K_D$ was done with the BIAevaluation 3.1.1 software (BIACORE AB, Uppsala, Sweden) using a modified Langmuir 1:1 stoichiometric fitting algorithm, with a constant RI and mass transfer evaluation with a mass transport coefficient kt of 1×107 [RU/M*s]. The results are shown in FIGS. 3 A-D, 4-6, 9 and 13).

EXAMPLE 5

Inhibition of Alpha-CGRP-Induced cAMP Production in Human Neuroblastoma Cells Biological efficacy of CGRP-binding Spiegelmers was analysed as follows.

SK-N-MC human neuroblastoma cells (ACC203, DSMZ, Braunschweig) were seeded at 5×10e4 cells/well in a flat-bottomed 96-well plate (Greiner) and cultivated for 48 h at 37° C. and 5% $CO_2$ in 100 µl in DMEM (1000 mg/L glucose, Invitrogen) supplemented with 10% heat-inactivated fetal calf serum (FCS), 4 mM L-alanyl-L-glutamine (GLUTAMAX), 50 units/ml Penicillin and 50 µg/ml Streptomycin.

Stimulation solutions (1 nM human or rat L-alphaCGRP (Bachem)+increasing concentrations of Spiegelmer) were prepared as triplicates in HBSS (Gibco) supplemented with 1 mg/ml BSA and 20 mM HEPES using v-bottomed 0.2 ml low profile 96-well plates and incubated at 37° C. for 60 min in total. Blank values (no L-alphaCGRP, no Spiegelmer) and control values (1 nM L-alphaCGRP, no Spiegelmer) were included as triplicates. 20 min prior to stimulation 1 mM phosphodiesterase inhibitor 3-Isobutyl-1-methylxanthine (IBMX, Sigma; 50 mM stock in DMSO diluted in HBSS/BSA/HEPES) was added to the cells and the stimulation solutions.

For stimulation, cell culture medium was removed from the cells and substituted by 100 µl pre-incubated stimulation solution. Cells were stimulated for 30 min at 37° C., 5% $CO_2$. After removal of stimulation solutions cells were lysed by addition of 50 µl/well assay/lysis buffer (Applied Biosystems, Tropix cAMP-Screen™ System kit) for 30 min at 37° C.

The amount of cAMP produced per well was subsequently measured using the Tropix cAMP-Screen™ ELISA System kit (Applied Biosystems) according to manufacturer's instructions. Briefly, a standard curve is prepared in assay/lysis buffer ranging from 6 nmol to 0.6 pmol cAMP/well. Cell lysates diluted in assay/lysis buffer and standard curves are added to microplates precoated with goat anti-rabbit IgG. cAMP alkaline phosphatase conjugate and anti-cAMP antibody are added to the samples and incubated for 60 min at room temperature. Subsequently, plates are washed and chemiluminescent substrate is added. After 30 min chemiluminescence is measured in a FLUOstar OPTIMA plate reader unit (BMG Labtech). The cAMP-Screen™ ELISA system is a competitive immunoassay format. Thus, light signal intensity is inversely proportional to the cAMP level in the sample or standard preparation. This assay system was used to test Spiegelmers within the scope of Examples 1 and 7 described herein. The result is illustrated in FIGS. 7 and 8. The quantities of cAMP produced is given as percentage of the control. The concentration of Spiegelmer required for 50% inhibition of cAMP production relative to control defines the inhibitory constant $IC_{50}$. The results are shown in FIGS. 7A and 7B.

EXAMPLE 6

Inhibition of Amylin-Induced cAMP Production

Cross-reactivity of CGRP-binding Spiegelmers to human or rat amylin was analysed as follows.

MCF-7 human breast cancer cells (ACC115, DSMZ, Braunschweig) were seeded at 5×10e4 cells/well in a flat-bottomed 96-well plate (Greiner) and cultivated for 24 h at 37° C. and 5% $CO_2$ in 1000 in DMEM (1000 mg/L glucose, Invitrogen) supplemented with 10% heat-inactivated fetal calf serum (FCS), 4 mM L-alanyl-L-glutamine (GLUTAMAX), 50 units/ml Penicillin and 50 µg/ml Streptomycin.

Stimulation solutions (3 nM human or rat L-amylin (Bachem) plus increasing concentrations of Spiegelmer) were prepared as triplicates in HBSS (Gibco) supplemented with 1 mg/ml BSA and 20 mM HEPES using v-bottomed 0.2 ml low profile 96-well plates and incubated at 37° C. for 60 min in total. Blank values (no L-amylin, no Spiegelmer) and control values (1 nM L-amylin, no Spiegelmer) were included as triplicates. 20 min prior to stimulation 1 mM phosphodiesterase inhibitor 3-Isobutyl-1-methylxanthine (IBMX, Sigma; 50 mM stock in DMSO diluted in HBSS/BSA/HEPES) was added to the cells and the stimulation solutions.

For stimulation, cell culture medium was removed from the cells and substituted by 100 µl pre-incubated stimulation solution. Cell were stimulated for 30 min at 37° C., 5% $CO_2$. After removal of stimulation solutions cells were lysed by addition of 50 µl/well lysis buffer (Applied Biosystems, Tropix cAMP-Screen™ System kit) for 30 min at 37° C.

The amount of cAMP produced per well was subsequently measured using the Tropix cAMP-Screen™ ELISA System kit (Applied Biosystems) according to manufacturer's instructions, as briefly described above.

This assay system was used to test Spiegelmers within the scope of Example 7 described herein. The result is illustrated in FIG. 10. Quantities of cAMP produced are given as percentage of the control. The concentration of Spiegelmer required for 50% inhibition of cAMP production relative to control defines the inhibitory constant $IC_{50}$.

EXAMPLE 7

Discrimination of CGRP Binding Spiegelmer NOX-L41 Between CGRP and Amylin

FIG. 9 shows the alignment of the four C-terminally amidated peptides human alpha-CGRP, rat alpha-CGRP, human amylin and rat amylin. All four peptides have a conserved Cys2-Cys7 disulfide bridge.

Spiegelmer NOX-L41 (also referred to as 226-F2-001-D41-5'40 kDa-PEG) and its unpegylated form 226-F2-001-D41 discriminate between these closely related peptides and selectively bind to human and rat alpha-CGRP. NOX-L41 inhibits human alpha-CGRP induced cAMP production with $IC_{50}$ of 0.39 nM (FIG. 9). In contrast, cellular activation by human amylin was not inhibited by NOX-L41 at concentrations up to 1 µM (FIG. 10). An amylin-binding Spiegelmer (sequence: 5'-40 kDa-PEG-GGACUGAUGGCGCG-GUCCU AUUACGCCGAUAGGGUGAGGGGA, [SEQ ID NO: 135]) inhibits human amylin induced cAMP production (FIG. 10). In agreement, no binding of 226-F2-001-D41 to human amylin was detected by kinetic Biacore measurement (FIG. 9). The affinity ($K_D$) of 226-F2-001-D41 to human CGRP was 0.55 nM (FIG. 9). Thus, NOX-L41 discriminates between human alpha-CGRP and human amylin with a factor of more than one thousand. The discrimination between rat alpha-CGRP and human amylin is less pronounced with $IC_{50}$ of 3.6 nM and 283 nM, respectively, which corresponds to a discrimination factor of more than 75 (FIG. 9).

From the relation of the inhibitory concentrations and the affinities one can roughly deduce which amino acid residues may be involved in Spiegelmer binding.

Rat amylin is inhibited by NOX-L41 with a measurable $IC_{50}$ whilst the inhibition of human amylin was not detectable (FIGS. 9 and 10). There are only amino acid residues that are different in rat and human amylin, namely amino acid residues 18 and 29 The respective change from to human amylin is R18H and P29S. Thus either R18 or P29 or both are part of the minimal binding epitope. In case of P29 it is also possible that the proline-induced bent in the peptides' backbones is needed for proper recognition of neighboring conserved residues. From literature it is known that nucleic acid aptamers preferably target arginines. Furthermore, epitopes of the target molecules bound by aptamers usually comprise more than one amino acid with multiple weak contacts contributing to the overall affinity. Therefore it is also in this case R18 plays a central role in Spiegelmer-binding with adjacent residues contributing to the binding event which explains the weaker binding to rat amylin compared to the CGRPs.

References

The complete bibliographic data of the documents recited herein the disclosure of which is incorporated by reference is, if not indicated to the contrary, as follows.

Adwanikar, H., G. Ji, et al. (2007). "Spinal CGRP 1 receptors contribute to supraspinally organized pain behavior and pain-related sensitization of amygdala neurons." Pain 132 (1-2): 53-66.

Alessandri, M., L. Massanti, et al. (2006). "Plasma changes of calcitonin gene-related peptide and substance P in patients with dialysis headache." Cephalalgia 26(11): 1287-93.

Altschul, S. F., Gish, W., et al. (1990). "Basic local alignment search tool." J Mol Biol 215(3):403-10.

Altschul, S. F., Madden, T. L., et al. (1997). "Gapped BLAST and PSI-BLAST: a new generation of protein database search programs." Nucleic Acids Res 25(17):3389-402.

Amara, S. G., V. Jonas, et al. (1982). "Alternative RNA processing in calcitonin gene expression generates mRNAs encoding different polypeptide products." Nature 298(5871): 240-4.

Ambalavanar, R., M. Moritani, et al. (2006). "Deep tissue inflammation upregulates neuropeptides and evokes nociceptive behaviors which are modulated by a neuropeptide antagonist." Pain 120(1-2): 53-68.

Antunez, C., M. J. Torres, et al. (2009). "Calcitonin gene-related peptide modulates interleukin-13 in circulating cutaneous lymphocyte-associated antigen-positive T cells in patients with atopic dermatitis." Br J Dermatol 161(3): 547-53.

Bennett, A. D., K. M. Chastain, et al. (2000). "Alleviation of mechanical and thermal allodynia by CGRP(8-37) in a rodent model of chronic central pain." Pain 86(1-2): 163-75.

Bourdu, S., M. Dapoigny, et al. (2005). "Rectal instillation of butyrate provides a novel clinically relevant model of non-inflammatory colonic hypersensitivity in rats." Gastroenterology 128(7): 1996-2008.

Breeze, A. L., T. S. Harvey, et al. (1991). "Solution structure of human calcitonin gene-related peptide by 1H NMR and distance geometry with restrained molecular dynamics." Biochemistry 30(2): 575-82.

Chen, Y., H. H. Willcockson, et al. (2008). "Increased expression of CGRP in sensory afferents of arthritic mice—effect of genetic deletion of the vanilloid receptor TRPV1." Neuropeptides 42(5-6): 551-6.

Connor, K. M., R. E. Shapiro, et al. (2009). "Randomized, controlled trial of telcagepant for the acute treatment of migraine." Neurology 73(12): 970-7.

Damha, M. J., Ogilvie, K. K., et al. (1993). "Oligoribonucleotide synthesis. The silyl-phosphoramidite method." Methods Mol Biol 20:81-114.

Denekas, T., M. Troltzsch, et al. (2006) "Inhibition of stimulated meningeal blood flow by a calcitonin gene-related peptide binding mirror-image RNA oligonucleotide." Br J Pharmacol 148(4): 536-43.

Diener, H. C., P. Barbanti, et al. (2011). "BI 44370 TA, an oral CGRP antagonist for the treatment of acute migraine attacks: results from a phase II study." Cephalalgia 31(5): 573-84.

Dirmeier, M., S. Capellino, et al. (2008). "Lower density of synovial nerve fibres positive for calcitonin gene-related peptide relative to substance P in rheumatoid arthritis but not in osteoarthritis." Rheumatology (Oxford) 47(1): 36-40.

Edvinsson, L. and T. W. Ho (2010). "CGRP receptor antagonism and migraine." Neurotherapeutics 7(2): 164-75.

Edvinsson, L., E. Nilsson, et al. (2007) "Inhibitory effect of BIBN4096BS, CGRP(8-37), a CGRP antibody and an RNA-Spiegelmer on CGRP induced vasodilatation in the perfused and non-perfused rat middle cerebral artery." Br J Pharmacol 150(5): 633-40.

Ferreira-Gomes, J., S. Adaes, et al. (2010). "Phenotypic alterations of neurons that innervate osteoarthritic joints in rats." Arthritis Rheum 62(12): 3677-85.

Field, B. C., O. B. Chaudhri, et al. (2010). "Bowels control brain: gut hormones and obesity." Nat Rev Endocrinol 6(8): 444-53.

Frese, A., M. Schilgen, et al. (2005). "Calcitonin gene-related peptide in cervicogenic headache." Cephalalgia 25(9): 700-3.

Gabra, B. H. and P. Sirois (2004). "Pathways for the bradykinin B1 receptor-mediated. diabetic hyperalgesia in mice." Inflamm Res 53(12): 653-7.

Gallai, V., P. Sarchielli, et al. (1995). "Vasoactive peptide levels in the plasma of young migraine patients with and without aura assessed both interictally and ictally." Cephalalgia 15(5): 384-90.

Goadsby, P. J. (2003). "Migraine: diagnosis and management." Intern Med J 33(9-10): 436-42.

Goadsby, P. J. and L. Edvinsson (1994). "Human in vivo evidence for trigeminovascular activation in cluster headache. Neuropeptide changes and effects of acute attacks therapies." Brain 117 (Pt 3): 427-34.

Goadsby, P. J., L. Edvinsson, et al. (1990). "Vasoactive peptide release in the extracerebral circulation of humans during migraine headache." Ann Neurol 28(2): 183-7.

Gram, D. X., A. J. Hansen, et al. (2005). "Plasma calcitonin gene-related peptide is increased prior to obesity, and sensory nerve desensitization by capsaicin improves oral glucose tolerance in obese Zucker rats." Eur J Endocrinol 153(6): 963-9.

Han, N., D. Y. Zhang, et al. (2010). "Calcitonin gene-related peptide induces proliferation and monocyte chemoattractant protein-1 expression via extracellular signal-regulated kinase activation in rat osteoblasts." Chin Med J (Engl) 123(13): 1748-53.

Hay, D. L., C. S. Walker, et al. (2011). "Adrenomedullin and calcitonin gene-related peptide receptors in endocrine-related cancers: opportunities and challenges." Endocr Relat Cancer 18(1): C1-14.

Ho, T. W., L. Edvinsson, et al. (2010). "CGRP and its receptors provide new insights into migraine pathophysiology." Nat Rev Neurol 6(10): 573-82.

Ho, T. W., M. D. Ferrari, et al. (2008). "Efficacy and tolerability of MK-0974 (telcagepant), a new oral antagonist of calcitonin gene-related peptide receptor, compared with zolmitriptan for acute migraine: a randomised, placebo-controlled, parallel-treatment trial." Lancet 372(9656): 2115-23.

Hou, Q., T. Barr, et al. (2011). "Keratinocyte expression of calcitonin gene-related peptide beta: implications for neuropathic and inflammatory pain mechanisms." Pain 152 (9): 2036-51.

Huang, J., L. L. Stohl, et al. (2011). "Calcitonin Gene-related Peptide Inhibits Chemokine Production by Human Dermal Microvascular Endothelial Cells." Brain Behav Immun.

Juhasz, G., T. Zsombok, et al. (2003). "NO-induced migraine attack: strong increase in plasma calcitonin gene-related peptide (CGRP) concentration and negative correlation with platelet serotonin release." Pain 106(3): 461-70.

Juhl, L., L. Edvinsson, et al. (2007). "Effect of two novel CGRP-binding compounds in a closed cranial window rat model." Eur J Pharmacol 567(1-2): 117-24.

Klussmann S. (2006). "The Aptamer Handbook—Functional Oligonucleotides and their Applications." Edited by S. Klussmann. WILEY-VCH, Weinheim, Germany, ISBN 3-527-31059-2

Kopp, S. (2001). "Neuroendocrine, immune, and local responses related to temporomandibular disorders." J Orofac Pain 15(1): 9-28.

Kusser, W. (2000). "Chemically modified nucleic acid aptamers for in vitro selections: evolving evolution." J Biotechnol 74(1): 27-38.

Lassen, L. H., P. A. Haderslev, et al. (2002). "CGRP may play a causative role in migraine." Cephalalgia 22(1): 54-61.

Lee, M., B. J. Kim, et al. (2009). "Complete Freund's adjuvant-induced intervertebral discitis as an animal model for discogenic low back pain." Anesth Analg 109(4): 1287-96.

Lee, S. E. and J. H. Kim (2007). "Involvement of substance P and calcitonin gene-related peptide in development and maintenance of neuropathic pain from spinal nerve injury model of rat." Neurosci Res 58(3): 245-9.

Limmroth, V., Z. Katsarava, et al. (2001). "An in vivo rat model to study calcitonin gene related peptide release following activation of the trigeminal vascular system." Pain 92(1-2): 101-6.

Liu, L. S., M. Shenoy, et al. (2011). "Substance P and Calcitonin Gene Related Peptide Mediate Pain in Chronic Pancreatitis and Their Expression is Driven by Nerve Growth Factor." JOP 12(4): 389-94.

Lutz, T. A. (2006). "Amylinergic control of food intake." Physiol Behav 89(4): 465-71.

Lutz, T. A., E. Del Prete, et al. (1994). "Reduction of food intake in rats by intraperitoneal injection of low doses of amylin." Physiol Behav 55(5): 891-5.

Ma, W. and R. Quirion (2006). "Increased calcitonin gene-related peptide in neuroma and invading macrophages is involved in the up-regulation of interleukin-6 and thermal hyperalgesia in a rat model of mononeuropathy." J Neurochem 98(1): 180-92.

Maintz, L., E. Wardelmann, et al. (2011). "Neuropeptide blood levels correlate with mast cell load in patients with mastocytosis." Allergy.

Mairal T., Ozalp V. C., Lozano Sanchez P., et al. (2008). "Aptamers: molecular tools for analytical applications." Anal Bioanal Chem 390(4):989-1007

McDougall, J. J. (2006). "Arthritis and pain. Neurogenic origin of joint pain." Arthritis Res Ther 8(6): 220.

McGinnis, S., Madden, T. L. et al. (2004). "BLAST: at the core of a powerful and diverse set of sequence analysis tools." Nucleic Acids Res 32(Web Server issue):W20-5.

McLatchie, L. M., N. J. Fraser, et al. (1998). "RAMPs regulate the transport and ligand specificity of the calcitonin-receptor-like receptor." Nature 393(6683): 333-9.

Mikami, N., K. Watanabe, et al. (2012). "Calcitonin gene-related peptide enhances experimental autoimmune encephalomyelitis by promoting Th17-cell functions." Int Immunol 24(11): 681-91.

Minamiyama, M., M. Katsuno, et al. (2012). "Naratriptan mitigates CGRP1-associated motor neuron degeneration caused by an expanded polyglutamine repeat tract." Nat Med 18(10): 1531-8.

Mishima, T., Y. Ito, et al. (2011). "Calcitonin gene-related peptide facilitates revascularization during hindlimb ischemia in mice." Am J Physiol Heart Circ Physiol 300(2): H431-9.

Mogil, J. S., F. Miermeister, et al. (2005). "Variable sensitivity to noxious heat is mediated by differential expression of the CGRP gene." Proc Natl Acad Sci USA 102(36): 12938-43.

Monteith, T. S. and P. J. Goadsby (2011). "Acute migraine therapy: new drugs and new approaches." Curr Treat Options Neurol 13(1): 1-14.

Morley, J. E., J. F. Flood, et al. (1994). "Modulation of food intake by peripherally administered amylin." Am J Physiol 267(1 Pt 2): R178-84.

Needleman and Wunsch (1970). "A general method applicable to the search for similarities in the amino acid sequence of two proteins." J Mol Biol 48(3):443-53.

Nitzan-Luques, A., M. Devor, et al. (2011). "Genotype-selective phenotypic switch in primary afferent neurons contributes to neuropathic pain." Pain 152(10): 2413-26.

Nohr, D., M. K. Schafer, et al. (1999). "Calcitonin gene-related peptide gene expression in collagen-induced arthritis is differentially regulated in primary afferents and motoneurons: influence of glucocorticoids." Neuroscience 93(2): 759-73.

Olesen, J., H. C. Diener, et al. (2004). "Calcitonin gene-related peptide receptor antagonist BIBN 4096 BS for the acute treatment of migraine." N Engl J Med 350(11): 1104-10.

Ostrowski, S. M., A. Belkadi, et al. (2011). "Cutaneous Denervation of Psoriasiform Mouse Skin Improves Acanthosis and Inflammation in a Sensory Neuropeptide-Dependent Manner." J Invest Dermatol.

Ottosson, A. and L. Edvinsson (1997). "Release of histamine from dural mast cells by substance P and calcitonin gene-related peptide." Cephalalgia 17(3): 166-74.

Pearson and Lipman (1988). "Improved tools for biological sequence comparison." Proc. Nat'l. Acad. Sci. USA 85: 2444

Powell, K. J., W. Ma, et al. (2000). "Blockade and reversal of spinal morphine tolerance by peptide and non-peptide calcitonin gene-related peptide receptor antagonists." Br J Pharmacol 131(5): 875-84.

Puttfarcken, P. S., P. Han, et al. (2010). "A-995662 [(R)-8-(4-methyl-5-(4-(trifluoromethyl)phenyl)oxazol-2-ylamino)-

1,2,3,4-tetrahydronaphthalen-2-ol], a novel, selective TRPV1 receptor antagonist, reduces spinal release of glutamate and CGRP in a rat knee joint pain model." Pain 150(2): 319-26.

Raddant, A. C. and A. F. Russo (2011). "Calcitonin gene-related peptide in migraine: intersection of peripheral inflammation and central modulation." Expert Rev Mol Med 13: e36.

Saxler, G., F. Loer, et al. (2007). "Localization of SP- and CGRP-immunopositive nerve fibers in the hip joint of patients with painful osteoarthritis and of patients with painless failed total hip arthroplasties." Eur J Pain 11(1): 67-74.

Schweizerhof, M., S. Stosser, et al. (2009). "Hematopoietic colony-stimulating factors mediate tumor-nerve interactions and bone cancer pain." Nat Med 15(7): 802-7.

Sink, K. S., D. L. Walker, et al. (2011). "Calcitonin gene-related Peptide in the bed nucleus of the stria terminalis produces an anxiety-like pattern of behavior and increases neural activation in anxiety-related structures." J Neurosci 31(5): 1802-10.

Smith and Waterman (1981), Adv. Appl. Math. 2: 482

Stepien, A., P. Jagustyn, et al. (2003). "[Suppressing effect of the serotonin 5HT1B/D receptor agonist rizatriptan on calcitonin gene-related peptide (CGRP) concentration in migraine attacks]." Neurol Neurochir Pol 37(5): 1013-23.

Summ, O., A. P. Andreou, et al. (2010). "A potential nitrergic mechanism of action for indomethacin, but not of other COX inhibitors: relevance to indomethacin-sensitive headaches." J Headache Pain 11(6): 477-83.

Szadek, K. M., P. V. Hoogland, et al. (2010). "Possible nociceptive structures in the sacroiliac joint cartilage: An immunohistochemical study." Clin Anat 23(2): 192-8.

Tan, K. K., M. J. Brown, et al. (1995). "Calcitonin gene-related peptide as an endogenous vasodilator: immunoblockade studies in vivo with an anti-calcitonin gene-related peptide monoclonal antibody and its Fab' fragment." Clin Sci (Lond) 89(6): 565-73.

Tanaka, H., A. Shimaya, et al. (2011). "Enhanced insulin secretion and sensitization in diabetic mice on chronic treatment with a transient receptor potential vanilloid 1 antagonist." Life Sci.

Tfelt-Hansen, P. and H. Le (2009). "Calcitonin gene-related peptide in blood: is it increased in the external jugular vein during migraine and cluster headache? A review." J Headache Pain 10(3): 137-43.

Tfelt-Hansen, P. and M. Ashina (2010). "Extracranial source of increased CGRP in migraine children?" Cephalalgia 30(3): 380-1.

Toda, M., T. Suzuki, et al. (2008). "Neuronal system-dependent facilitation of tumor angiogenesis and tumor growth by calcitonin gene-related peptide." Proc Natl Acad Sci USA 105(36): 13550-5.

Tvedskov, J. F., K. Lipka, et al. (2005). "No increase of calcitonin gene-related peptide in jugular blood during migraine." Ann Neurol 58(4): 561-8.

van Rossum, D., U. K. Hanisch, et al. (1997). "Neuroanatomical localization, pharmacological characterization and functions of CGRP, related peptides and their receptors." Neurosci Biobehav Rev 21(5): 649-78.

Vater, A., F. Jarosch, et al. (2003). "Short bioactive Spiegelmers to migraine-associated calcitonin gene-related peptide rapidly identified by a novel approach: tailored-SELEX." Nucleic Acids Res 31(21): e130.

Venkatesan, N., S. J. Kim, et al. (2003). "Novel phosphoramidite building blocks in synthesis and applications toward modified oligonucleotides." Curr Med Chem 10(19): 1973-91.

Wacnik, P. W., C. M. Baker, et al. (2005). "Tumor-induced mechanical hyperalgesia involves CGRP receptors and altered innervation and vascularization of DsRed2 fluorescent hindpaw tumors." Pain 115(1-2): 95-106.

Wang, L., X. Shi, et al. (2010). "Calcitonin-gene-related peptide stimulates stromal cell osteogenic differentiation and inhibits RANKL induced NF-kappaB activation, osteoclastogenesis and bone resorption." Bone 46(5): 1369-79.

Wang, Z., W. Ma, et al. (2009). "Cell-type specific activation of p38 and ERK mediates calcitonin gene-related peptide involvement in tolerance to morphine-induced analgesia." FASEB J 23(8): 2576-86.

Wick, E. C., S. G. Hoge, et al. (2006). "Transient receptor potential vanilloid 1, calcitonin gene-related peptide, and substance P mediate nociception in acute pancreatitis." Am J Physiol Gastrointest Liver Physiol 290(5): G959-69.

Wincott, F., DiRenzo, A, et al. (1995). "Synthesis, deprotection, analysis and purification of RNA and ribozymes." Nucleic Acids Res 23(14):2677-84.

Winston, J. H., Z. J. He, et al. (2005). "Molecular and behavioral changes in nociception in a novel rat model of chronic pancreatitis for the study of pain." Pain 117(1-2): 214-22.

Xie, W., J. T. Fisher, et al. (2011). "CGRP induction in cystic fibrosis airways alters the submucosal gland progenitor cell niche in mice." J Clin Invest 121(8): 3144-58.

Xu, X., Z. Li, et al. (2012). "High Expression of Calcitonin Gene-Related Peptide and Substance P in Esophageal Mucosa of Patients with Non-Erosive Reflux Disease." Dig Dis Sci.

Zeller, J., K. T. Poulsen, et al. (2008). "CGRP functionblocking antibodies inhibit neurogenic vasodilatation without affecting heart rate or arterial blood pressure in the rat." Br J Pharmacol 155(7): 1093-103.

Zhang, C. and J. J. McDougall (2006). "Stimulation of sensory neuropeptide release by nociceptin/orphanin FQ leads to hyperaemia in acutely inflamed rat knees." Br J Pharmacol 148(7): 938-46.

Zhang, Z., F. Gong, et al. (2012). "Plasma level of calcitonin gene-related peptide in patients with polycystic ovary syndrome and its relationship to hormonal and metabolic parameters." Peptides.

Zheng, L. F., R. Wang, et al. (2008). "Calcitonin gene-related peptide dynamics in rat dorsal root ganglia and spinal cord following different sciatic nerve injuries." Brain Res 1187: 20-32.

Zheng, S., W. Li, et al. (2010). "Calcitonin gene-related peptide promotes angiogenesis via AMP-activated protein kinase." Am J Physiol Cell Physiol 299(6): C1485-92.

The features of the present invention disclosed in the specification, the claims and/or the drawings may both separately and in any combination thereof be material for realizing the invention in various forms thereof.

The invention claimed is:

1. An L-nucleic acid that binds CGRP, or a homolog of said L-nucleic acid, wherein said L-nucleic acid comprises SEQ ID NO:45, and the homolog has at least 85% homology to SEQ ID NO:45.

2. The L-nuc eic acid according to claim 1, wherein the L-nucleic acid is an antagonist of an activity mediated by CGRP.

3. The L-nucleic acid according to claim 1, wherein the CGRP is human CGRP, mouse CGRP, rat CGRP or CGRP from Maca mulatta.

4. The L-nucleic acid according to claim 1, wherein the CGRP is human CGRP.

5. The L-nucleic acid according to claim 1, wherein the CGRP is α-CGRP or β-CGRP.

6. The L-nucleic acid according to claim 1, wherein the CGRP is a human α-CGRP or a rat α-CGRP.

7. The L-nucleic acid according tea claim 1, wherein the L-nucleic acid has binding affinity to human α-CGRP, expressed as $K_D$, of 10 nM or below.

8. The L-nucleic acid according to claim 1, wherein the L-nucleic acid has binding affinity to human α-CGRP, expressed as $K_D$, of 1 nM or below.

9. The L-nucleic acid according to claim 1, wherein the L-nucleic acid has binding affinity to human α-CGRP, expressed as IC50, of 10 nM or below.

10. The L-nucleic acid according to claim 1, wherein the L-nucleic acid has binding affinity to human α-CGRP, expressed as IC50, of 1 nM or below.

11. The L-nucleic acid according to claim 1, wherein the L-nucleic acid has binding affinity to human amylin, expressed as $K_D$, of 100 nM or more.

12. The L-nucleic acid according to claim 1, wherein the L-nucleic acid has binding affinity to human amylin, expressed as IC50, of 100 nM or more.

13. The L-nucleic acid according to claim 1, wherein
the L-nucleic acid has binding affinity to human α-CGRP, expressed as $K_D$, of 10 nM or below, and to human amylin of 100 nM or more, or
the L-nucleic acid has binding affinity to human α-CGRP, expressed as IC50, of 10 nM or below, and to human amylin of 100 nM or more.

14. The L-nucleic acid according to claim 1, wherein
the L-nucleic acid has binding affinity to human α-CGRP, expressed as $K_D$, of 1 nM or below, and to human amylin of 100 nM or more, or
the L-nucleic acid has binding affinity to human α-CGRP, expressed as IC50, 1 nk or below, and to human amylin of 100 nM or more.

15. The L-nucleic acid according to claim 1, wherein the L-nucleic acid comprises a modification group.

16. The L-nucleic acid according to claim 15, wherein the modification group is selected from the group consisting of polyethylene glycol, linear polyethylene glycol, branched polyethylene glycol, hydroxyethyl starch, a peptide, a protein, a polysaccharide, polyoxypropylene, polyoxyamidate, poly (2-hydroxyethyl)-L-glutamine and a sterol.

17. The L-nucleic acid according to claim 16, wherein the linear or branched polyethylene glycol comprises a molecular weight of from about 20,000 to about 120,000 Da.

18. The L-nucleic acid according to claim 15, wherein the hydroxyethyl starch comprises a molecular weight of from about 100 to about 700 kDa.

19. The L-nucleic acid according to claim 15, wherein the modification group is coupled to the L-nucleic acid by a linker.

20. The L-nucleic acid according to claim 15, wherein the modification group is at a terminus of the L-nucleic acid.

21. The L-nucleic acid according to claim 15, wherein the modification group is at the 5' terminus of the L-nucleic acid.

22. A pharmaceutical composition comprising the L-nucleic acid according to claim 1 and a pharmaceutically acceptable excipient, a pharmaceutically acceptable carrier, a pharmaceutically active agent or a combination thereof.

23. A complex comprising the L-nucleic acid according to claim 1 and CGRP.

24. A method for the detection of the L-nucleic acid according to claim 1 in a sample, wherein the method comprises the steps of:
a) providing a capture probe, wherein the capture probe is at least partially complementary to a first part of the L-nucleic acid according to claim 1, and a detection probe, wherein the detection probe is at least partially complementary to a second part of the L-nucleic acid according to claim 1, or, alternatively, the capture probe is at least partially complementary to a second part of the L-nucleic acid according to claim 1 and the detection probe is at least partially complementary to the first part of the L-nucleic acid according to claim 1;
b) adding the capture probe and the detection probe separately or combined to a sample containing the L-nucleic acid according to claim 1 or presumed to contain the L-nucleic acid according to claim 1;
c) allowing the capture probe and the detection probe to react either simultaneously or in any order sequentially with the L-nucleic acid according to claim 1 or part thereof;
d) optionally detecting whether or not the capture probe is hybridized to the L-nucleic acid according to claim 1 provided in step a); and
e) detecting a complex formed in step c) consisting of the L-nucleic acid according to claim 1 and the capture probe and the detection probe.

* * * * *

SEQUENCE LISTING

<160> NUMBER OF SEQ ID NOS: 135

<210> SEQ ID NO 1
<211> LENGTH: 48
<212> TYPE: RNA
<213> ORGANISM: Artificial
<220> FEATURE:
<223> OTHER INFORMATION: Synthetic

<400> SEQUENCE: 1
cgugcugucg gagacuacuc gucgaguaga aauagguccc cucccacg        48

<210> SEQ ID NO 2
<211> LENGTH: 50
<212> TYPE: RNA
<213> ORGANISM: Artificial
<220> FEATURE:
<223> OTHER INFORMATION: Synthetic

<400> SEQUENCE: 2
ccgugcuguc ggagacuacu cgucgaguag aaauaggucc ccucccacgg        50

<210> SEQ ID NO 3
<211> LENGTH: 48
<212> TYPE: RNA
<213> ORGANISM: Artificial
<220> FEATURE:
<223> OTHER INFORMATION: Synthetic

<400> SEQUENCE: 3
cgugcuguug gagacuacuu guuaaguaga uauagguucc cucccacg        48

<210> SEQ ID NO 4
<211> LENGTH: 50
<212> TYPE: RNA
<213> ORGANISM: Artificial
<220> FEATURE:
<223> OTHER INFORMATION: Synthetic

<400> SEQUENCE: 4
gcgugcuguc ggagacuacg cuucgcguag agauagagucc ccucccacgc        50

<210> SEQ ID NO 5
<211> LENGTH: 48
<212> TYPE: RNA
<213> ORGANISM: Artificial
<220> FEATURE:
<223> OTHER INFORMATION: Synthetic

<400> SEQUENCE: 5
gcagcugucg gagacucacc gucggugaga aauagguccc cucccugc        48

<210> SEQ ID NO 6
<211> LENGTH: 48
<212> TYPE: RNA
<213> ORGANISM: Artificial
<220> FEATURE:
<223> OTHER INFORMATION: Synthetic

<400> SEQUENCE: 6
cgugauaucg gagacuacuc guggaguaga aauagguccc cucccacg        48

<210> SEQ ID NO 7
<211> LENGTH: 50
<212> TYPE: RNA
<213> ORGANISM: Artificial

<220> FEATURE:
<223> OTHER INFORMATION: Synthetic

<400> SEQUENCE: 7
ccgugcuguc ggagacuacu caucgaguag aaauaggucc ccucccacgg       50

<210> SEQ ID NO 8
<211> LENGTH: 48
<212> TYPE: RNA
<213> ORGANISM: Artificial
<220> FEATURE:
<223> OTHER INFORMATION: Synthetic

<400> SEQUENCE: 8
cgugcagucg gagacuacuc aucgaguaga aauaggnccc uucccacg       48

<210> SEQ ID NO 9
<211> LENGTH: 48
<212> TYPE: RNA
<213> ORGANISM: Artificial
<220> FEATURE:
<223> OTHER INFORMATION: Synthetic

<400> SEQUENCE: 9
cgugcugucg gagacuacuc guagagugga gauaggnccc cucccacg       48

<210> SEQ ID NO 10
<211> LENGTH: 48
<212> TYPE: RNA
<213> ORGANISM: Artificial
<220> FEATURE:
<223> OTHER INFORMATION: Synthetic

<400> SEQUENCE: 10
cgugcugucg gagacuacuc guagaguaga gauaagnccc cuccuacg       48

<210> SEQ ID NO 11
<211> LENGTH: 50
<212> TYPE: RNA
<213> ORGANISM: Artificial
<220> FEATURE:
<223> OTHER INFORMATION: Synthetic

<400> SEQUENCE: 11
ccgugcuguc ggagacuacu cguagaguag auauaggucc ccucccacgg       50

<210> SEQ ID NO 12
<211> LENGTH: 50
<212> TYPE: RNA
<213> ORGANISM: Artificial
<220> FEATURE:
<223> OTHER INFORMATION: Synthetic

<400> SEQUENCE: 12
ccgugcuguc ggagacuacu cguagaguag aaauaggucc ccucccacgg       50

<210> SEQ ID NO 13
<211> LENGTH: 52
<212> TYPE: RNA
<213> ORGANISM: Artificial
<220> FEATURE:
<223> OTHER INFORMATION: Synthetic

<400> SEQUENCE: 13
gucaugcugu cggagacuac ucaucgagua gaaauagguc cccucccacg gc       52

```
<210> SEQ ID NO 14
<211> LENGTH: 52
<212> TYPE: RNA
<213> ORGANISM: Artificial
<220> FEATURE:
<223> OTHER INFORMATION: Synthetic

<400> SEQUENCE: 14
gccaugcugu cggagacuac ucaucgagua gaaauagauc cccucccaug gc            52

<210> SEQ ID NO 15
<211> LENGTH: 52
<212> TYPE: RNA
<213> ORGANISM: Artificial
<220> FEATURE:
<223> OTHER INFORMATION: Synthetic

<400> SEQUENCE: 15
gccgugcugu cggagacuac ucaucgagua gaaauagguc cccucccacg gc            52

<210> SEQ ID NO 16
<211> LENGTH: 52
<212> TYPE: RNA
<213> ORGANISM: Artificial
<220> FEATURE:
<223> OTHER INFORMATION: Synthetic

<400> SEQUENCE: 16
gccgugcugu cggagacuac ucguugagua gaaauagguc cccucccacg gc            52

<210> SEQ ID NO 17
<211> LENGTH: 52
<212> TYPE: RNA
<213> ORGANISM: Artificial
<220> FEATURE:
<223> OTHER INFORMATION: Synthetic

<400> SEQUENCE: 17
gccgugcugu cggagacuac ucguugagua gaaauagguc ccgucccacg gc            52

<210> SEQ ID NO 18
<211> LENGTH: 52
<212> TYPE: RNA
<213> ORGANISM: Artificial
<220> FEATURE:
<223> OTHER INFORMATION: Synthetic

<400> SEQUENCE: 18
gccgugcugu cggagacuac ucgccgagua gaaauagguc cccucccacg gc            52

<210> SEQ ID NO 19
<211> LENGTH: 52
<212> TYPE: RNA
<213> ORGANISM: Artificial
<220> FEATURE:
<223> OTHER INFORMATION: Synthetic

<400> SEQUENCE: 19
cccgugcugu cggagacuac ucgucgagua gaaauagguc cccucccacg gg            52

<210> SEQ ID NO 20
<211> LENGTH: 54
<212> TYPE: RNA
<213> ORGANISM: Artificial
<220> FEATURE:
<223> OTHER INFORMATION: Synthetic
```

```
<400> SEQUENCE: 20
caccgugcug ucggauacua cucgccgagu agaaauaggu ccccucccac ggug            54

<210> SEQ ID NO 21
<211> LENGTH: 54
<212> TYPE: RNA
<213> ORGANISM: Artificial
<220> FEATURE:
<223> OTHER INFORMATION: Synthetic

<400> SEQUENCE: 21
ggccgugcug ucggagacua cucgccgagu agaaauaggu ccccucccac ggcu            54

<210> SEQ ID NO 22
<211> LENGTH: 52
<212> TYPE: RNA
<213> ORGANISM: Artificial
<220> FEATURE:
<223> OTHER INFORMATION: Synthetic

<400> SEQUENCE: 22
cccgugcugu cggagacuac ucguagggua gaaauagguc cccucccacg gg              52

<210> SEQ ID NO 23
<211> LENGTH: 52
<212> TYPE: RNA
<213> ORGANISM: Artificial
<220> FEATURE:
<223> OTHER INFORMATION: Synthetic

<400> SEQUENCE: 23
gccguguugu cggagacuac ccccagggua gaaauagguc cccucccacg gc              52

<210> SEQ ID NO 24
<211> LENGTH: 50
<212> TYPE: RNA
<213> ORGANISM: Artificial
<220> FEATURE:
<223> OTHER INFORMATION: Synthetic

<400> SEQUENCE: 24
gcgugcuguc ggagacuacu cgucgaguag aaauaggucc ccucccacgc                 50

<210> SEQ ID NO 25
<211> LENGTH: 50
<212> TYPE: RNA
<213> ORGANISM: Artificial
<220> FEATURE:
<223> OTHER INFORMATION: Synthetic

<400> SEQUENCE: 25
gggugcuguc ggagacuacu cgucgaguag aaauaggucc ccucccaccc                 50

<210> SEQ ID NO 26
<211> LENGTH: 50
<212> TYPE: RNA
<213> ORGANISM: Artificial
<220> FEATURE:
<223> OTHER INFORMATION: Synthetic

<400> SEQUENCE: 26
gccugcuguc ggagacuacu cgucgaguag aaauaggucc ccucccaggc                 50

<210> SEQ ID NO 27
```

```
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Deoxyribonucleotide rather than ribonucleotide

<400> SEQUENCE: 27
ccgugcuguc ggagacuacu cgucgaguag aaauaggucc ccucccacgg           50

<210> SEQ ID NO 28
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Deoxyribonucleotide rather than ribonucleotide

<400> SEQUENCE: 28
ccgugcuguc ggagacuacu cgucgaguag aaauaggucc ccucccacgg           50

<210> SEQ ID NO 29
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Deoxyribonucleotide rather than ribonucleotide

<400> SEQUENCE: 29
ccgugcuguc ggagacuacu cgucgaguag aaauaggucc ccucccacgg           50

<210> SEQ ID NO 30
<211> LENGTH: 50
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(8)
<223> OTHER INFORMATION: Ribonucleotide rather than deoxyribonucleotide
<220> FEATURE:
<221> NAME/KEY: misc_feature
<222> LOCATION: (10)..(50)
<223> OTHER INFORMATION: Ribonucleotide rather than deoxyribonucleotide

<400> SEQUENCE: 30
ccgugcugtc ggagacuacu cgucgaguag aaauaggucc ccucccacgg           50

<210> SEQ ID NO 31
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(13)
<223> OTHER INFORMATION: Ribonucleotide rather than deoxyribonucleotide
<220> FEATURE:
<221> NAME/KEY: misc_feature
```

<222> LOCATION: (15)..(50)
<223> OTHER INFORMATION: Ribonucleotide rather than deoxyribonucleotide

<400> SEQUENCE: 31
ccgugcuguc ggagacuacu cgucgaguag aaauaggucc ccucccacgg    50

<210> SEQ ID NO 32
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(15)
<223> OTHER INFORMATION: Ribonucleotide rather than deoxyribonucleotide
<220> FEATURE:
<221> NAME/KEY: misc_feature
<222> LOCATION: (17)..(50)
<223> OTHER INFORMATION: Ribonucleotide rather than deoxyribonucleotide

<400> SEQUENCE: 32
ccgugcuguc ggagacuacu cgucgaguag aaauaggucc ccucccacgg    50

<210> SEQ ID NO 33
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(18)
<223> OTHER INFORMATION: Ribonucleotide rather than deoxyribonucleotide
<220> FEATURE:
<221> NAME/KEY: misc_feature
<222> LOCATION: (20)..(50)
<223> OTHER INFORMATION: Ribonucleotide rather than deoxyribonucleotide

<400> SEQUENCE: 33
ccgugcuguc ggagacuacu cgucgaguag aaauaggucc ccucccacgg    50

<210> SEQ ID NO 34
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(21)
<223> OTHER INFORMATION: Ribonucleotide rather than deoxyribonucleotide
<220> FEATURE:
<221> NAME/KEY: misc_feature
<222> LOCATION: (23)..(50)
<223> OTHER INFORMATION: Ribonucleotide rather than deoxyribonucleotide

<400> SEQUENCE: 34
ccgugcuguc ggagacuacu cgucgaguag aaauaggucc ccucccacgg    50

<210> SEQ ID NO 35
<211> LENGTH: 50
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(22)
<223> OTHER INFORMATION: Ribonucleotide rather than deoxyribonucleotide
<220> FEATURE:

```
<221> NAME/KEY: misc_feature
<222> LOCATION: (24)..(24)
<223> OTHER INFORMATION: Ribonucleotide rather than deoxyribonucleotide

<400> SEQUENCE: 35
ccgugcuguc ggagacuacu cgtcgaguag aaauaggucc ccucccacgg            50

<210> SEQ ID NO 36
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (24)..(24)
<223> OTHER INFORMATION: Deoxyribonucleotide rather than ribonucleotide

<400> SEQUENCE: 36
ccgugcuguc ggagacuacu cgucgaguag aaauaggucc ccucccacgg            50

<210> SEQ ID NO 37
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (25)..(25)
<223> OTHER INFORMATION: Deoxyribonucleotide rather than ribonucleotide

<400> SEQUENCE: 37
ccgugcuguc ggagacuacu cgucgaguag aaauaggucc ccucccacgg            50

<210> SEQ ID NO 38
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (26)..(26)
<223> OTHER INFORMATION: Deoxyribonucleotide rather than ribonucleotide

<400> SEQUENCE: 38
ccgugcuguc ggagacuacu cgucgaguag aaauaggucc ccucccacgg            50

<210> SEQ ID NO 39
<211> LENGTH: 50
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(27)
<223> OTHER INFORMATION: Ribonucleotide rather than deoxyribonucleotide
<220> FEATURE:
<221> NAME/KEY: misc_feature
<222> LOCATION: (29)..(50)
<223> OTHER INFORMATION: Ribonucleotide rather than deoxyribonucleotide

<400> SEQUENCE: 39
ccgugcuguc ggagacuacu cgucgagtag aaauaggucc ccucccacgg            50

<210> SEQ ID NO 40
<211> LENGTH: 50
```

```
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (30)..(30)
<223> OTHER INFORMATION: Deoxyribonucleotide rather than ribonucleotide

<400> SEQUENCE: 40
ccgugcuguc ggagacuacu cgucgaguag aaauaggucc ccucccacgg            50

<210> SEQ ID NO 41
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Deoxyribonucleotide rather than ribonucleotide

<400> SEQUENCE: 41
ccgugcuguc ggagacuacu cgucgaguag aaauaggucc ccucccacgg            50

<210> SEQ ID NO 42
<211> LENGTH: 50
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(33)
<223> OTHER INFORMATION: Ribonucleotide rather than deoxyribonucleotide
<220> FEATURE:
<221> NAME/KEY: misc_feature
<222> LOCATION: (35)..(50)
<223> OTHER INFORMATION: Ribonucleotide rather than deoxyribonucleotide

<400> SEQUENCE: 42
ccgugcuguc ggagacuacu cgucgaguag aaataggucc ccucccacgg            50

<210> SEQ ID NO 43
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (37)..(37)
<223> OTHER INFORMATION: Deoxyribonucleotide rather than ribonucleotide

<400> SEQUENCE: 43
ccgugcuguc ggagacuacu cgucgaguag aaauaggucc ccucccacgg            50

<210> SEQ ID NO 44
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (39)..(39)
<223> OTHER INFORMATION: Deoxyribonucleotide rather than ribonucleotide

<400> SEQUENCE: 44
```
ccgugcuguc ggagacuacu cgucgaguag aaauaggucc ccucccacgg            50

<210> SEQ ID NO 45
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (41)..(41)
<223> OTHER INFORMATION: Deoxyribonucleotide rather than ribonucleotide

<400> SEQUENCE: 45
ccgugcuguc ggagacuacu cgucgaguag aaauaggucc ccucccacgg            50

<210> SEQ ID NO 46
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (42)..(42)
<223> OTHER INFORMATION: Deoxyribonucleotide rather than ribonucleotide

<400> SEQUENCE: 46
ccgugcuguc ggagacuacu cgucgaguag aaauaggucc ccucccacgg            50

<210> SEQ ID NO 47
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (44)..(44)
<223> OTHER INFORMATION: Deoxyribonucleotide rather than ribonucleotide

<400> SEQUENCE: 47
ccgugcuguc ggagacuacu cgucgaguag aaauaggucc ccucccacgg            50

<210> SEQ ID NO 48
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (45)..(45)
<223> OTHER INFORMATION: Deoxyribonucleotide rather than ribonucleotide

<400> SEQUENCE: 48
ccgugcuguc ggagacuacu cgucgaguag aaauaggucc ccucccacgg            50

<210> SEQ ID NO 49
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (46)..(46)
<223> OTHER INFORMATION: Deoxyribonucleotide rather than ribonucleotide

<400> SEQUENCE: 49
ccgugcuguc ggagacuacu cgucgaguag aaauaggucc ccucccacgg    50

<210> SEQ ID NO 50
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (47)..(47)
<223> OTHER INFORMATION: Deoxyribonucleotide rather than ribonucleotide

<400> SEQUENCE: 50
ccgugcuguc ggagacuacu cgucgaguag aaauaggucc ccucccacgg    50

<210> SEQ ID NO 51
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (48)..(48)
<223> OTHER INFORMATION: Deoxyribonucleotide rather than ribonucleotide

<400> SEQUENCE: 51
ccgugcuguc ggagacuacu cgucgaguag aaauaggucc ccucccacgg    50

<210> SEQ ID NO 52
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (49)..(49)
<223> OTHER INFORMATION: Deoxyribonucleotide rather than ribonucleotide

<400> SEQUENCE: 52
ccgugcuguc ggagacuacu cgucgaguag aaauaggucc ccucccacgg    50

<210> SEQ ID NO 53
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (50)..(50)
<223> OTHER INFORMATION: Deoxyribonucleotide rather than ribonucleotide

<400> SEQUENCE: 53
ccgugcuguc ggagacuacu cgucgaguag aaauaggucc ccucccacgg    50

<210> SEQ ID NO 54
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (41)..(41)
<223> OTHER INFORMATION: Deoxyribonucleotide rather than ribonucleotide
<220> FEATURE:

```
<221> NAME/KEY: misc_feature
<222> LOCATION: (44)..(44)
<223> OTHER INFORMATION: Deoxyribonucleotide rather than ribonucleotide

<400> SEQUENCE: 54
ccgugcuguc ggagacuacu cgucgaguag aaauaggucc ccucccacgg         50

<210> SEQ ID NO 55
<211> LENGTH: 48
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(48)
<223> OTHER INFORMATION: D-RNA

<400> SEQUENCE: 55
cgugcugucg gagacuacuc gucgaguaga aauaggnccc cucccacg           48

<210> SEQ ID NO 56
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(50)
<223> OTHER INFORMATION: D-RNA

<400> SEQUENCE: 56
ccgugcuguc ggagacuacu cgucgaguag aaauaggucc ccucccacgg         50

<210> SEQ ID NO 57
<211> LENGTH: 48
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(48)
<223> OTHER INFORMATION: D-RNA

<400> SEQUENCE: 57
cgugcuguug gagacuacuu guuaaguaga uauagguucc cucccacg           48

<210> SEQ ID NO 58
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(50)
<223> OTHER INFORMATION: D-RNA

<400> SEQUENCE: 58
gcgugcuguc ggagacuacg cuucgcguag agauaggucc ccucccacgc         50

<210> SEQ ID NO 59
<211> LENGTH: 48
<212> TYPE: RNA
<213> ORGANISM: Artificial
<220> FEATURE:
<223> OTHER INFORMATION: Synthetic
```

```
<220> FEATURE:
<221> NAME/KEY: misc_feature
<222> LOCATION: (1)..(48)
<223> OTHER INFORMATION: D-RNA

<400> SEQUENCE: 59
gcagcugucg gagacucacc gucggugaga aauagguccc cucccugc         48

<210> SEQ ID NO 60
<211> LENGTH: 48
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(48)
<223> OTHER INFORMATION: D-RNA

<400> SEQUENCE: 60
cgugauaucg gagacuacuc guggaguaga aauagguccc cucccacg         48

<210> SEQ ID NO 61
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(50)
<223> OTHER INFORMATION: D-RNA

<400> SEQUENCE: 61
ccgugcuguc ggagacuacu caucgaguag aaauaggucc ccucccacgg       50

<210> SEQ ID NO 62
<211> LENGTH: 48
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(48)
<223> OTHER INFORMATION: D-RNA

<400> SEQUENCE: 62
cgugcagucg gagacuacuc aucgaguaga aauagguccc uucccacg         48

<210> SEQ ID NO 63
<211> LENGTH: 48
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(48)
<223> OTHER INFORMATION: D-RNA

<400> SEQUENCE: 63
cgugcugucg gagacuacuc guagagugga gauagguccc cucccacg         48

<210> SEQ ID NO 64
<211> LENGTH: 48
<212> TYPE: RNA
<213> ORGANISM: Artificial
<220> FEATURE:
```

<223> OTHER INFORMATION: Synthetic
<220> FEATURE:
<221> NAME/KEY: misc_feature
<222> LOCATION: (1)..(48)
<223> OTHER INFORMATION: D-RNA

<400> SEQUENCE: 64
cgugcugucg gagacuacuc guagaguaga gauaagcccc cuccuacg          48

<210> SEQ ID NO 65
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(50)
<223> OTHER INFORMATION: D-RNA

<400> SEQUENCE: 65
ccgugcuguc ggagacuacu cguagaguag auauaggucc ccucccacgg          50

<210> SEQ ID NO 66
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(50)
<223> OTHER INFORMATION: D-RNA

<400> SEQUENCE: 66
ccgugcuguc ggagacuacu cguagaguag aaauaggucc ccucccacgg          50

<210> SEQ ID NO 67
<211> LENGTH: 52
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(52)
<223> OTHER INFORMATION: D-RNA

<400> SEQUENCE: 67
gucaugcugu cggagacuac ucaucgagua gaaauagguc cccucccacg gc          52

<210> SEQ ID NO 68
<211> LENGTH: 52
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(52)
<223> OTHER INFORMATION: D-RNA

<400> SEQUENCE: 68
gccaugcugu cggagacuac ucaucgagua gaaauagauc cccucccaug gc          52

<210> SEQ ID NO 69
<211> LENGTH: 52
<212> TYPE: RNA
<213> ORGANISM: Artificial

```
<220> FEATURE:
<223> OTHER INFORMATION: Synthetic
<220> FEATURE:
<221> NAME/KEY: misc_feature
<222> LOCATION: (1)..(52)
<223> OTHER INFORMATION: D-RNA

<400> SEQUENCE: 69
gccgugcugu cggagacuac ucaucgagua gaaauagguc cccucccacg gc      52

<210> SEQ ID NO 70
<211> LENGTH: 52
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(52)
<223> OTHER INFORMATION: D-RNA

<400> SEQUENCE: 70
gccgugcugu cggagacuac ucguugagua gaaauagguc cccucccacg gc      52

<210> SEQ ID NO 71
<211> LENGTH: 52
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(52)
<223> OTHER INFORMATION: D-RNA

<400> SEQUENCE: 71
gccgugcugu cggagacuac ucguugagua gaaauagguc ccgucccacg gc      52

<210> SEQ ID NO 72
<211> LENGTH: 52
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(52)
<223> OTHER INFORMATION: D-RNA

<400> SEQUENCE: 72
gccgugcugu cggagacuac ucgccgagua gaaauagguc cccucccacg gc      52

<210> SEQ ID NO 73
<211> LENGTH: 52
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(52)
<223> OTHER INFORMATION: D-RNA

<400> SEQUENCE: 73
cccgugcugu cggagacuac ucgucgagua gaaauagguc cccucccacg gg      52

<210> SEQ ID NO 74
<211> LENGTH: 54
<212> TYPE: RNA
```

```
<213> ORGANISM: Artificial
<220> FEATURE:
<223> OTHER INFORMATION: Synthetic
<220> FEATURE:
<221> NAME/KEY: misc_feature
<222> LOCATION: (1)..(54)
<223> OTHER INFORMATION: D-RNA

<400> SEQUENCE: 74
caccgugcug ucggauacua cucgccgagu agaaauaggu ccccucccac ggug      54

<210> SEQ ID NO 75
<211> LENGTH: 54
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(54)
<223> OTHER INFORMATION: D-RNA

<400> SEQUENCE: 75
ggccgugcug ucggagacua cucgccgagu agaaauaggu ccccucccac ggcu      54

<210> SEQ ID NO 76
<211> LENGTH: 52
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(52)
<223> OTHER INFORMATION: D-RNA

<400> SEQUENCE: 76
cccgugcugu cggagacuac ucguagggua gaaauagguc cccucccacg gg        52

<210> SEQ ID NO 77
<211> LENGTH: 52
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(52)
<223> OTHER INFORMATION: D-RNA

<400> SEQUENCE: 77
gccguguugu cggagacuac ccccagggua gaaauagguc cccucccacg gc        52

<210> SEQ ID NO 78
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(50)
<223> OTHER INFORMATION: L-RNA
<220> FEATURE:
<221> NAME/KEY: misc_feature
<222> LOCATION: (1)..(1)
<223> OTHER INFORMATION: PEG attached
<220> FEATURE:
<221> NAME/KEY: misc_feature
<222> LOCATION: (41)..(41)
<223> OTHER INFORMATION: Deoxyribonucleotide rather than ribonucleotide
```

-continued

<400> SEQUENCE: 78
ccgugcuguc ggagacuacu cgucgaguag aaauaggucc ccucccacgg         50

<210> SEQ ID NO 79
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(50)
<223> OTHER INFORMATION: D-RNA

<400> SEQUENCE: 79
gcgugcuguc ggagacuacu cgucgaguag aaauaggucc ccucccacgc         50

<210> SEQ ID NO 80
<211> LENGTH: 50
<212> TYPE: RNA
<213> ORGANISM: Artificial
<220> FEATURE:
<223> OTHER INFORMATION: Synthtic
<220> FEATURE:
<221> NAME/KEY: misc_feature
<222> LOCATION: (1)..(50)
<223> OTHER INFORMATION: D-RNA

<400> SEQUENCE: 80
gggugcuguc ggagacuacu cgucgaguag aaauaggucc ccucccaccc         50

<210> SEQ ID NO 81
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(50)
<223> OTHER INFORMATION: D-RNA

<400> SEQUENCE: 81
gccugcuguc ggagacuacu cgucgaguag aaauaggucc ccucccaggc         50

<210> SEQ ID NO 82
<211> LENGTH: 37
<212> TYPE: PRT
<213> ORGANISM: Homo sapiens

<400> SEQUENCE: 82

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 83
<211> LENGTH: 37
<212> TYPE: PRT
<213> ORGANISM: Homo sapiens

<400> SEQUENCE: 83

Ala Cys Asn Thr Ala Thr Cys Val Thr His Arg Leu Ala Gly Leu Leu

```
                1               5                   10                  15
Ser Arg Ser Gly Gly Met Val Lys Ser Asn Phe Val Pro Thr Asn Val
                        20                  25                  30

Gly Ser Lys Ala Phe
            35
```

<210> SEQ ID NO 84
<211> LENGTH: 37
<212> TYPE: PRT
<213> ORGANISM: Homo sapiens

<400> SEQUENCE: 84

```
Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Thr Asn Val
                        20                  25                  30

Gly Ser Asn Thr Tyr
            35
```

<210> SEQ ID NO 85
<211> LENGTH: 32
<212> TYPE: PRT
<213> ORGANISM: Homo sapiens

<400> SEQUENCE: 85

```
Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
                        20                  25                  30
```

<210> SEQ ID NO 86
<211> LENGTH: 52
<212> TYPE: PRT
<213> ORGANISM: Homo sapiens

<400> SEQUENCE: 86

```
Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
                        20                  25                  30

Phe Thr Asp Lys Asp Lys Asp Asn Val Ala Pro Arg Ser Lys Ile Ser
                35                  40                  45

Pro Gln Gly Tyr
        50
```

<210> SEQ ID NO 87
<211> LENGTH: 47
<212> TYPE: PRT
<213> ORGANISM: Homo sapiens

<400> SEQUENCE: 87

```
Thr Gln Ala Gln Leu Leu Arg Val Gly Cys Val Leu Gly Thr Cys Gln
1               5                   10                  15

Val Gln Asn Leu Ser His Arg Leu Trp Gln Leu Met Gly Pro Ala Gly
                        20                  25                  30

Arg Gln Asp Ser Ala Pro Val Asp Pro Ser Ser Pro His Ser Tyr
                35                  40                  45
```

<210> SEQ ID NO 88
<211> LENGTH: 50

```
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(50)
<223> OTHER INFORMATION: L-RNA
<220> FEATURE:
<221> NAME/KEY: misc_feature
<222> LOCATION: (1)..(1)
<223> OTHER INFORMATION: PEG attached

<400> SEQUENCE: 88
ccgugcuguc ggagacuacu cgucgaguag aaauaggucc ccucccacgg            50

<210> SEQ ID NO 89
<211> LENGTH: 37
<212> TYPE: PRT
<213> ORGANISM: Mus musculus

<400> SEQUENCE: 89

Ser Cys Asn Thr Ala Thr Cys Val Thr His Arg Leu Ala Gly Leu Leu
1               5                  10                  15

Ser Arg Ser Gly Gly Val Val Lys Asp Asn Phe Val Pro Thr Asn Val
            20                  25                  30

Gly Ser Glu Ala Phe
        35

<210> SEQ ID NO 90
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (15)..(15)
<223> OTHER INFORMATION: Deoxyribonucleotide rather than ribonucleotide
<220> FEATURE:
<221> NAME/KEY: misc_feature
<222> LOCATION: (23)..(23)
<223> OTHER INFORMATION: Deoxyribonucleotide rather than ribonucleotide
<220> FEATURE:
<221> NAME/KEY: misc_feature
<222> LOCATION: (36)..(36)
<223> OTHER INFORMATION: Deoxyribonucleotide rather than ribonucleotide
<220> FEATURE:
<221> NAME/KEY: misc_feature
<222> LOCATION: (39)..(39)
<223> OTHER INFORMATION: Deoxyribonucleotide rather than ribonucleotide

<400> SEQUENCE: 90
cugucggaga cuacucgucg aguagaaaua gguccccucc                      40

<210> SEQ ID NO 91
<211> LENGTH: 37
<212> TYPE: PRT
<213> ORGANISM: Sus scrofa

<400> SEQUENCE: 91

Ser Cys Asn Thr Ala Thr Cys Val Thr His Arg Leu Ala Gly Leu Leu
1               5                  10                  15

Ser Arg Ser Gly Gly Met Val Lys Ser Asn Phe Val Pro Thr Asp Val
            20                  25                  30
```

```
Gly Ser Glu Ala Phe
        35

<210> SEQ ID NO 92
<211> LENGTH: 37
<212> TYPE: PRT
<213> ORGANISM: Sheep

<400> SEQUENCE: 92

Ser Cys Asn Thr Ala Thr Cys Val Thr His Arg Leu Ala Gly Leu Leu
1               5                   10                  15

Ser Arg Ser Gly Gly Val Val Lys Ser Asn Phe Val Pro Thr Asn Val
            20                  25                  30

Gly Ser Gln Ala Phe
        35

<210> SEQ ID NO 93
<211> LENGTH: 37
<212> TYPE: PRT
<213> ORGANISM: Canis familiaris

<400> SEQUENCE: 93

Ser Cys Asn Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Glu Ala Phe
        35

<210> SEQ ID NO 94
<211> LENGTH: 37
<212> TYPE: PRT
<213> ORGANISM: Rattus norvegicus

<400> SEQUENCE: 94

Lys Cys Asn Thr Ala Thr Cys Ala Thr Gln Arg Leu Ala Asn Phe Leu
1               5                   10                  15

Val Arg Ser Ser Asn Asn Phe Gly Ala Ile Leu Ser Pro Thr Asn Val
            20                  25                  30

Gly Ser Asn Thr Tyr
        35

<210> SEQ ID NO 95
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid

<400> SEQUENCE: 95
hwruyggaka cummbynynr vkkrgadaua rruyccbucc                    40

<210> SEQ ID NO 96
<211> LENGTH: 40
<212> TYPE: RNA
<213> ORGANISM: Artificial
<220> FEATURE:
<223> OTHER INFORMATION: Synthetic
<220> FEATURE:
```

<221> NAME/KEY: misc_feature
<223> OTHER INFORMATION: L-nucleic acid

<400> SEQUENCE: 96
cuguyggaga cummubdyhr vkkagadaua gguyccaucc                                40

<210> SEQ ID NO 97
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid

<400> SEQUENCE: 97
cugucggaga cuacucryhg rguagaaaua gguccccucc                                40

<210> SEQ ID NO 98
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<223> OTHER INFORMATION: L-nucleic acid

<400> SEQUENCE: 98
cugucggaga cuacucgucg aguagaaaua gguccccucc                                40

<210> SEQ ID NO 99
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (3)..(3)
<223> OTHER INFORMATION: n is R or dG
<220> FEATURE:
<221> NAME/KEY: misc_feature
<222> LOCATION: (4)..(4)
<223> OTHER INFORMATION: n is U or dT
<220> FEATURE:
<221> NAME/KEY: misc_feature
<222> LOCATION: (9)..(9)
<223> OTHER INFORMATION: n is K or dG
<220> FEATURE:
<221> NAME/KEY: misc_feature
<222> LOCATION: (11)..(11)
<223> OTHER INFORMATION: n is C or dC
<220> FEATURE:
<221> NAME/KEY: misc_feature
<222> LOCATION: (14)..(14)
<223> OTHER INFORMATION: n is M or dC
<220> FEATURE:
<221> NAME/KEY: misc_feature
<222> LOCATION: (15)..(15)
<223> OTHER INFORMATION: n is B or dU
<220> FEATURE:
<221> NAME/KEY: misc_feature
<222> LOCATION: (17)..(17)
<223> OTHER INFORMATION: n is N or dG
<220> FEATURE:
<221> NAME/KEY: misc_feature

```
<222> LOCATION: (18)..(18)
<223> OTHER INFORMATION: n is Y or dT
<220> FEATURE:
<221> NAME/KEY: misc_feature
<222> LOCATION: (19)..(19)
<223> OTHER INFORMATION: n is N or dC
<220> FEATURE:
<221> NAME/KEY: misc_feature
<222> LOCATION: (20)..(20)
<223> OTHER INFORMATION: n is R or dG
<220> FEATURE:
<221> NAME/KEY: misc_feature
<222> LOCATION: (21)..(21)
<223> OTHER INFORMATION: n is V or dA
<220> FEATURE:
<221> NAME/KEY: misc_feature
<222> LOCATION: (23)..(23)
<223> OTHER INFORMATION: n is K or dT or dU
<220> FEATURE:
<221> NAME/KEY: misc_feature
<222> LOCATION: (25)..(25)
<223> OTHER INFORMATION: n is KG or dG
<220> FEATURE:
<221> NAME/KEY: misc_feature
<222> LOCATION: (28)..(28)
<223> OTHER INFORMATION: n is A or dA
<220> FEATURE:
<221> NAME/KEY: misc_feature
<222> LOCATION: (28)..(28)
<223> OTHER INFORMATION: n is A or dA
<220> FEATURE:
<221> NAME/KEY: misc_feature
<222> LOCATION: (29)..(29)
<223> OTHER INFORMATION: n is U or dT
<220> FEATURE:
<221> NAME/KEY: misc_feature
<222> LOCATION: (32)..(32)
<223> OTHER INFORMATION: n is R or dG
<220> FEATURE:
<221> NAME/KEY: misc_feature
<222> LOCATION: (34)..(34)
<223> OTHER INFORMATION: n is Y or dC
<220> FEATURE:
<221> NAME/KEY: misc_feature
<222> LOCATION: (36)..(36)
<223> OTHER INFORMATION: n is C or dC
<220> FEATURE:
<221> NAME/KEY: misc_feature
<222> LOCATION: (37)..(37)
<223> OTHER INFORMATION: n is B or dC
<220> FEATURE:
<221> NAME/KEY: misc_feature
<222> LOCATION: (39)..(39)
<223> OTHER INFORMATION: n is C or dC
<220> FEATURE:
<221> NAME/KEY: misc_feature
<222> LOCATION: (40)..(40)
<223> OTHER INFORMATION: n is C or dC

<400> SEQUENCE: 99
hwnnyggana numnnynnnn nknrnadnna rnuncnnunn                              40

<210> SEQ ID NO 100
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (3)..(3)
<223> OTHER INFORMATION: n is G ior dG
<220> FEATURE:
```

-continued

```
<221> NAME/KEY: misc_feature
<222> LOCATION: (4)..(4)
<223> OTHER INFORMATION: n is U or dT
<220> FEATURE:
<221> NAME/KEY: misc_feature
<222> LOCATION: (9)..(9)
<223> OTHER INFORMATION: n is G or dG
<220> FEATURE:
<221> NAME/KEY: misc_feature
<222> LOCATION: (11)..(11)
<223> OTHER INFORMATION: n is C or dC
<220> FEATURE:
<221> NAME/KEY: misc_feature
<222> LOCATION: (14)..(14)
<223> OTHER INFORMATION: n is M or dC
<220> FEATURE:
<221> NAME/KEY: misc_feature
<222> LOCATION: (15)..(15)
<223> OTHER INFORMATION: n is B or dU
<220> FEATURE:
<221> NAME/KEY: misc_feature
<222> LOCATION: (17)..(17)
<223> OTHER INFORMATION: n is D or dG
<220> FEATURE:
<221> NAME/KEY: misc_feature
<222> LOCATION: (18)..(18)
<223> OTHER INFORMATION: n is Y or dT
<220> FEATURE:
<221> NAME/KEY: misc_feature
<222> LOCATION: (19)..(19)
<223> OTHER INFORMATION: n is H or dC
<220> FEATURE:
<221> NAME/KEY: misc_feature
<222> LOCATION: (20)..(20)
<223> OTHER INFORMATION: n is R or dG
<220> FEATURE:
<221> NAME/KEY: misc_feature
<222> LOCATION: (21)..(21)
<223> OTHER INFORMATION: n is V or dA
<220> FEATURE:
<221> NAME/KEY: misc_feature
<222> LOCATION: (23)..(23)
<223> OTHER INFORMATION: n is K or dT or dU
<220> FEATURE:
<221> NAME/KEY: misc_feature
<222> LOCATION: (25)..(25)
<223> OTHER INFORMATION: n is G or dG
<220> FEATURE:
<221> NAME/KEY: misc_feature
<222> LOCATION: (28)..(28)
<223> OTHER INFORMATION: n is A or dA
<220> FEATURE:
<221> NAME/KEY: misc_feature
<222> LOCATION: (29)..(29)
<223> OTHER INFORMATION: n is U or dT
<220> FEATURE:
<221> NAME/KEY: misc_feature
<222> LOCATION: (32)..(32)
<223> OTHER INFORMATION: n is G or dG
<220> FEATURE:
<221> NAME/KEY: misc_feature
<222> LOCATION: (34)..(34)
<223> OTHER INFORMATION: n is Y or dC
<220> FEATURE:
<221> NAME/KEY: misc_feature
<222> LOCATION: (36)..(36)
<223> OTHER INFORMATION: n is C or dC
<220> FEATURE:
<221> NAME/KEY: misc_feature
<222> LOCATION: (37)..(37)
<223> OTHER INFORMATION: n is C or dC
<220> FEATURE:
<221> NAME/KEY: misc_feature
<222> LOCATION: (39)..(39)
<223> OTHER INFORMATION: n is C or dC
<220> FEATURE:
<221> NAME/KEY: misc_feature
<222> LOCATION: (40)..(40)
<223> OTHER INFORMATION: n is C or dC
```

<400> SEQUENCE: 100
cunnyggana numnnbnnnn nknanadnna gnuncnnunn                40

<210> SEQ ID NO 101
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (3)..(3)
<223> OTHER INFORMATION: n is G or dG
<220> FEATURE:
<221> NAME/KEY: misc_feature
<222> LOCATION: (4)..(4)
<223> OTHER INFORMATION: n is U or dT
<220> FEATURE:
<221> NAME/KEY: misc_feature
<222> LOCATION: (9)..(9)
<223> OTHER INFORMATION: n is G or dG
<220> FEATURE:
<221> NAME/KEY: misc_feature
<222> LOCATION: (11)..(11)
<223> OTHER INFORMATION: n is C or dC
<220> FEATURE:
<221> NAME/KEY: misc_feature
<222> LOCATION: (14)..(14)
<223> OTHER INFORMATION: n is C or dC
<220> FEATURE:
<221> NAME/KEY: misc_feature
<222> LOCATION: (15)..(15)
<223> OTHER INFORMATION: n is U or dU
<220> FEATURE:
<221> NAME/KEY: misc_feature
<222> LOCATION: (17)..(17)
<223> OTHER INFORMATION: n is R or dG
<220> FEATURE:
<221> NAME/KEY: misc_feature
<222> LOCATION: (18)..(18)
<223> OTHER INFORMATION: n is Y or dT
<220> FEATURE:
<221> NAME/KEY: misc_feature
<222> LOCATION: (19)..(19)
<223> OTHER INFORMATION: n is H or dC
<220> FEATURE:
<221> NAME/KEY: misc_feature
<222> LOCATION: (20)..(20)
<223> OTHER INFORMATION: n is G or dG
<220> FEATURE:
<221> NAME/KEY: misc_feature
<222> LOCATION: (21)..(21)
<223> OTHER INFORMATION: n is R or dA
<220> FEATURE:
<221> NAME/KEY: misc_feature
<222> LOCATION: (23)..(23)
<223> OTHER INFORMATION: n is U or dT or dU
<220> FEATURE:
<221> NAME/KEY: misc_feature
<222> LOCATION: (25)..(25)
<223> OTHER INFORMATION: n is G or dG
<220> FEATURE:
<221> NAME/KEY: misc_feature
<222> LOCATION: (28)..(28)
<223> OTHER INFORMATION: n is A or dA
<220> FEATURE:
<221> NAME/KEY: misc_feature
<222> LOCATION: (29)..(29)
<223> OTHER INFORMATION: n is U or dT
<220> FEATURE:
<221> NAME/KEY: misc_feature
<222> LOCATION: (32)..(32)

```
<223> OTHER INFORMATION: n is G or dG
<220> FEATURE:
<221> NAME/KEY: misc_feature
<222> LOCATION: (34)..(34)
<223> OTHER INFORMATION: n is C or dC
<220> FEATURE:
<221> NAME/KEY: misc_feature
<222> LOCATION: (36)..(36)
<223> OTHER INFORMATION: n is C or dC
<220> FEATURE:
<221> NAME/KEY: misc_feature
<222> LOCATION: (37)..(37)
<223> OTHER INFORMATION: n is C or dC
<220> FEATURE:
<221> NAME/KEY: misc_feature
<222> LOCATION: (39)..(39)
<223> OTHER INFORMATION: n is C or dC
<220> FEATURE:
<221> NAME/KEY: misc_feature
<222> LOCATION: (40)..(40)
<223> OTHER INFORMATION: n is C or dC

<400> SEQUENCE: 101
cunncggana nuanncnnnn ngnanaanna gnuncnnunn                              40

<210> SEQ ID NO 102
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L- nucleic acid
<220> FEATURE:
<221> NAME/KEY: misc_feature
<222> LOCATION: (3)..(3)
<223> OTHER INFORMATION: n is G or dG
<220> FEATURE:
<221> NAME/KEY: misc_feature
<222> LOCATION: (4)..(4)
<223> OTHER INFORMATION: n is U or dT
<220> FEATURE:
<221> NAME/KEY: misc_feature
<222> LOCATION: (9)..(9)
<223> OTHER INFORMATION: n is G or dG
<220> FEATURE:
<221> NAME/KEY: misc_feature
<222> LOCATION: (11)..(11)
<223> OTHER INFORMATION: n is C or dC
<220> FEATURE:
<221> NAME/KEY: misc_feature
<222> LOCATION: (14)..(14)
<223> OTHER INFORMATION: n is C or dC
<220> FEATURE:
<221> NAME/KEY: misc_feature
<222> LOCATION: (15)..(15)
<223> OTHER INFORMATION: n is U or dU
<220> FEATURE:
<221> NAME/KEY: misc_feature
<222> LOCATION: (17)..(17)
<223> OTHER INFORMATION: n is G or dG
<220> FEATURE:
<221> NAME/KEY: misc_feature
<222> LOCATION: (18)..(18)
<223> OTHER INFORMATION: n is U or dT
<220> FEATURE:
<221> NAME/KEY: misc_feature
<222> LOCATION: (19)..(19)
<223> OTHER INFORMATION: n is C or dC
<220> FEATURE:
<221> NAME/KEY: misc_feature
<222> LOCATION: (20)..(20)
<223> OTHER INFORMATION: n is G or dG
<220> FEATURE:
<221> NAME/KEY: misc_feature
```

```
<222> LOCATION: (21)..(21)
<223> OTHER INFORMATION: n is A or dA
<220> FEATURE:
<221> NAME/KEY: misc_feature
<222> LOCATION: (23)..(23)
<223> OTHER INFORMATION: n is U or dT or dU
<220> FEATURE:
<221> NAME/KEY: misc_feature
<222> LOCATION: (25)..(25)
<223> OTHER INFORMATION: n is Gor dG
<220> FEATURE:
<221> NAME/KEY: misc_feature
<222> LOCATION: (28)..(28)
<223> OTHER INFORMATION: n isA or dA
<220> FEATURE:
<221> NAME/KEY: misc_feature
<222> LOCATION: (29)..(29)
<223> OTHER INFORMATION: n is U or dT
<220> FEATURE:
<221> NAME/KEY: misc_feature
<222> LOCATION: (32)..(32)
<223> OTHER INFORMATION: n is G or dG
<220> FEATURE:
<221> NAME/KEY: misc_feature
<222> LOCATION: (34)..(34)
<223> OTHER INFORMATION: n is C or dC
<220> FEATURE:
<221> NAME/KEY: misc_feature
<222> LOCATION: (36)..(36)
<223> OTHER INFORMATION: n is C or dC
<220> FEATURE:
<221> NAME/KEY: misc_feature
<222> LOCATION: (37)..(37)
<223> OTHER INFORMATION: n is C or dC
<220> FEATURE:
<221> NAME/KEY: misc_feature
<222> LOCATION: (39)..(39)
<223> OTHER INFORMATION: n is C or dC
<220> FEATURE:
<221> NAME/KEY: misc_feature
<222> LOCATION: (40)..(40)
<223> OTHER INFORMATION: n is C or dC

<400> SEQUENCE: 102
cunncggana nuanncnnnn ngnanaanna gnuncnnunn                              40

<210> SEQ ID NO 103
<211> LENGTH: 40
<212> TYPE: RNA
<213> ORGANISM: Artificial
<220> FEATURE:
<223> OTHER INFORMATION: Syntehtic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (3)..(3)
<223> OTHER INFORMATION: Deoxyribonucleotide rather than ribonucleotide

<400> SEQUENCE: 103
cugucggaga cuacucgucg aguagaaaua ggucccoucc                              40

<210> SEQ ID NO 104
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
```

```
<221> NAME/KEY: misc_feature
<222> LOCATION: (1)..(3)
<223> OTHER INFORMATION: Ribonucleotide rather than deoxyribonucleotide
<220> FEATURE:
<221> NAME/KEY: misc_feature
<222> LOCATION: (5)..(40)
<223> OTHER INFORMATION: Ribonucleotide rather than deoxyribonucleotide

<400> SEQUENCE: 104
cugtcggaga cuacucgucg aguagaaaua gguccccucc                          40

<210> SEQ ID NO 105
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (9)..(9)
<223> OTHER INFORMATION: Deoxyribonucleotide rather than ribonucleotide

<400> SEQUENCE: 105
cugucggaga cuacucgucg aguagaaaua gguccccucc                          40

<210> SEQ ID NO 106
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<223> OTHER INFORMATION: L-nucleic acid
<220> FEATURE:
<221> NAME/KEY: misc_feature
<222> LOCATION: (11)..(11)
<223> OTHER INFORMATION: Deoxyribonucleotide rather than ribonucleotide

<400> SEQUENCE: 106
cugucggaga cuacucgucg aguagaaaua gguccccucc                          40

<210> SEQ ID NO 107
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (14)..(14)
<223> OTHER INFORMATION: Deoxyribonucleotide rather than ribonucleotide

<400> SEQUENCE: 107
cugucggaga cuacucgucg aguagaaaua gguccccucc                          40

<210> SEQ ID NO 108
<211> LENGTH: 40
<212> TYPE: RNA
<213> ORGANISM: Artificial
<220> FEATURE:
<223> OTHER INFORMATION: Synthetic
<220> FEATURE:
```

<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (17)..(17)
<223> OTHER INFORMATION: Deoxyribonucleotide rather than ribonucleotide

<400> SEQUENCE: 108
cugucggaga cuacucgucg aguagaaaua gguccccucc                            40

<210> SEQ ID NO 109
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (1)..(17)
<223> OTHER INFORMATION: Ribonucleotide rather than deoxyribonucleotide
<220> FEATURE:
<221> NAME/KEY: misc_feature
<222> LOCATION: (19)..(40)
<223> OTHER INFORMATION: Ribonucleotide rather than deoxyribonucleotide

<400> SEQUENCE: 109
cugucggaga cuacucgtcg aguagaaaua gguccccucc                            40

<210> SEQ ID NO 110
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (19)..(19)
<223> OTHER INFORMATION: Deoxyribonucleotide rather than ribonucleotide

<400> SEQUENCE: 110
cugucggaga cuacucgucg aguagaaaua gguccccucc                            40

<210> SEQ ID NO 111
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (20)..(20)
<223> OTHER INFORMATION: Deoxyribonucleotide rather than ribonucleotide

<400> SEQUENCE: 111
cugucggaga cuacucgucg aguagaaaua gguccccucc                            40

<210> SEQ ID NO 112
<211> LENGTH: 40

```
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (21)..(21)
<223> OTHER INFORMATION: Deoxyribonucleotide rather than ribonucleotide

<400> SEQUENCE: 112 cgucggaga cuacucgucg aguagaaaua gguccccucc                              40

<210> SEQ ID NO 113
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (1)..(22)
<223> OTHER INFORMATION: Ribonucleotide rather than deoxyribonucleotide
<220> FEATURE:
<221> NAME/KEY: misc_feature
<222> LOCATION: (24)..(40)
<223> OTHER INFORMATION: Ribonucleotide rather than deoxyribonucleotide

<400> SEQUENCE: 113 cgucggaga cuacucgucg agtagaaaua gguccccucc                              40

<210> SEQ ID NO 114
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (25)..(25)
<223> OTHER INFORMATION: Deoxyribonucleotide rather than ribonucleotide

<400> SEQUENCE: 114 cugcggaga cuacucgucg aguagaaaua ggucccucc                               40

<210> SEQ ID NO 115
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (28)..(28)
<223> OTHER INFORMATION: Deoxyribonucleotide rather than ribonucleotide

<400> SEQUENCE: 115
``` cgucggaga cuacucgucg aguagaaaua gguccccucc                    40

<210> SEQ ID NO 116
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (1)..(28)
<223> OTHER INFORMATION: Ribonucleotide rather than deoxyribonucleotide
<220> FEATURE:
<221> NAME/KEY: misc_feature
<222> LOCATION: (30)..(40)
<223> OTHER INFORMATION: Ribonucleotide rather than deoxyribonucleotide

<400> SEQUENCE: 116
cugucggaga cuacucgucg aguagaaata gguccccucc                    40

<210> SEQ ID NO 117
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (32)..(32)
<223> OTHER INFORMATION: Deoxyribonucleotide rather than ribonucleotide

<400> SEQUENCE: 117
cugucggaga cuacucgucg aguagaaaua gguccccucc                    40

<210> SEQ ID NO 118
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (34)..(34)
<223> OTHER INFORMATION: Deoxyribonucleotide rather than ribonucleotide

<400> SEQUENCE: 118
cugucggaga cuacucgucg aguagaaaua gguccccucc                    40

<210> SEQ ID NO 119
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature -continued
<222> LOCATION: (36)..(36)
<223> OTHER INFORMATION: Deoxyribonucleotide rather than ribonucleotide

<400> SEQUENCE: 119
cugucggaga cuacucgucg aguagaaaua gguccccucc                             40

<210> SEQ ID NO 120
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (37)..(37)
<223> OTHER INFORMATION: Deoxyribonucleotide rather than ribonucleotide

<400> SEQUENCE: 120
cugucggaga cuacucgucg aguagaaaua gguccccucc                             40

<210> SEQ ID NO 121
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (39)..(39)
<223> OTHER INFORMATION: Deoxyribonucleotide rather than ribonucleotide

<400> SEQUENCE: 121
cugucggaga cuacucgucg aguagaaaua gguccccucc                             40

<210> SEQ ID NO 122
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (40)..(40)
<223> OTHER INFORMATION: Deoxyribonucleotide rather than ribonucleotide

<400> SEQUENCE: 122
cugucggaga cuacucgucg aguagaaaua gguccccucc                             40

<210> SEQ ID NO 123
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:

```
<221> NAME/KEY: misc_feature
<222> LOCATION: (36)..(36)
<223> OTHER INFORMATION: Deoxyribonucleotide rather than ribonucleotide
<220> FEATURE:
<221> NAME/KEY: misc_feature
<222> LOCATION: (39)..(39)
<223> OTHER INFORMATION: Deoxyribonucleotide rather than ribonucleotide

<400> SEQUENCE: 123 cgucggaga cuacucgucg aguagaaaua ggucccaucc                    40

<210> SEQ ID NO 124
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(50)
<223> OTHER INFORMATION: L-nucleic acid
<220> FEATURE:
<221> NAME/KEY: misc_feature
<222> LOCATION: (20)..(20)
<223> OTHER INFORMATION: Deoxyribonucleotide rather than ribonucleotide
<220> FEATURE:
<221> NAME/KEY: misc_feature
<222> LOCATION: (41)..(41)
<223> OTHER INFORMATION: Deoxyribonucleotide rather than ribonucleotide

<400> SEQUENCE: 124
ccgugcuguc ggagacuacu cgucgaguag aaauaggucc ccucccacgg        50

<210> SEQ ID NO 125
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(50)
<223> OTHER INFORMATION: L-nucleic acid
<220> FEATURE:
<221> NAME/KEY: misc_feature
<222> LOCATION: (28)..(28)
<223> OTHER INFORMATION: Deoxyribonucleotide rather than ribonucleotide
<220> FEATURE:
<221> NAME/KEY: misc_feature
<222> LOCATION: (41)..(41)
<223> OTHER INFORMATION: Deoxyribonucleotide rather than ribonucleotide

<400> SEQUENCE: 125
ccgugcuguc ggagacuacu cgucgaguag aaauaggucc ccucccacgg        50

<210> SEQ ID NO 126
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(50)
<223> OTHER INFORMATION: L-nucleic acid
<220> FEATURE:
<221> NAME/KEY: misc_feature
<222> LOCATION: (20)..(20)
<223> OTHER INFORMATION: Deoxyribonucleotide rather than ribonucleotide
<220> FEATURE:
<221> NAME/KEY: misc_feature
<222> LOCATION: (28)..(28)
<223> OTHER INFORMATION: Deoxyribonucleotide rather than ribonucleotide
```

-continued

```
<220> FEATURE:
<221> NAME/KEY: misc_feature
<222> LOCATION: (41)..(41)
<223> OTHER INFORMATION: Deoxyribonucleotide rather than ribonucleotide

<400> SEQUENCE: 126
ccgugcuguc ggagacuacu cgucgaguag aaauaggucc ccucccacgg                50

<210> SEQ ID NO 127
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(50)
<223> OTHER INFORMATION: L-nucleic acid
<220> FEATURE:
<221> NAME/KEY: misc_feature
<222> LOCATION: (20)..(20)
<223> OTHER INFORMATION: Deoxyribonucleotide rather than ribonucleotide
<220> FEATURE:
<221> NAME/KEY: misc_feature
<222> LOCATION: (41)..(41)
<223> OTHER INFORMATION: Deoxyribonucleotide rather than ribonucleotide
<220> FEATURE:
<221> NAME/KEY: misc_feature
<222> LOCATION: (44)..(44)
<223> OTHER INFORMATION: Deoxyribonucleotide rather than ribonucleotide

<400> SEQUENCE: 127
ccgugcuguc ggagacuacu cgucgaguag aaauaggucc ccucccacgg                50

<210> SEQ ID NO 128
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(50)
<223> OTHER INFORMATION: L-nucleic acid
<220> FEATURE:
<221> NAME/KEY: misc_feature
<222> LOCATION: (28)..(28)
<223> OTHER INFORMATION: Deoxyribonucleotide rather than ribonucleotide
<220> FEATURE:
<221> NAME/KEY: misc_feature
<222> LOCATION: (41)..(41)
<223> OTHER INFORMATION: Deoxyribonucleotide rather than ribonucleotide
<220> FEATURE:
<221> NAME/KEY: misc_feature
<222> LOCATION: (44)..(44)
<223> OTHER INFORMATION: Deoxyribonucleotide rather than ribonucleotide

<400> SEQUENCE: 128
ccgugcuguc ggagacuacu cgucgaguag aaauaggucc ccucccacgg                50

<210> SEQ ID NO 129
<211> LENGTH: 50
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(50)
<223> OTHER INFORMATION: L-nucleic acid
<220> FEATURE:
<221> NAME/KEY: misc_feature
<222> LOCATION: (20)..(20)
```

<223> OTHER INFORMATION: Deoxyribonucleotide rather than ribonucleotide
<220> FEATURE:
<221> NAME/KEY: misc_feature
<222> LOCATION: (28)..(28)
<223> OTHER INFORMATION: Deoxyribonucleotide rather than ribonucleotide
<220> FEATURE:
<221> NAME/KEY: misc_feature
<222> LOCATION: (41)..(41)
<223> OTHER INFORMATION: Deoxyribonucleotide rather than ribonucleotide
<220> FEATURE:
<221> NAME/KEY: misc_feature
<222> LOCATION: (44)..(44)
<223> OTHER INFORMATION: Deoxyribonucleotide rather than ribonucleotide

<400> SEQUENCE: 129
ccgugcuguc ggagacuacu cgucgaguag aaauaggucc ccucccacgg         50

<210> SEQ ID NO 130
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (15)..(15)
<223> OTHER INFORMATION: Deoxyribonucleotide rather than ribonucleotide
<220> FEATURE:
<221> NAME/KEY: misc_feature
<222> LOCATION: (36)..(36)
<223> OTHER INFORMATION: Deoxyribonucleotide rather than ribonucleotide

<400> SEQUENCE: 130
cugucggaga cuacucgucg aguagaaaua gguccccucc         40

<210> SEQ ID NO 131
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (23)..(23)
<223> OTHER INFORMATION: Deoxyribonucleotide rather than ribonucleotide
<220> FEATURE:
<221> NAME/KEY: misc_feature
<222> LOCATION: (36)..(36)
<223> OTHER INFORMATION: Deoxyribonucleotide rather than ribonucleotide

<400> SEQUENCE: 131
cugucggaga cuacucgucg aguagaaaua gguccccucc         40

<210> SEQ ID NO 132
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature

```
<222> LOCATION: (15)..(15)
<223> OTHER INFORMATION: Deoxyribonucleotide rather than ribonucleotide
<220> FEATURE:
<221> NAME/KEY: misc_feature
<222> LOCATION: (23)..(23)
<223> OTHER INFORMATION: Deoxyribonucleotide rather than ribonucleotide
<220> FEATURE:
<221> NAME/KEY: misc_feature
<222> LOCATION: (36)..(36)
<223> OTHER INFORMATION: Deoxyribonucleotide rather than ribonucleotide

<400> SEQUENCE: 132
cugucggaga cuacucgucg aguagaaaua gguccccucc                          40

<210> SEQ ID NO 133
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (15)..(15)
<223> OTHER INFORMATION: Deoxyribonucleotide rather than ribonucleotide
<220> FEATURE:
<221> NAME/KEY: misc_feature
<222> LOCATION: (36)..(36)
<223> OTHER INFORMATION: Deoxyribonucleotide rather than ribonucleotide
<220> FEATURE:
<221> NAME/KEY: misc_feature
<222> LOCATION: (39)..(39)
<223> OTHER INFORMATION: Deoxyribonucleotide rather than ribonucleotide

<400> SEQUENCE: 133
cugucggaga cuacucgucg aguagaaaua gguccccucc                          40

<210> SEQ ID NO 134
<211> LENGTH: 40
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: L-nucleic acid
<220> FEATURE:
<221> NAME/KEY: misc_feature
<222> LOCATION: (23)..(23)
<223> OTHER INFORMATION: Deoxyribonucleotide rather than ribonucleotide
<220> FEATURE:
<221> NAME/KEY: misc_feature
<222> LOCATION: (36)..(36)
<223> OTHER INFORMATION: Deoxyribonucleotide rather than ribonucleotide
<220> FEATURE:
<221> NAME/KEY: misc_feature
<222> LOCATION: (39)..(39)
<223> OTHER INFORMATION: Deoxyribonucleotide rather than ribonucleotide

<400> SEQUENCE: 134
cugucggaga cuacucgucg aguagaaaua gguccccucc                          40

<210> SEQ ID NO 135
<211> LENGTH: 41
<212> TYPE: RNA
<213> ORGANISM: Artificial
<220> FEATURE:
<223> OTHER INFORMATION: Synthetic
<220> FEATURE:
```

```
<221> NAME/KEY: misc_feature
<222> LOCATION: (1)..(41)
<223> OTHER INFORMATION: L-nucleic acid
<220> FEATURE:
<221> NAME/KEY: misc_feature
<222> LOCATION: (1)..(1)
<223> OTHER INFORMATION: PEG attached

<400> SEQUENCE: 135
ggacugaugg cgcgguccua uuacgccgau agggugaggg g        41
```